US011535576B2

United States Patent
Li et al.

(10) Patent No.: US 11,535,576 B2
(45) Date of Patent: Dec. 27, 2022

(54) CARBONYL CONTAINING COMPOUND HIGH-THROUGHPUT QUANTITATIVE ANALYSIS USING ISOBARIC MULTIPLEX REAGENTS

(71) Applicant: Wisconsin Alumni Research Foundation, Madison, WI (US)

(72) Inventors: Lingjun Li, Madison, WI (US); Yu Feng, Madison, WI (US); Bingming Chen, Norristown, PA (US); Qinying Yu, Madison, WI (US); Xuefei Zhong, Seattle, WA (US); Miyang Li, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 630 days.

(21) Appl. No.: 16/252,464

(22) Filed: Jan. 18, 2019

(65) Prior Publication Data

US 2019/0225559 A1    Jul. 25, 2019

Related U.S. Application Data

(60) Provisional application No. 62/619,414, filed on Jan. 19, 2018.

(51) Int. Cl.
*G01N 33/50* (2006.01)
*G01N 33/68* (2006.01)
*C07B 59/00* (2006.01)

(52) U.S. Cl.
CPC ....... *C07B 59/001* (2013.01); *G01N 33/6848* (2013.01); *C07B 2200/05* (2013.01);
(Continued)

(58) Field of Classification Search
CPC .............. G01N 2458/15; C07B 59/001; C07B 2200/05
See application file for complete search history.

(56) References Cited

U.S. PATENT DOCUMENTS

| 9,388,132 B2 | 7/2016 | Li et al. | |
| 2013/0078728 A1* | 3/2013 | Li | C07D 207/46 436/86 |
| 2015/0241437 A1* | 8/2015 | Zhang | C08B 37/00 536/55 |

OTHER PUBLICATIONS

"Hydrazines," IUPAC. Compendium of Chemical Terminology, 2nd ed. (the "Gold Book"). Compiled by A. D. McNaught and A. Wilkinson. Blackwell Scientific Publications, Oxford (1997). https://doi.org/10.1351/goldbook.H02881 (Year: 1997).*
(Continued)

*Primary Examiner* — Jennifer Wecker
*Assistant Examiner* — Michelle Adams
(74) *Attorney, Agent, or Firm* — Leydig, Voit & Mayer, Ltd

(57) ABSTRACT

The present invention provides a set of novel isobaric chemical tags, also referred herein as SUGAR (Isobaric Multiplex Reagents for Carbonyl Containing Compound). These labeling tags are compact and easy to synthesize at high yield and purity in just a few steps using commercially available starting materials. The tagging reagents of the present invention comprise: a) a reporter group, having at least one atom that is optionally isotopically labeled; b) a balancing group, also having at least one atom that is optionally isotopically labeled, and c) an aldehyde, ketone, or carboxylic acid reactive group. The multiplex SUGAR tags are able to react with an aldehyde, ketone, or carboxylic acid group of the molecule to be tagged, which offers the capability for labeling and quantitation of glycans, proteins/peptides, and fatty acids.

13 Claims, 40 Drawing Sheets

SUGAR-115

SUGAR-116

SUGAR-117

SUGAR-118

(52) U.S. Cl.
CPC ..... *G01N 2440/38* (2013.01); *G01N 2458/15* (2013.01); *G01N 2570/00* (2013.01); *G01N 2800/52* (2013.01); *Y10T 436/143333* (2015.01)

(56) References Cited

OTHER PUBLICATIONS

"Hydrazides," IUPAC. Compendium of Chemical Terminology, 2nd ed. (the "Gold Book"). Compiled by A. D. McNaught and A. Wilkinson. Blackwell Scientific Publications, Oxford (1997). https://doi.org/10.1351/goldbook.H02879 (Year: 1997).*
Bowman, M.J. et al. "Tags for the Stable Isotopic Labeling of Carbohydrates and Quantitative Analysis by Mass Spectrometry," Anal. Chem. 2007, 79, 5777-5784 (Year: 2007).*
Kaminski, Z.J. et al. "Mild and Efficient Synthesis of Carboxylic Acid Anhydrides from Carboxylic Acids and Triazine Coupling Reagents," Synthetic Communications vol. 34, No. 18, pp. 3349-3358, 2004 (Year: 2004).*
Supporting Information for Yang et al. "Glycan Analysis by Isobaric Aldehyde Reactive Tags and Mass Spectrometry", Anal. Chem., 85(17): 8188-8195 (2013) (Year: 2013).*
Yun, J. et al. "Isotope labeling strategies of glycans for mass spectrometry-based quantitative glycomics," Microchemical Journal 170 (2021) 106655, pp. 1-7 (Year: 2021).*
Boehm, et al., "Precise protein quantification based on peptide quantification using iTRAQ™", *BMC Bioinformatics*, 8:214 (2007).
Alley et al., "High-sensitivity Analytical Approaches for the Structural Characterization of Glycoproteins", *Chem. Rev.*, 113(4): 2668-2732 (2013).
An et al., "Glycomics and disease markers", *Curr. Opin. Chem. Biol.*, 13 (5-6): 601-607 (2009).
Anumula et al., "Advances in fluorescence derivatization methods for high-performance liquid chromatographic analysis of glycoprotein carbohydrates", *Anal. Biochem.*, 350(1): 1-23 (2006).
Anumula et al., "High resolution and high sensitivity methods for oligosaccharide mapping and characterization by normal phase high performance liquid chromatography following derivatization with highly fluorescent anthranilic acid", *Glycobiology*, 8(7): 685-694 (1998).
Anumula, "Quantitative Determination of Monosaccharides in Glycoproteins by High-Performance Liquid Chromatography with Highly Sensitive Fluorescence Detection," *Anal. Biochem.*, 220(2): 275-283 (1994).
Arnold et al., "Evaluation of the serum N-linked glycome for the diagnosis of cancer and chronic inflammation", *Proteomics*, 8 (16): 3284-3293 (2008).
Atwood et al., "Quantitation by Isobaric Labeling: Applications to Glycomics", *J. Proteome Res.*, 7(1): 367-374 (2008).
Aye et al., "Selectivity in Enrichment of cAMP-dependent Protein Kinase Regulatory Subunits Type I and Type II and Their Interactors Using Modified cAMP Affinity Resins", *Mol. Cell. Proteomics*, 8(5):1016-1028 (2009).
Bigge et al. "Nonselective and Efficient Fluorescent Labeling of Glycans Using 2-Amino Benzamide and Anthranilic Acid", *Anal. Biochem.*, 230(2): 229-238 (1995).
Boersema et al., "Multiplex peptide stable isotope dimethyl labeling for quantitative proteomics", *Nat. Protocols*, 4:484-494 (2009).
Boersema et al., "Triplex protein quantification based on stable isotope labeling by peptide dimethylation applied to cell and tissue lysates", *Proteomics*, 8:4624-4632 (2008).
Bork et al., "Increasing the sialylation of therapeutic glycoproteins: The potential of the sialic acid biosynthetic pathway", *J. Pharm Sci.*, 98 (10): 3499-3508 (2009).
Choe et al., "8-Plex quantitation of changes in cerebrospinal fluid protein expression in subjects undergoing intravenous immunoglobulin treatment for Alzheimer's disease", *Proteomics*, 7(20):3651-3660 (2007).

Chen et al., "Quantitative Glycomic Analysis by Mass-Defect-Based Dimethyl Pyrimidinyl Ornithine (DiPyrO) Tags and High-Resolution Mass Spectrometry", *Anal. Chem.*, 90 (13): 7817-7823 (May 2018).
Dayon et al., "Relative Quantification of Proteins in Human Cerebrospinal Fluids by MS/MS Using 6-Plex Isobaric Tags," *Anal. Chem.*, 80:2921-2931 (2008).
Defaus et al., "Mammalian protein glycosylation—structure versus function," *Analyst*, 139(12): 2944-2967 (2014).
Dwek, "Glycobiology: Toward Understanding the Function of Sugars", *Chem. Rev.*, 96(2): 683-720 (1996).
Evangelista et al., "Acid-catalyzed reductive amination of aldoses with 8-aminopyrene-1,3,6-trisulfonate", *Electrophoresis*, 17(2): 347-51 (1996).
Frost et al., "High-Resolution Enabled 12-Plex DiLeu Isobaric Tags for Quantitative Proteomics", *Anal. Chem.*, 87(3): 1646-1654 (2015).
Frost et al., "Development and characterization of novel 8-plex DiLeu isobaric labels for quantitative proteomics and peptidomics", *Rapid Commun. Mass Spectrom*, 29 (12): 1115-1124 (2015).
Gaynon et al., "Long-term results of the children's cancer group studies for childhood acute lymphoblastic leukemia 1983-2002: A Children's Oncology Group Report", *Leokemia*, 24(2): 285-297 (2010).
Guo et al., "Stable-Isotope Dimethylation Labeling Combined with LC-ESI MS for Quantification of Amine-Containing Metabolites in Biological Samples", *Anal. Chem.*, 79(22):8631-8638 (2007).
Gygi et al., "Quantitative analysis of complex protein mixtures using isotope-coded affinity tags", *Nat. Biotechnol.*, 17:994-999 (1999).
Hahne et al., "Carbonyl-Reactive Tandem Mass Tags for the Proteome-Wide Quantification of N-Linked Glycans", *Anal. Chem.*, 84 (8): 3716-3724 (2012).
Hansen et al., "Mass Spectrometric Analysis of Protein Mixtures at Low Levels Using Cleavable 13C-Isotope-coded Affinity Tag and Multidimensional Chromatography", *Mol. Cell. Proteomics*, 2(5):299-314 (2003).
Hitchcock et al., "Comparative glycomics of connective tissue glycosaminoglycans", *Proteomics*, 8 (7): 1384-1397 (2008).
Hsu et al., "Stable-Isotope Dimethyl Labeling for Quantitative Proteomics", *Anal. Chem.*, 75(24):6843-6852 (2003).
Hsu et al., "Dimethyl multiplexed labeling combined with microcolumn separation and MS analysis for time course study in proteomics", *Electrophoresis*, 27(18):3652-3660(2006).
Huang et al., "Quantitation of protein phosphorylation in pregnant rat uteri using stable isotope dimethyl labeling coupled with IMAC", *Proteomics*, 6(6):1722-1734 (2006).
Ji et al., "A study of reproducibility of guanidination-dimethylation labeling and liquid chromatography matrix-assisted laser desorption ionization mass spectrometry for relative proteome quantification", *Anal. Chim. Acta*, 585(2):219-226 (2007).
Ji et al., "Identification and Quantification of Differentially Expressed Proteins in E-Cadherin Deficient SCC9 Cells and SCC9 Transfectants Expressing E-Cadherin by Dimethyl Isotope Labeling, LC-MALDI MS and MS/MS", *Proteome Res.*, 4(4):1419-1426 (2005).
Ji et al., "Differential Dimethyl Labeling of N-Termini of Peptides after Guanidination for Proteome Analysis", *Proteome Res.*, 4(6):2099-2108 (2005).
Ji et al., "Quantitative Proteome Analysis Using Differential Stable Isotopic Labeling and Microbore LC-MALDI MS and MS/MS", *Proteome Res.*, 4(3):734-742 (2005).
Ji et al., "Effect of 2MEGA Labeling on Membrane Proteome Analysis Using LC-ESI QTOF MS," *Proteome Res.*, 5(10):2567-2576 (2006).
Kaatsch et al., "Epidemiology of childhood cancer", *Cancer Treat. Rev.*, 36 (4): 277-285 (2010).
Khidekel et al., "Probing the dynamics of O-GlcNAc glycosylation in the brain using quantitative proteomics", *Nat. Chem. Biol.*, 3:339-348 (2007).
Krawczuk-Rybak et al., "Intellectual functioning of childhood leukemia survivors—relation to Tau protein—a marker of white matter injury", *Adv. Med. Sci.*, 57(2): 266-72 (2012).

(56) References Cited

OTHER PUBLICATIONS

Lemeer et al., "Comparative Phosphoproteomics of Zebrafish Fyn/Yes Morpholino Knockdown Embryos", *Mol. Cell. Proteomics*, 7:2176-2187 (2008).
Li et al., "Protein Profiling with Cleavable Isotope-coded Affinity Tag (cICAT) Reagents," *Mol. Cell. Proteomics*, 2(11):1198-1204 (2003).
Morano et al., "Multiple Isotopic Labels for Quantitative Mass Spectrometry", *Anal. Chem.*, 80:9298-9309 (2008).
Moremen et al., "Vertebrate protein glycosylation: diversity, synthesis and function", *Nat. Rev. Mol. Cell Biol.*, 13 (7): 448-462 (2012).
Norton et al., "N-linked glycosylation of the liver cancer biomarker GP73", *J. Cell Biochem.*, 104(1): 136-149 (2008).
Ong et al., "Stable Isotope Labeling by Amino Acids in Cell Culture, SILAC, as a Simple and Accurate Approach to Expression Proteomics", *Mol. Cell. Proteomics*, 1(5):376-386 (2002).
Ong et al., "Mass spectrometry-based proteomics turns quantitative", *Nat. Chem. Biol.*, 1:252-262 (2005).
Rahman, et al., "Filter-Aided N-Glycan Separation (FANGS): A Convenient Sample Preparation Method for Mass Spectrometric N-Glycan Profiling", *J Proteome Res*, 13 (3): 1167-1176 (2014).
Raijmakers et al., "Automated Online Sequential Isotope Labeling for Protein Quantitation Applied to Proteasome Tissue-specific Diversity", *Mol. Cell. Proteomics*, 7(9):1755-1762 (2008).
Rogers et al., "The dynamic phagosomal proteome and the contribution of the endoplasmic reticulum", *Proc. Natl. Acad. Sci. U.S.A.*, 104(47):18520-18525 (2007).
Ross et al., "Multiplexed Protein Quantitation in *Saccharomyces cerevisiae* Using Amine-reactive Isobaric Tagging Reagents", *Mol. Cell. Proteomics*, 3(12):1154-1169 (2004).
Royle et al., "HPLC-based analysis of serum N-glycans on a 96-well plate platform with dedicated database software", *Anal Biochem.*, 376 (1): 1-12 (2008).
Ow et al., iTRAQ Underestimation in Simple and Complex Mixtures: "The Good, the Bad and the Ugly", *J. Proteome Res.*, 8(11):5347-5355 (2009).
Speechley et al., "Health-Related Quality of Life Among Child and Adolescent Survivors of Childhood Cancer", *J. Clin. Oncol.*, 24 (16): 2536-2543 (2006).
Synowsky et al., "Comparative Multiplexed Mass Spectrometric Analyses of Endogenously Expressed Yeast Nuclear and Cytoplasmic Exosomes", *J. Mol. Biol.*, 385(4):1300-1313 (2009).
Taniguchi et al., "Human Disease Glycomics/Proteome Initiative (HGPI)", *Mol. Cell. Proteomics*, 7(3): 626-627 (2008).
Thompson et al., "Tandem Mass Tags: A Novel Quantification Strategy for Comparative Analysis of Complex Protein Mixtures by MS/MS", *Anal. Chem.*, 75:1895-1904 (2003).
Wang et al., "Targeted Quantitative Mass Spectrometric Identification of Differentially Expressed Proteins between Bax-Expressing and Deficient Colorectal Carcinoma Cells", *J. Proteome Res.*, 8:3403-3414 (2009).
Xia et al., "Glycan reductive isotope labeling for quantitative glycomics", *Anal. Biochem.*, 387(2): 162-70 (2009).
Xiang, et al., "N,N-Dimethyl Leucines as Novel Isobaric Tandem Mass Tags for Quantitative Proteomics and Peptidomics," *Anal. Chem.*, 82(7):2817-2825 (2010).
Yang et al., "Glycan Analysis by Isobaric Aldehyde Reactive Tags and Mass Spectrometry", *Anal. Chem.*, 85(17): 8188-8195 (2013).
Yang et al., "QUANTITY: An Isobaric Tag for Quantitative Glycomics", *Sci. Rep.*, 5:17585 (2015).
Yuan et al., "Isotope tag method for quantitative analysis of carbohydrates by liquid chromatography-mass spectrometry", *J. Chromatogr. A*, 1067(1-2): 145-152 (2005).
Zeng et al., "Revival of deuterium-labeled reagents for protein quantitation," *Chem. Common.*, 3369-3371 (2009).
Zhang et al., "Controlling Deuterium Isotope Effects in Comparative Proteomics", *Anal. Chem.*, 74(15):3662-3669 (2002).

\* cited by examiner

2-AB                    2-AA                    PA

APTS                    ANTS

Derivatization reagents for florescence detection 6-plex aminoxyTMT (stars indicate the isotope position)

Limitations of aminoxyTMT quantification

Low collisional energy
- Low reporter ion yield for complex N-glycan
- Inaccurate reporter ion ratio
- Backbone fragment preserved for N-glycan identification

High collisional energy
- High reporter ion yield & accurate reporter ion ratio
- No backbone fragment (difficult for identification)

Proposed QUANTITY fragmentation pathway

DiLeu-based glycan tags

Synthesis of A-DiLeu

Synthesis of HG-DiLeu

CARBONYL CONTAINING COMPOUND HIGH-THROUGHPUT QUANTITATIVE ANALYSIS USING ISOBARIC MULTIPLEX REAGENTS

CROSS-REFERENCE TO RELATED APPLICATIONS

This application claims priority from U.S. Provisional Patent Application No. 62/619,414, filed Jan. 19, 2018, which is incorporated by reference herein to the extent that there is no inconsistency with the present disclosure.

STATEMENT REGARDING FEDERALLY SPONSORED RESEARCH OR DEVELOPMENT

This invention was made with government support under AG055377 and DK071801 awarded by the National Institutes of Health. The government has certain rights in the invention.

BACKGROUND OF THE INVENTION

Quantitative measurements of proteins and small molecules are essential to understanding biological systems and disease mechanisms. For example, proteomics is a systematic study that aims to comprehensively characterize and quantify proteins in a biological system. Mass spectrometry (MS) is the most common tool in proteomic analysis.

There are two main types of quantification strategies in such studies. One of them is label free quantification. The extracted molecules (e.g., proteins) are digested by an enzyme, separated by chromatographic or electrophoretic system, followed by detection on a mass spectrometer for identification and quantitation. The database searching engine compares the theoretical spectra and experimental spectra to identify peptides and proteins. The quantification result is generated by comparing the intensity of every species in different samples. For label free quantification strategy, the sample preparation is relatively straightforward and less time consuming while the MS-based data acquisition would require more instrument time since only one sample could be analyzed in a single LCMS experiment.

The alternative strategy is chemical labeling prior to the LCMS analysis. The molecules (e.g., protein analytes) are enzymatically digested, labeled with chemical tags, purified, separated and analyzed by an LCMS system. The identification process is almost the same with addition of derivative as a fixed chemical modification. The quantification result is produced by comparing either the intensities of signature ions or peak areas under curve resulting from different isotopic labeling tags.

The most commonly used chemical labeling is isobaric labeling because of the high plex capacity, simple spectral identification and accurate relative quantification. There are several chemical derivatization reagents for proteomics including TMT, iTRAQ and DiLeu-based tags. Such conventional tags react with primary amines at the N-terminus of peptides or lysine side chains, although several reagents have been developed for C-terminal derivatization. Additional isobaric tagging reagents containing amine reactive groups and enabling 8 plex and 16 plex analysis were also developed and described in U.S. Pat. No. 9,388,132.

However, limited success has been achieved for quantitative analysis of C-terminally labeled peptides via isobaric tagging strategy. Since the charge state of C-terminally labeled peptides could be increased efficiently compared to negatively charged carboxylic acid without a label, the labile post-translational modifications (PTMs) analysis with electron-transfer dissociation (ETD) or electron-transfer/higher-energy collision dissociation (EThcD) fragmentation would be beneficial with C-terminal derivatization. Higher charge state peptides would produce better fragmentation via ETD or EThcD fragmentation with confident identification and better sequence coverage.

With technological advancement of MS, MS-based quantitative glycomics has also become promising. The backbone fragments produced during MS fragmentation can be used to elucidate structure for characterization while intensities of parent ions or fragment peaks enable relative quantification of glycans.

MS-based stable isotope labeling remains a key technology to quantify proteins, glycans, small molecules, and metabolites, where stable heavy isotopes can be differentially incorporated into analytes chemically (e.g., labeling tags) or metabolically (e.g., SILAC). Compared to label-free approaches, stable isotope labeling allows for simultaneous comparison of multiple samples in a single MS run (multiplexing) with improved accuracy and reduced systematic variation for quantitative proteomics and metabolomics.

Glycans (or carbohydrates) are ubiquitous in biological system and are involved in a wide range of biological functions, including protein folding, cell adhesion and trafficking, cell signaling, fertilization and embryogenesis; and pathogen recognition and immune responses. Furthermore, glycosylation is one of the most important post-translational modifications of peptides and is involved in several biological processes, including cell-cell recognition, communication, and immunity response. Abnormal glycosylation has been implicated in a number of diseases, including cancer, cardiovascular disease, and immunological disorders.

Glycans are highly complex entities with multiple building units and different degrees of branched polymerization. Intensive research efforts have been directed to mass spectrometry (MS)-based qualitative and quantitative glycomic analysis due to important functions of glycans. However, the complexity of carbohydrates, which is amplified by the presence of stereo-isomers, anomeric configurations, branched chains, and modifications such as sulfation, methylation, and phosphorylation, render study of the biological roles of glycans intractable to most biomedical researchers. Compared to genomics and protein biochemistry, glycoscience suffers from the inability to carry out high throughput synthesis or structural and functional analysis of glycans.

As a result, researchers have attempted to develop isobaric chemical tags for glycan MS analysis. Unfortunately, the performance of these tags has left a lot to be desired. For example, AminoxyTMT, a set of commercially available tags from Thermo Scientific, suffers from limited reporter ion yield and poor labeling efficiency for complex glycans. Thus, there is a need for a set of improved tags that address these limitations.

SUMMARY OF THE INVENTION

To overcome the limitations of existing isobaric chemical tags, the present invention provides improved compositions and methods of labeling glycans and other molecules using novel isobaric tandem mass spectrometry ($MS^2$) tagging reagents with high quantitation efficacy and greatly reduced cost for proteomics, glycomics, glycomic quantitation, and small molecule quantification. In particular, the present invention provides isobaric labeling tags useful for the analysis of molecules containing aldehyde, ketone, or carboxylic acid groups. In certain aspects, the present invention provides the design and synthesis of a set of novel amino acid and N,N-dimethylated amino acid-based isobaric 8-plex (or greater) reagents, 12-plex (or greater) reagents, as well as 16-plex (or greater) reagents, able to bind to aldehyde, ketone, and carboxylic acid groups. Preliminary data of synthesis and glycan labeling is also presented.

In an embodiment, the present invention provides a set of novel isobaric chemical tagging reagents, coined SUGAR (Isobaric Multiplex Reagents for Carbonyl Containing Compound), that are compact and easy to synthesize at high yield (greater than 50%) and purity in just a few steps using commercially available starting materials as generally shown in Scheme 1 below:

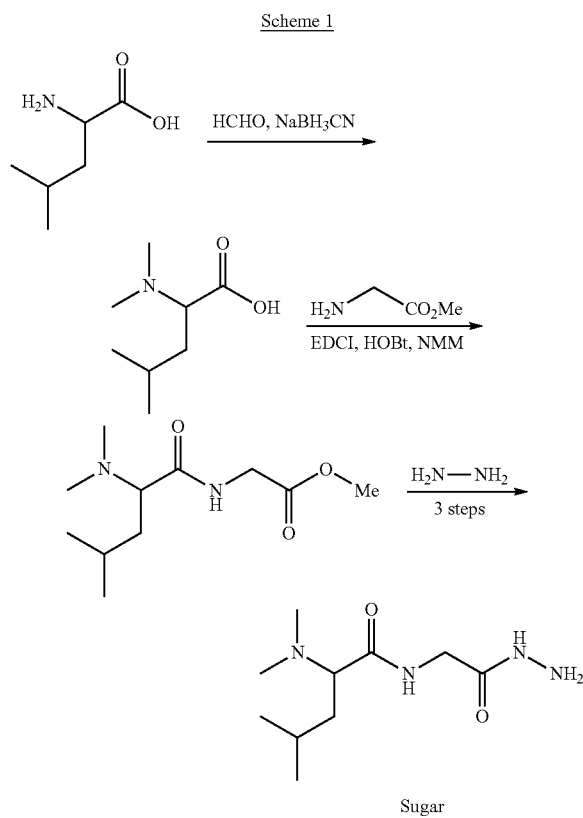

Scheme 1

Sugar

The multiplex SUGAR tags are both aldehyde-reactive and carboxylic acid-reactive, offering the capability for labeling and quantitation of glycans, proteins/peptides, and fatty acids. For 4-plex SUGAR tags, the reporter ions with 1 Da mass difference in MS$^2$ spectra allow the use of mass spectrometers with modest resolution (resolving power <60K), making them compatible with a variety of instrument platforms and accessible to a larger number of users.

The tagging reagents of the present invention comprise: a) a reporter group, having at least one atom that is optionally isotopically labeled; b) a balancing group, also having at least one atom that is optionally isotopically labeled, and c) an aldehyde, ketone, or carboxylic acid reactive group able to react with an aldehyde, ketone, or carboxylic acid group of the molecule to be tagged, such as a glycosylated side chain of a peptide.

A major limiting factor of previous isobaric tagging reagents is that they are limited to use with molecules having amine groups and are unable to react with carboxylic acid groups, or similar reactive groups, present in glycans. For example, activated carboxylic acid groups in previous tagging reagents cannot react with the reducing end of a glycan to form the conjugates for MS analysis. Similarly, previous isobaric tagging reagents are limited in the number of atoms able to be isotopically labeled in the balancing group. For example, previously reported dimethylated leucine (DiLeu) 4-plex reagents able to react to amine groups of peptides utilize isotopic carbonyl groups, which only contain two atoms. As a result, only four isotopic combinations can be achieved within the balancing group. The isobaric tagging reagents of the present invention have balancing groups able to provide a greater number of isotopic combinations. As a result, the present invention provides compositions and methods of tagging peptides and other molecules using, at least, 8-plex, 12-plex, and 16-plex isobaric tandem mass tagging reagents, including novel N,N-dimethylated amino acid based 8-plex, 12-plex, and 16-plex tagging reagents.

In one embodiment, multiple tagging reagents are used to label two or more molecules having at least one aldehyde, ketone, or carboxylic acid group, or a mixture of such molecules, wherein the tagging reagents have the same molecular weight as one another, but wherein the reporter group of each tagging reagent has a different mass due to the different isotopically labeled atoms in each reporter group. Similarly, the balancing group of each tagging reagent has a different mass from one another due to the different isotopically labeled atoms in each balancing group. In one embodiment, each molecule sample is labeled individually, pooled together, and introduced into the mass spectrometer for quantitative analysis. Since the tagging reagents have the same mass, the labeled molecules will produce a single peak in MS mode, but upon MS$^2$ fragmentation, each sample labeled with a different tagging reagent will produce a unique reporter ion due to the mass difference between the reporter groups. Preferably, a molecule labeled with a tagging reagent of the present invention is able to form a strong immonium ion during MS$^2$ fragmentation.

The tagging reagents of the present invention can be used to label and quantify a wide range of molecules provided that the molecule contains an aldehyde, ketone, or carboxylic acid group able to react with the reactive group of the tagging reagent. For example, the molecules able to be labeled using the compounds described herein include, but are not limited to, glycosylated peptides, lipids, and other biological compounds. In an embodiment, a target biological molecule in two or more samples is labeled and subsequently analyzed using the tagging reagents of the present invention, where at least one sample is a biological sample taken from a patient before a treatment is administered to the patient, and one or more samples are biological samples taken from the patient at one or more time periods after the treatment has been administered to the patient. In this way, the present invention can be used to determine if a treatment results in the increased or decreased presence of a biological molecule in the patient as a result of the treatment. Optionally, the patient is a cancer patient and the treatment is an anti-cancer treatment, such as chemotherapy or radiation therapy. The sample taken from the patient may include, but is not limited to, a fluid sample (such as blood), cell sample, or tissue sample (e.g., tissue biopsy). In an embodiment, the treatment is the administration of a drug or therapeutic which may result in the increase or decrease of a biological molecule or metabolite.

In one embodiment, the SUGAR tagging reagents of the present invention are derived from a dipeptide comprising two amino acids. Preferably the amino acids are natural amino acids, but the present invention contemplates the use of unnatural, non-standard and synthetic amino acids, such as p amino acids, as the amino acid which makes up the reporter group, the balancing group, or both. In a further embodiment, the tagging reagents of the present invention are derived from a dipeptide where the amino group of one amino acid has been dimethylated. During $MS^2$ fragmentation, the dipeptide will fragment to form a reporter ion, preferably an immonium ion, which can be readily detected. In a further embodiment, the SUGAR tagging reagents are groups each having a different mass, including one reporter group containing no heavy isotopes. The balancing groups of each reagent will contain the appropriate number of heavy isotopes, such as $^{18}O$, $^{13}C$, $^{15}N$ or D, so that the combined mass of the balancing group and reporter group are the same for each reagent. Varying the atoms which contain the heavy isotope form in the reporter groups and balancing groups allows each tagging reagent to have the same combined mass but a different mass of the reporter group after fragmentation.

Scheme 2

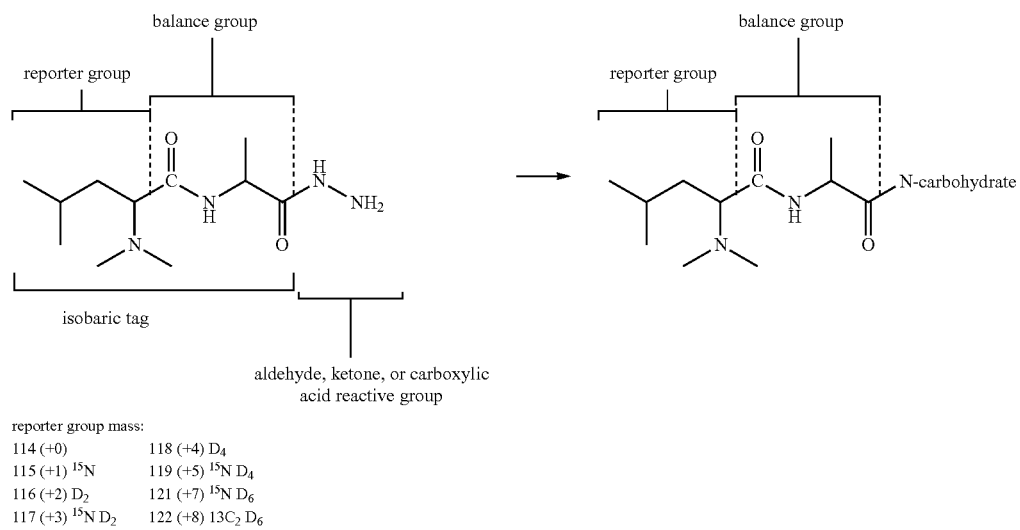

reporter group mass:
114 (+0)          118 (+4) $D_4$
115 (+1) $^{15}N$      119 (+5) $^{15}N\ D_4$
116 (+2) $D_2$         121 (+7) $^{15}N\ D_6$
117 (+3) $^{15}N\ D_2$  122 (+8) $^{13}C_2\ D_6$ derived from N,N-dimethyl leucine (DiLeu); N,N-dimethyl isoleucine (DiIle); N,N-dimethyl alanine (DiAla); N,N-dimethyl glycine (DiGly); N,N-dimethyl valine (DiVal); N,N-dimethyl histidine (DiHis); N,N-dimethyl phenylalanine (DiPhe); N,N-dimethyl tryptophan (DiTrp); N,N-dimethyl lysine (DiLys) or N,N-dimethyl tyrosine (DiTyr).

DiLeu derivative tandem mass tags show improved reporter ion yield and labeling efficiency compared to the current commercially available tags. Low relative error (<15%) and standard deviation prove the excellent quantification accuracy and precision. DiLeu derivative tags are highly promising for glycomic analysis in complex biological systems and can be powerful tools to study glycosylation patterns in diseases.

As an example, a series of isobaric tagging reagents may comprise a reporter group (which forms the reporter ion during fragmentation), a balance group, and an aldehyde, ketone, or carboxylic acid reactive group as shown below in Scheme 2 (using N,N-dimethyl leucine and alanine as the amino acids). One or more atoms in the reporter group, balancing group, or both, in each reagent are the isotopically heavy versions of the atom. Each tagging reagent in the series will have a different combination of atoms that are the isotopically heavy versions of the atoms, but with the condition that the total aggregate mass of each tagging reagent is the same as the other tagging reagents in the series. For example, the nitrogen atom in the reporter group shown in Scheme 2 may be $^{15}N$, one or more carbon atoms may be $^{13}C$, and one or more hydrogen atoms may be deuterium (D). This provides at least eight possible reporter While the SUGAR tags illustrated in Schemes 1 and 2 have an aldehyde, ketone, or carboxylic acid reactive group which is a hydrazide, the reactive group can be any functional group able to react with an aldehyde, ketone, or carboxylic acid group of a molecule thereby forming bond between the molecule and the balancing group of the tagging reagent. In an embodiment, the reactive group includes, but is not limited to, a hydrazide, hydrazine, amine, or oxyamine.

The tagging reagents are reacted with one or more samples containing a molecule of interest containing an aldehyde, ketone, or carboxylic acid reactive group, such as a glycosylated peptide. The samples may then be combined together or with a known standard labeled with one of the tagging reagents. The combined sample is then analyzed using mass spectrometry. After fragmentation, the reporter group for each tagged peptide or molecule will present a different mass due to the differently isotopically labeled atoms. By comparing the relative signal intensity of the detected reporter groups during tandem mass spectrometry, the amounts of each tagged molecule can be quantified, especially if a known standard is used as one of the tagged molecules.

In one embodiment, the tagging reagents (absent the aldehyde, ketone, or carboxylic acid reactive group) preferably have a molecular mass between approximately 125 and 400 Daltons, preferably between approximately 150 and 350 Daltons, even more preferably between approximately 180 and 250 Daltons. This allows the reporter group to have a large enough mass to be readily detected during mass spectrometry analysis, while larger tagging reagents may result in inefficient synthesis and labeling due to steric hindrance.

Fragmentation may be achieved using a variety of methods including, but not limited to, collision induced dissociation (CID), higher-energy collision dissociation (HCD), surface induced dissociation (SID), laser induced dissociation (LID), electron capture dissociation (ECD), electron transfer dissociation (ETD), ultraviolet photo-dissociation (UVPD) or any combination of these methods or any equivalents known in the art of tandem mass spectrometry. The molecule fragments are then detected, identified and optionally quantified using methods as known in the art.

Methods of Analyzing a Mixture Using at Least 8-Plex or 16-Plex Tagging Reagents In one embodiment, the present invention provides a method of analyzing a molecule having an amine group comprising the steps of: a) providing the molecule; b) labeling the molecule with a compound having the formula of:

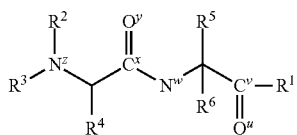

(formula 1)

wherein,

R$^1$ is an aldehyde, ketone, or carboxylic acid reactive group;

R$^2$, R$^3$, R$^4$, R$^5$ and R$^6$, independently of one another, are selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein each of R$^2$, R$^3$, R$^4$, R$^5$ and R$^6$ optionally contain one or more $^{13}$C atoms and one or more deuterium atoms;

C$^v$ and C$^x$, independently of one another, are $^{12}$C or $^{13}$C, O$^U$ and O$^y$, independently of one another, are $^{16}$O or $^{18}$O; and N$^z$ and N$^W$, independently of one another, are $^{14}$N or $^{15}$N, and c) fragmenting the labeled molecule to generate an immonium ion from the labeled molecule; and d) detecting and analyzing fragments of the labeled molecule. In an embodiment, R$^2$ and R$^3$, independently of one another, are CH$_3$, $^{13}$CH$_3$, CDH$_2$, $^{13}$CDH$_2$, CD$_2$H, $^{13}$CD$_2$H, CD$_3$ or $^{13}$CD$_3$. In an embodiment, at least one of R$^2$ or R$^3$ contains a deuterium atom, and N$^z$ is $^{15}$N, or N$^W$ is $^{15}$N. In an embodiment, R$^6$ is hydrogen or deuterium. Optionally, R$^1$ comprises a hydrazide, hydrazine, amine, or oxyamine.

Preferably, R$^4$ and R$^5$ are selected from the group consisting of hydrogen, deuterium, branched and unbranched $C_1$ to $C_8$ alkyl groups, $C_1$ to $C_8$ cycloalkyl groups, $C_1$ to $C_{o8}$ alkenyl groups, $C_1$ to $C_8$ cycloalkenyl groups, $C_6$ to $C_{12}$ aryl groups and $C_6$ to $C_{12}$ arylalkyl groups. In one embodiment, R$^4$ and R$^5$ are selected from the group consisting of hydrogen, deuterium, branched and unbranched $C_1$ to $C_4$ alkyl groups, $C_1$ to $C_4$ cycloalkyl groups, and $C_2$ to $C_4$ alkenyl groups.

Labeling the molecule comprises the step of reacting the aldehyde, ketone, or carboxylic acid reactive group of the tagging reagent with the aldehyde, ketone, or carboxylic acid group of the molecule. In one embodiment, the molecule is a glycosylated peptide or molecule, and the labeled molecule has the formula:

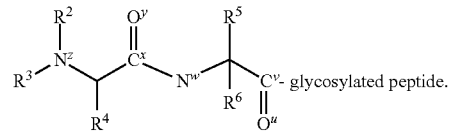

(formula 2)

In one embodiment, the compound has the formula:

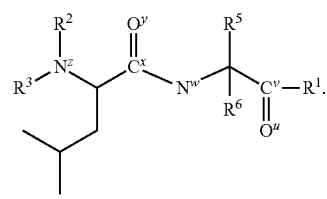

(formula 5)

In a further embodiment, R$^5$ is a methyl group optionally containing one or more deuterium atoms and wherein the carbon is $^{12}$C or $^{13}$C; R$^5$ is hydrogen or deuterium; or R$^5$ is an isopropyl group optionally containing one or more deuterium atoms and one or more $^{13}$C atoms.

In a further embodiment, the compound is selected from:

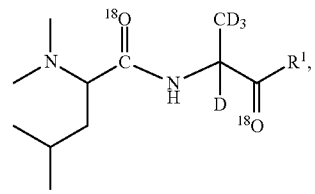

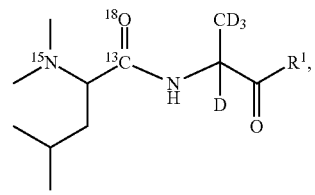

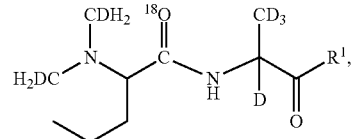

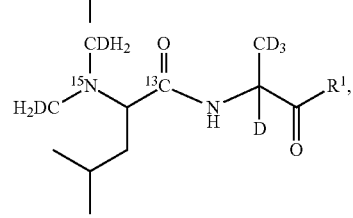

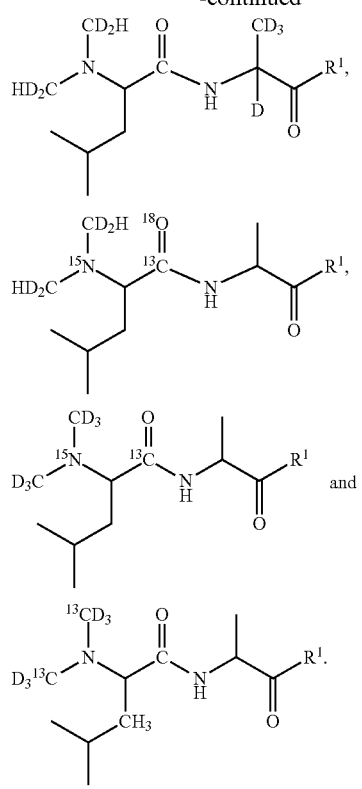
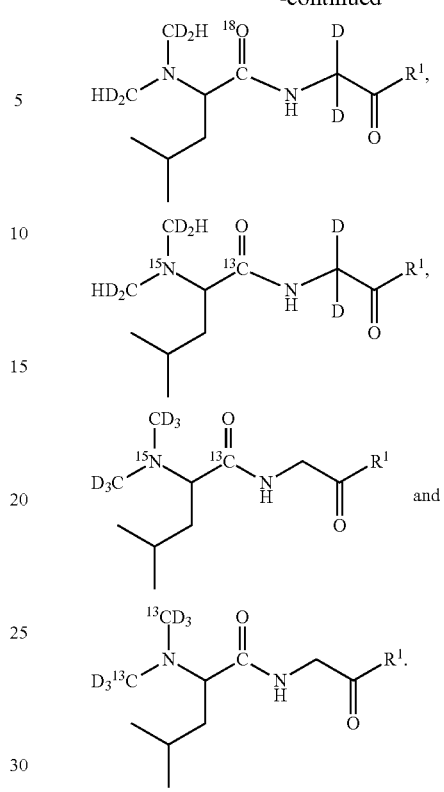
In a further embodiment, the compound is selected from:
In a further embodiment, the compound is selected from:
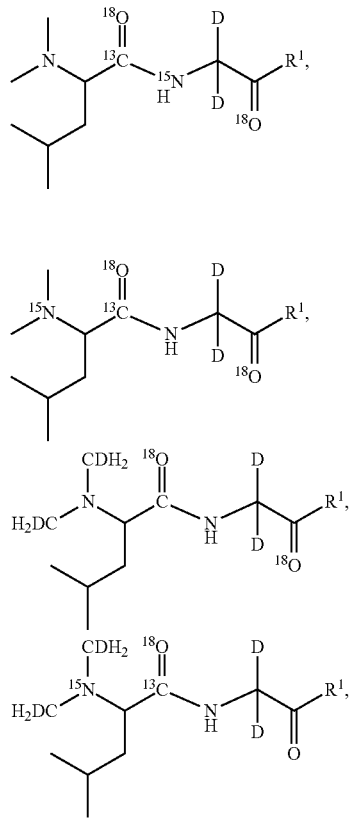

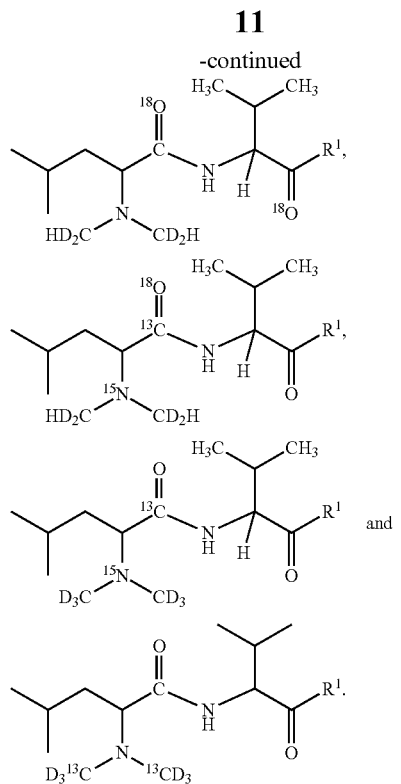

In one embodiment, the compound has the formula:

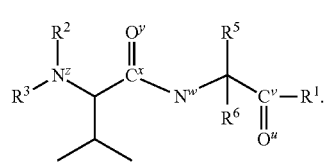

(formula 6)

In a further embodiment, R⁵ is a methyl group optionally containing one or more deuterium atoms and wherein the carbon is $^{12}C$ or $^{13}C$; R⁵ is hydrogen or deuterium; or R⁵ is a butyl group optionally containing one or more deuterium atoms and one or more $^{13}C$ atoms.

In a further embodiment, the compound is selected from:

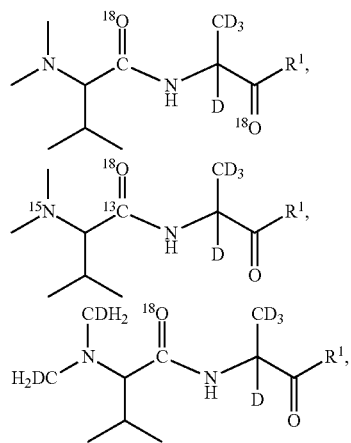

In a further embodiment, the compound is selected from:

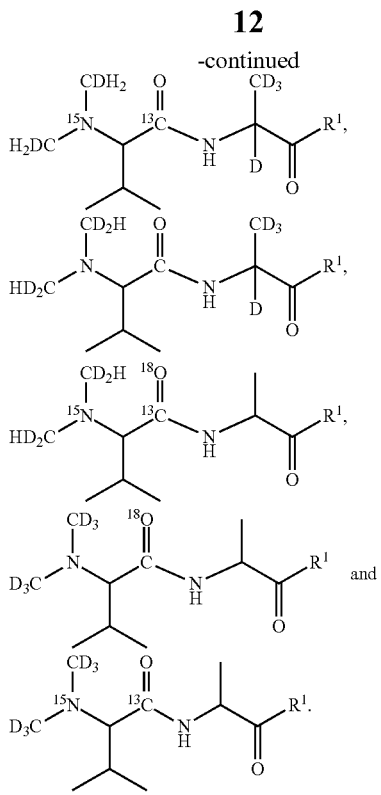

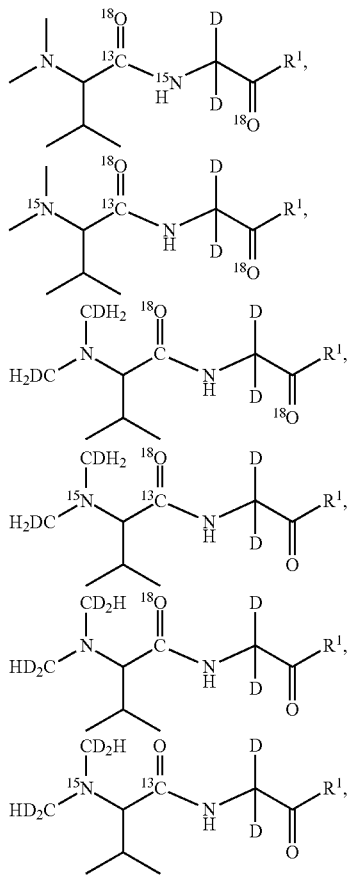

-continued
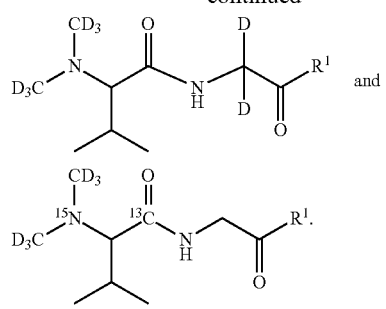
and
In a further embodiment, the compound is selected from:
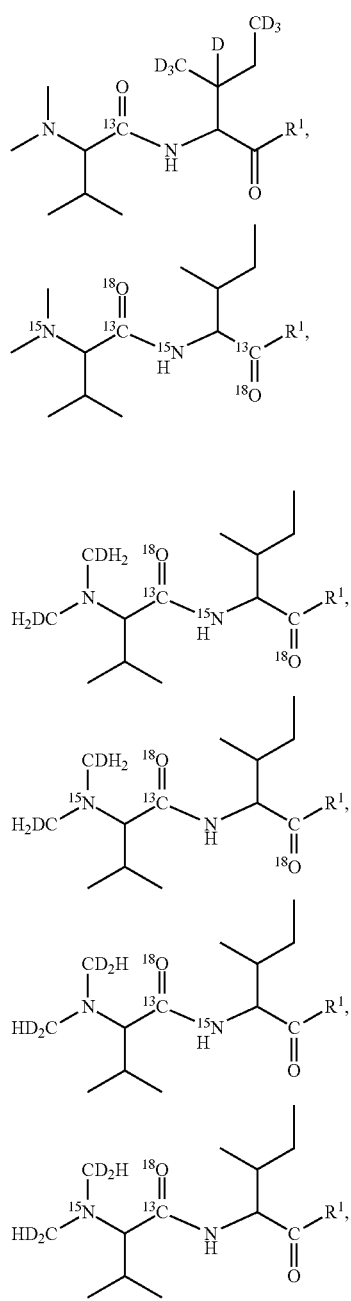
-continued
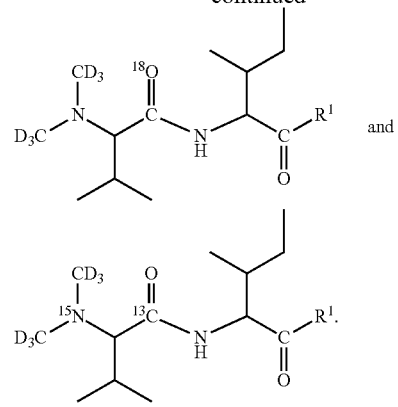
and
In a further embodiment, the compound is selected from:
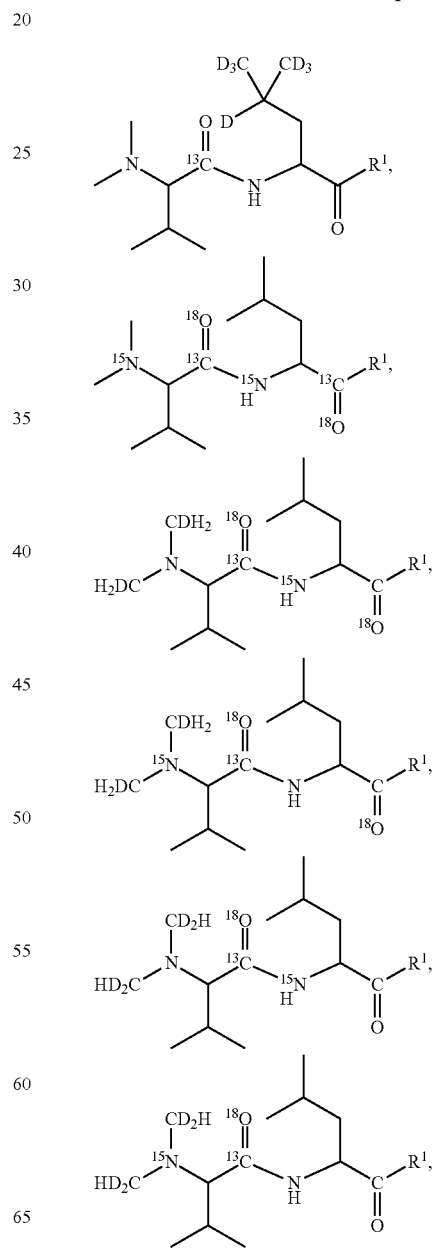

-continued

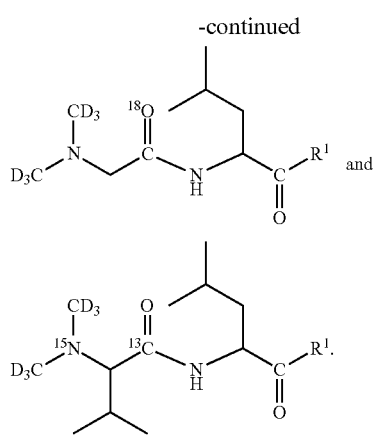
and

In one further embodiment, the compound has the formula:

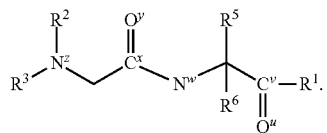
(formula 7)

In a further embodiment, $R^5$ is a methyl group optionally containing one or more deuterium atoms and wherein the carbon is $^{12}C$ or $^{13}C$; $R^5$ is an isopropyl group optionally containing one or more deuterium atoms and one or more $^{13}C$ atoms; or $R^5$ is a butyl group optionally containing one or more deuterium atoms and one or more $^{13}C$ atoms.

In a further embodiment, the compound is selected from:

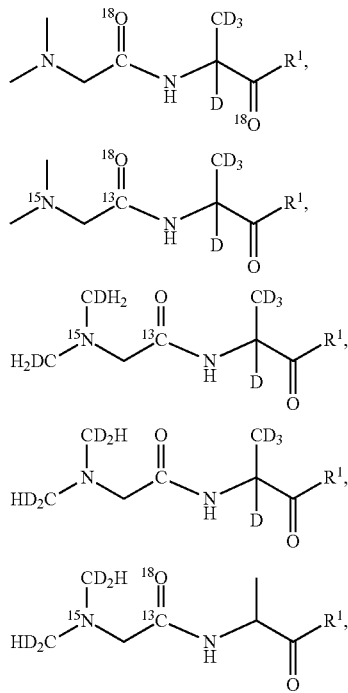

-continued

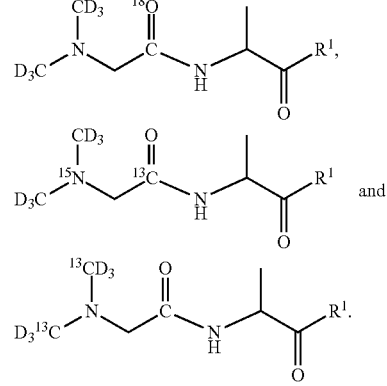
and

In a further embodiment, the compound is selected from:

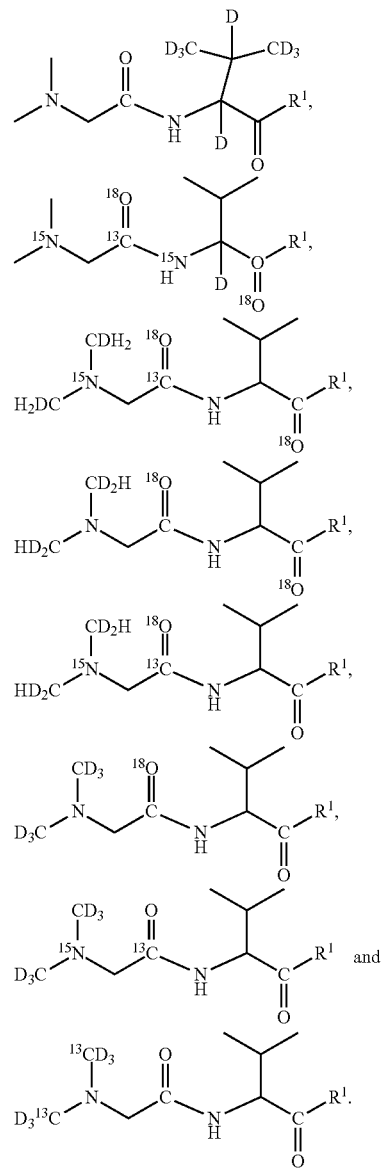

In a further embodiment, the compound is selected from:
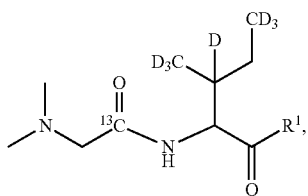
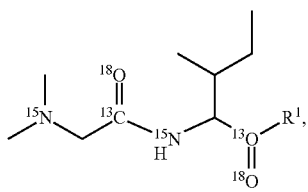
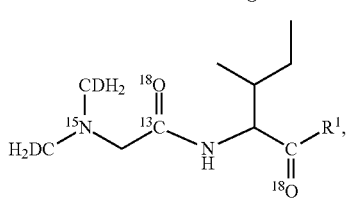
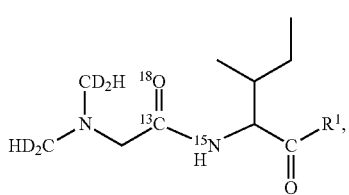
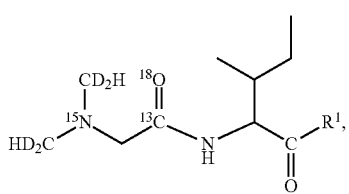
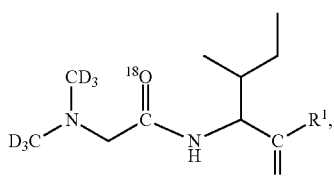
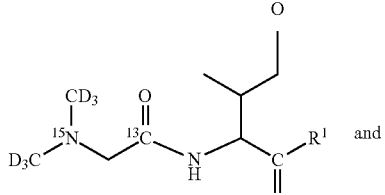
and
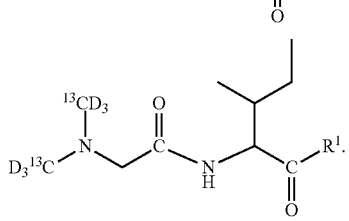
In a further embodiment, the compound is selected from:
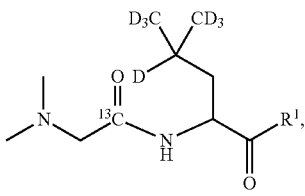
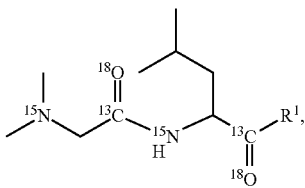
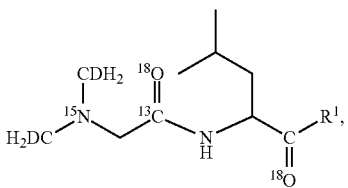
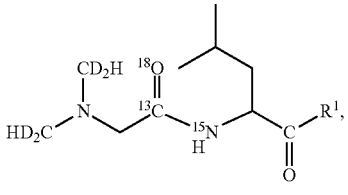
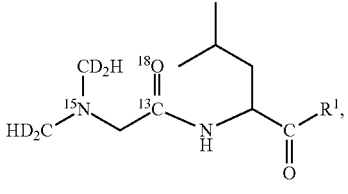
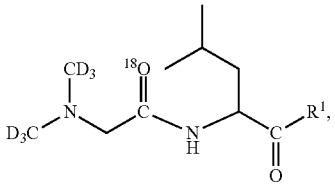
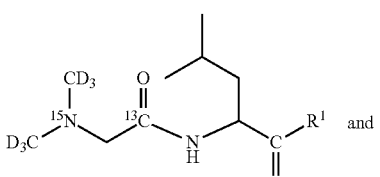
and
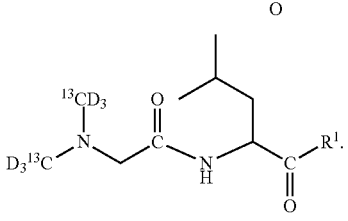

In one embodiment, the compound has the formula:

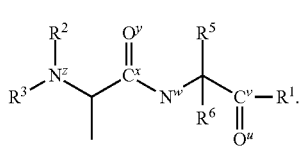

(formula 8)

In a further embodiment, $R^5$ is hydrogen or deuterium; $R^5$ is an isopropyl group optionally containing one or more deuterium atoms and one or more $^{13}C$ atoms; or $R^5$ is a butyl group optionally containing one or more deuterium atoms and one or more $^{13}C$ atoms.

In a further embodiment, the compound is selected from:

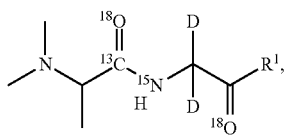

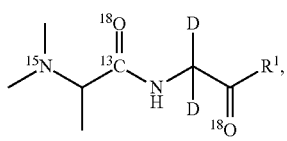

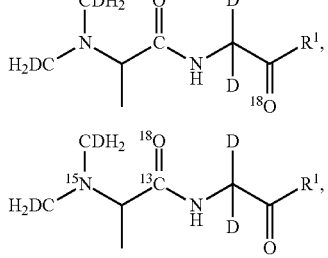

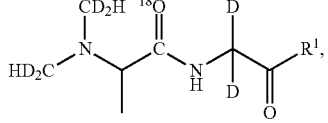

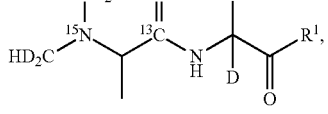

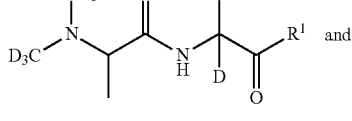

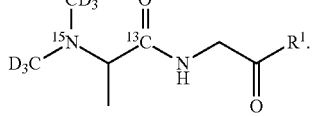

In a further embodiment, the compound is selected from:

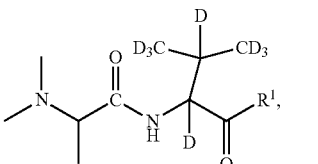

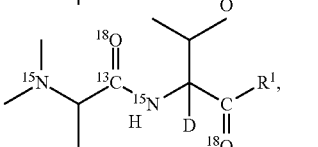

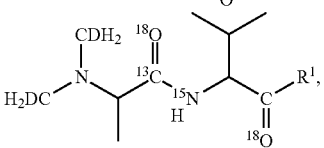

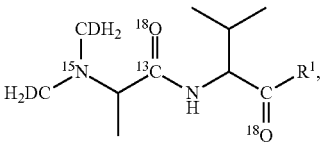

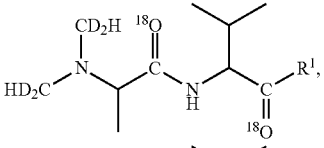

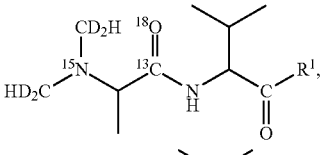

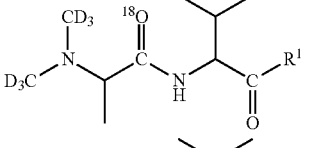

and

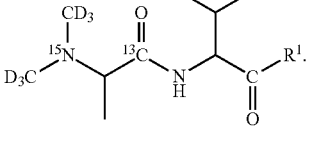

In a further embodiment, the compound is selected from:

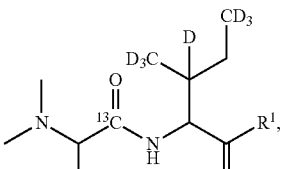

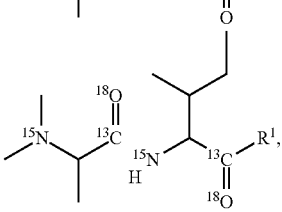

21

-continued

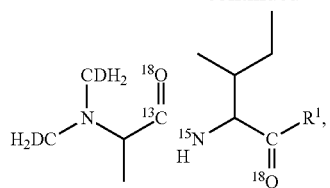

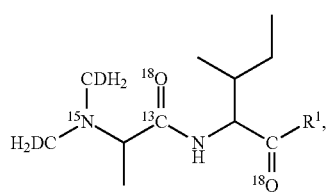

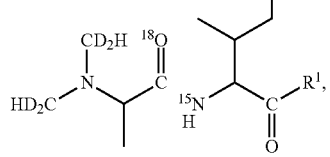

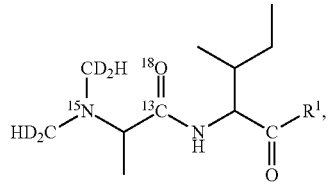

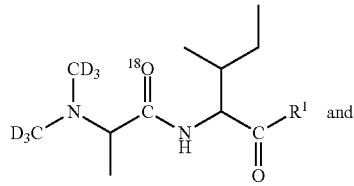

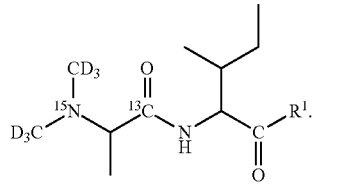

In a further embodiment, the compound is selected from:

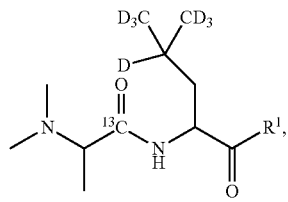

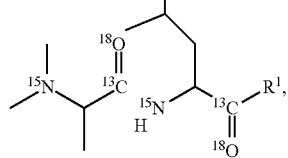

22

-continued

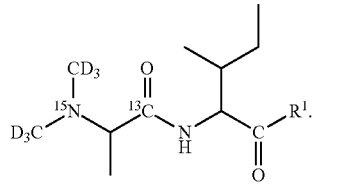

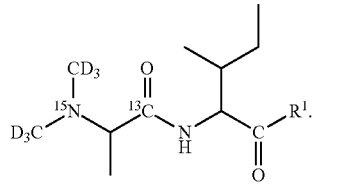

In one further embodiment, the compound as the formula:

(formula 9)

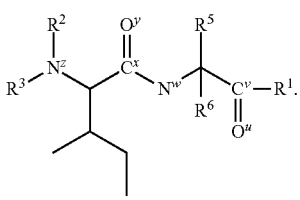

In a further embodiment, $R^5$ is hydrogen or deuterium; $R^5$ is an isopropyl group optionally containing one or more deuterium atoms and one or more $^{13}C$ atoms; or $R^5$ is a methyl group optionally containing one or more deuterium atoms and wherein the carbon is $^{12}C$ or $^{13}C$.

23
In a further embodiment, the compound is selected from:
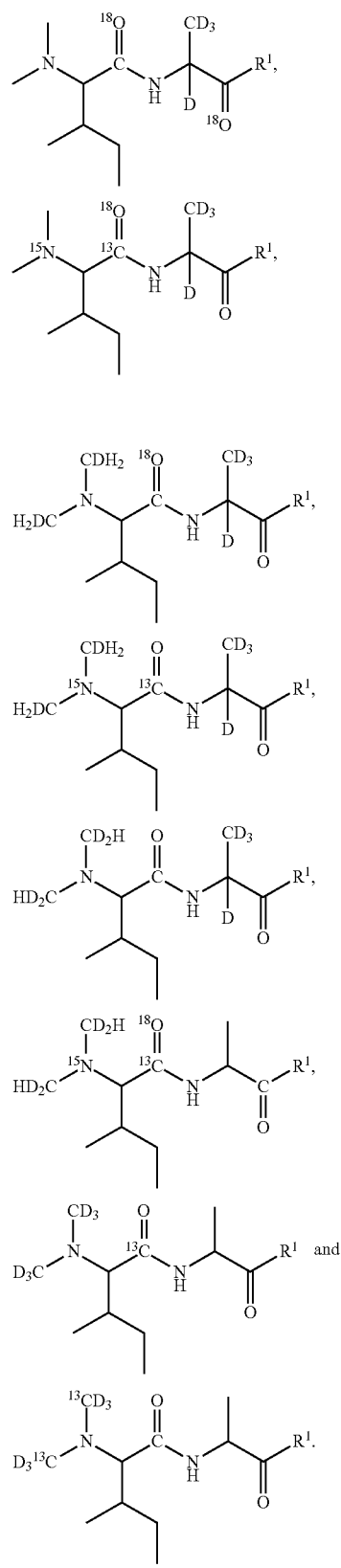
24
In a further embodiment, the compound is selected from:
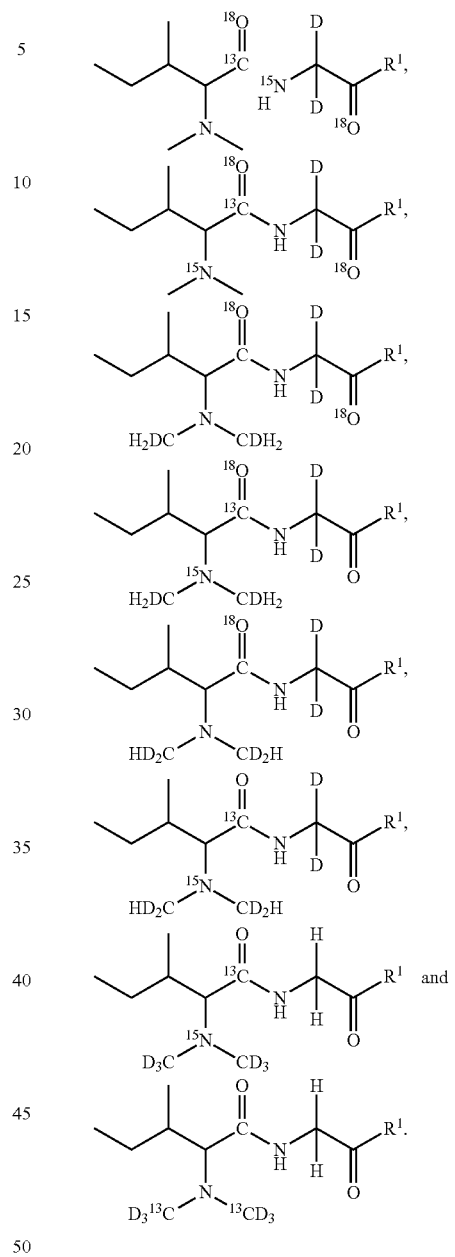
In a further embodiment, the compound is selected from:
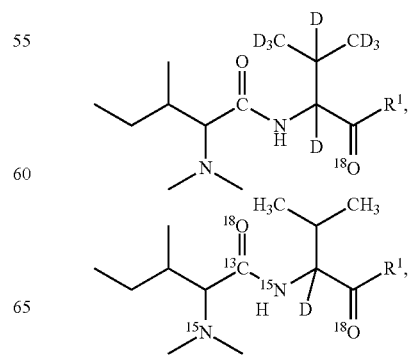

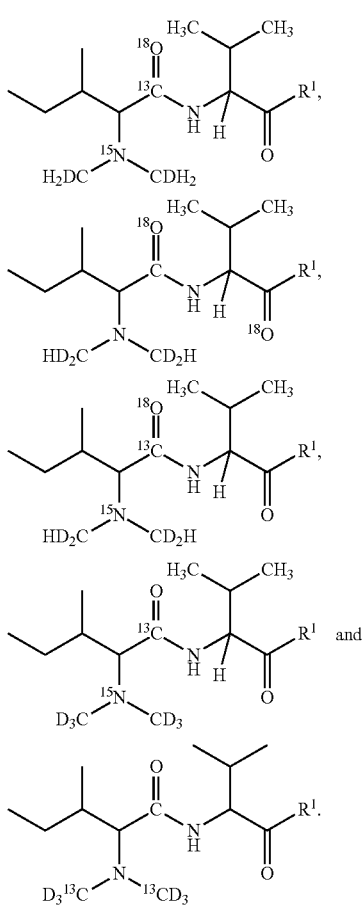

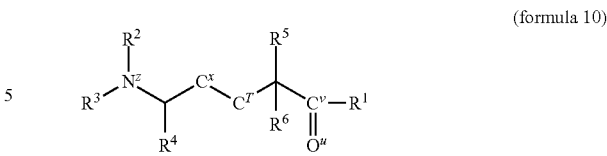

wherein
$R^1$ is an aldehyde, ketone, or carboxylic acid reactive group; $R^2$, $R^3$, $R^4$, $R^5$ and $R^6$, independently of one another, are selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein each of $R^2$, $R^3$, $R^4$ and $R^5$ optionally contain one or more $^{13}C$ atoms and one or more deuterium atoms;
$C^T$, $C^V$ and $C^x$, independently of one another, are $^{12}C$ or $^{13}C$, $O^v$ is 16O or 18O; and
$N^z$ is $^{14}N$ or $^{15}N$. Preferably, $R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$. Preferably, $R^6$ is hydrogen or deuterium. Optionally, $R^1$ comprises a hydrazide, hydrazine, amine, or oxyamine.

In one embodiment, the present invention provides a method of analyzing a mixture containing target molecules comprising the steps of: a) labeling target molecules within a first sample with a first tagging reagent, thereby generating first labeled target molecules; b) labeling target molecules within at least one additional sample with at least one additional tagging reagent, thereby generating additional labeled target molecules; c) combining the labeled target molecules of steps a) and b); d) fragmenting the combined labeled target molecules; and e) analyzing the fragments of the labeled target molecules. The fragments can be analyzed using mass spectrometry. Preferably, the fragmenting step generates immonium ions from the labeled target molecules. Additional tagging reagents having the same mass can be used to label molecules in additional samples. The different samples are optionally combined and the relative amounts of the tagged molecules compared. One of the samples may be a glycosylated protein or molecule present in known amount, allowing the quantitative amounts of target molecules from the other samples to be determined.

A further embodiment comprises labeling target molecules within at least two additional samples with at least two additional tagging reagents; labeling target molecules within at least three additional samples with at least three additional tagging reagents; labeling target molecules within at least four additional samples with at least four additional tagging reagents; labeling target molecules within at least five additional samples with at least five additional tagging reagents; labeling target molecules within at least six additional samples with at least six additional tagging reagents; labeling target molecules within at least seven additional samples with at least seven additional tagging reagents; and labeling target molecules within at least eight additional samples with at least eight additional tagging reagents.

The present invention provides 8-plex, 12-plex, and 16-plex tagging reagents able to produce reporter ions that differ by at least one Dalton from one another. Additionally, these tagging reagents can be used to provide 4-plex, 8-plex, and 12-plex tagging reagents whose reporter ions differ by two or more Daltons from one another. In a further embodiment, the generated immonium ions of each tagging reagent In the above embodiments, $R^2$, $R^3$, $R^4$, $R^5$, $R^6$, $C^x$, $C^v$, $O^y$, $O^U$, $N^z$ and $N^W$ are selected so that the mass of the reporter group and balancing group for each tagging reagent applied to a mixture are different while the overall mass of the tagging reagent remains the same. In one embodiment, $R^2$ and $R^3$ are $CDH_2$, $CD_2H$ or $CD_3$. In a further embodiment, $R^2$ and $R^3$ are $CDH_2$, $N^z$ is $^{15}N$, and $C^x$ is $^{13}C$. In a further embodiment, $R^2$ and $R^3$ are $CDH_2$ and $O^y$ is $^{18}O$. In a further embodiment, $N^z$ is $^{15}N$, $C^x$ is $^{13}C$, and $O^y$ is $^{18}O$.

While it is preferable for the balancing group of the tagging reagents to contain an amino acid as described above, it is also possible to provide tagging reagents that use other balancing groups as long as the balancing group provides sufficient atoms able to be isotopically labeled in order to balance the isotopes in the reporter group and provide the same aggregate mass for each of the tagging reagents. One embodiment of the invention provides methods of labeling target molecules using a tagging reagent having the formula:

have a mass that differs from any of the other tagging reagents by two or more Daltons.

In a further embodiment, each tagging reagent comprises a reporter group, an aldehyde, ketone, or carboxylic acid reactive group, and a based balancing group located between the reporter group and the aldehyde, ketone, or carboxylic acid reactive group. One or more atoms in the reporter group, balancing group, or both, are isotopically heavy versions of the atom. The reporter group of each tagging reagent has a mass different than the reporter groups of the other tagging reagents, the balancing group of each tagging reagent has a mass different than the balancing groups of other tagging reagents, and the aggregate mass of the reporter groups plus the balancing group for each tagging reagent is the same.

In an embodiment, the balancing group of each tagging reagent has the formula:

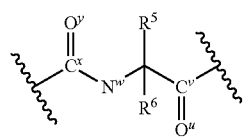

(formula 11)

wherein $R^5$ and $R^6$, independently from one another, are selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein each of $R^5$ and $R^6$ optionally contains one or more $^{13}C$ atoms and one or more deuterium atoms; $C^V$ and $C^x$, independently of one another, are $^{12}C$ or $^{13}C$, $O^U$ and $O^y$, independently of one another, are $^{16}O$ or $^{18}O$; and $N^W$ is $^{14}N$ or $^{15}N$. Preferably, $R^6$ is hydrogen or deuterium.

Preferably, $R^5$ is selected from the group consisting of hydrogen, deuterium, branched and unbranched $C_1$ to $C_8$ alkyl groups, $C_1$ to $C_8$ cycloalkyl groups, $C_1$ to $C_8$ alkenyl groups, $C_1$ to $C_8$ cycloalkenyl groups, $C_6$ to $C_{12}$ aryl groups and $C_6$ to $C_{12}$ arylalkyl groups. In one embodiment, $R^5$ is selected from the group consisting of hydrogen, deuterium, branched and unbranched $C_1$ to $C_4$ alkyl groups, $C_1$ to $C_4$ cycloalkyl groups, and $C_2$ to $C_4$ alkenyl groups.

In an embodiment, the balancing group is an "amino acid based balancing group", which means that the balancing group comprises an amino acid, where the carboxyl group forms a bond with the aldehyde, ketone, or carboxylic acid reactive group or the target molecule, and the N-terminus forms a peptide bond with a second amino acid. The carbonyl group of the second amino acid will also be part of the balancing group.

In an embodiment, the reporter group of each tagging reagent has the formula:

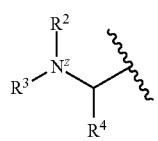

(formula 12)

$R^2$, $R^3$ and $R^4$, independently of one another, are selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein each of $R^2$, $R^3$ and $R^4$ optionally contains one or more $^{13}C$ atoms and one or more deuterium atoms; and $N^z$ is $^{14}N$ or $^{15}N$. In a further embodiment, $R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$. In a further embodiment, at least one of $R^2$ or $R^3$ contains a deuterium atom, and $N^z$ is $^{15}$ or $N^W$ is $^{15}N$.

Preferably, $R^4$ is selected from the group consisting of branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_6$ to $C_{18}$ aryl groups and $C_6$ to $C_{18}$ arylalkyl groups. In one embodiment, $R^4$ is selected from the group consisting of branched and unbranched $C_1$ to $C_3$ alkyl groups, $C_1$ to $C_3$ cycloalkyl groups, and $C_2$ to $C_3$ alkenyl groups. Preferably, at least one of $R^2$ or $R^3$ contains a deuterium atom, $N^z$ is $^{15}N$, or $N^W$ is $^{15}N$.

In an embodiment, the reporter group is an "N,N-dimethylated amino acid based reporter group", which means that the reporter group comprises an N,N-dimethylated amino acid with the exception that the carbonyl group of the amino acid will not form part of the reporter group.

The aldehyde, ketone, or carboxylic acid reactive group of each tagging reagent can be any functional group able to react with an aldehyde, ketone, or carboxylic acid group of a molecule, such as a glycosylated peptide, thereby forming bond between the molecule and the balancing group of the tagging reagent. In an embodiment, the aldehyde, ketone, or carboxylic acid reactive group is an aminooxy group or is —HNNH$_2$. In an embodiment, the aldehyde, ketone, or carboxylic acid reactive group is a hydrazide, hydrazine, amine, or oxyamine.

In a further embodiment, the dimethylated amino acid based reporter group is selected from:

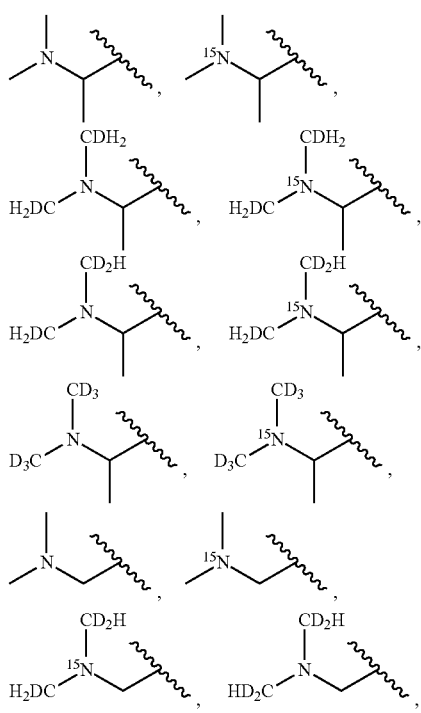

-continued
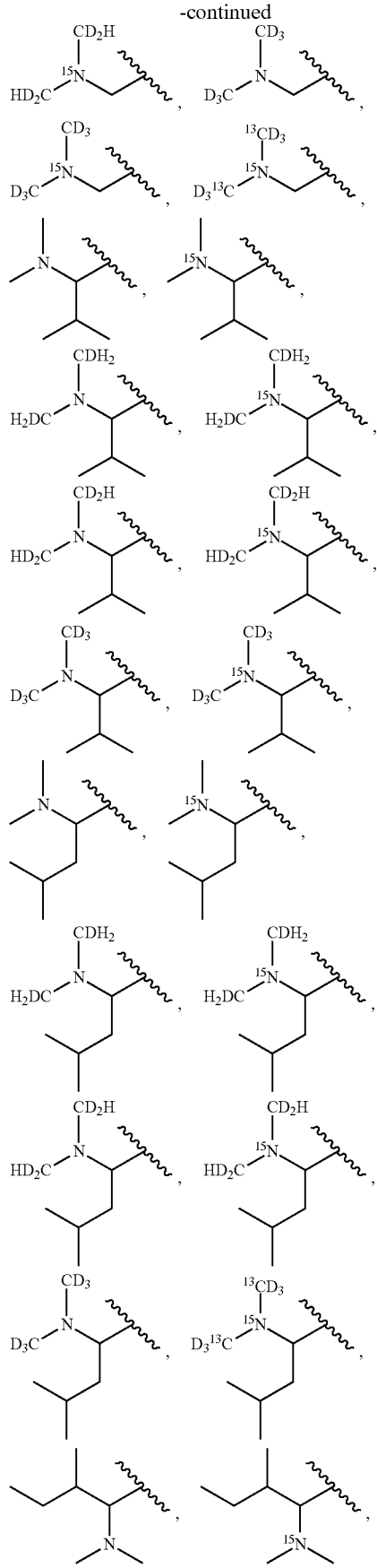
-continued
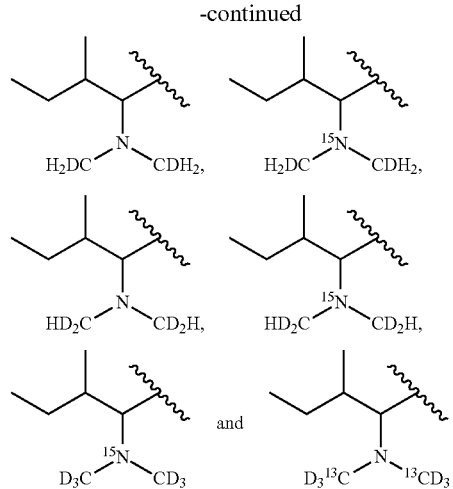
In a further embodiment, the amino acid based balancing group is selected from:
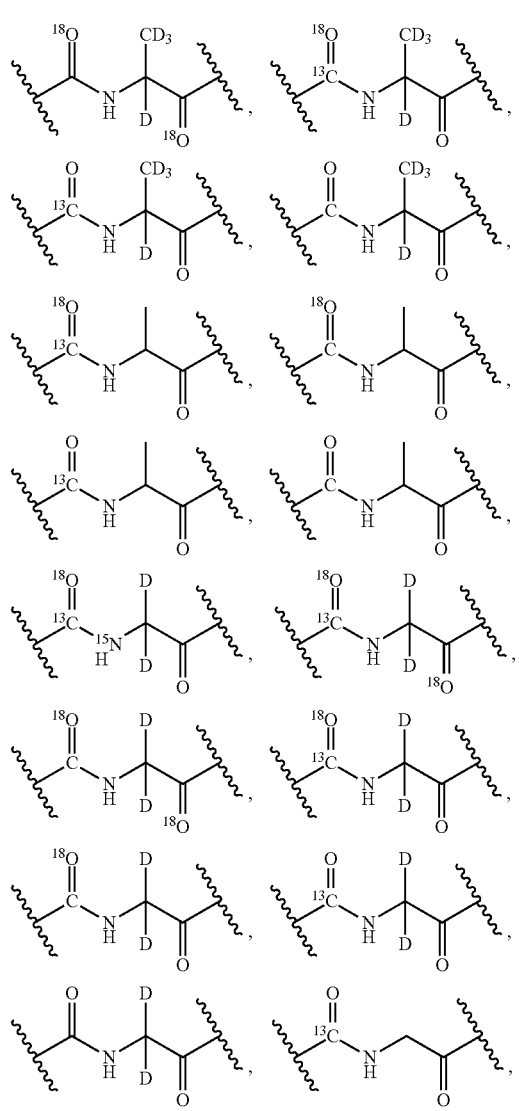

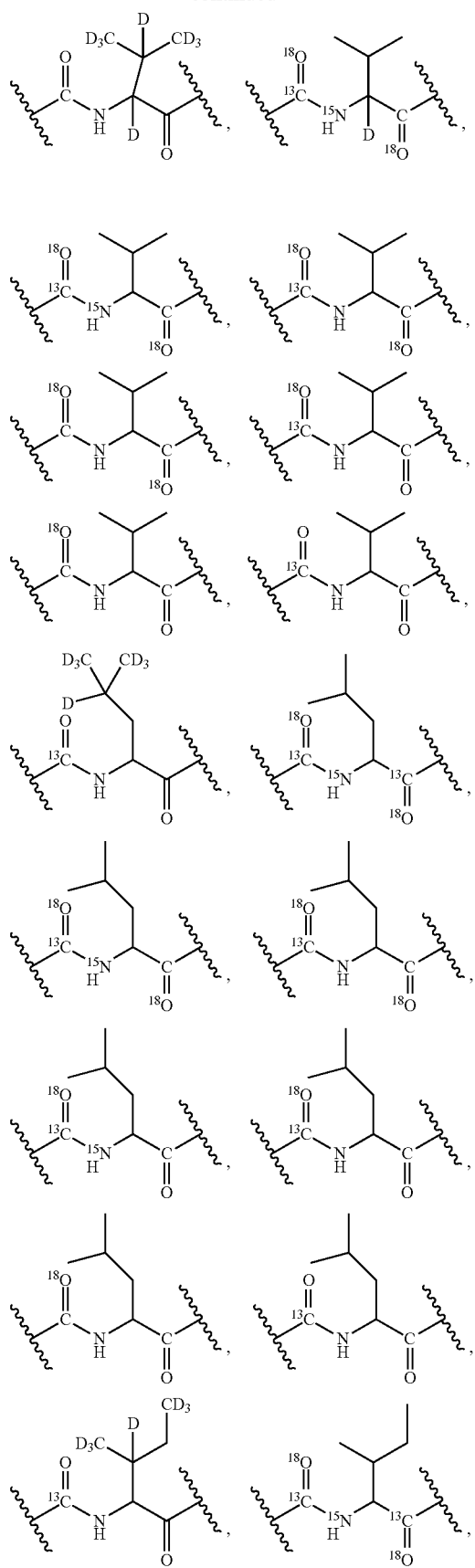

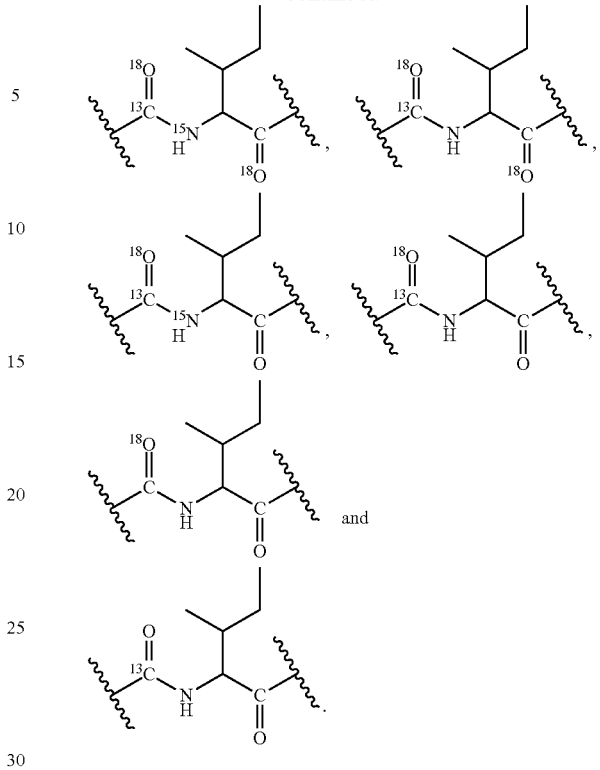

Labeling the target molecules comprises the step of reacting the aldehyde, ketone, or carboxylic acid reactive group of the tagging reagents with an aldehyde, ketone, or carboxylic acid group of the target molecule.

Methods of Analyzing a Mixture Using 16-Plex Tagging Reagents

The tagging reagents of the present invention also allow samples to be labeled with up to 16 tagging reagents, where each of the tagging reagents have the same aggregate mass but where the mass of each reporter group and balancing group are different. Where the tagging reagents comprise two amino acids as described above, these 16-plex reagents are easily produced by swapping the amino acid of the balancing group with the amino acid of the reporter group. Because the same amino acids are used in the tagging reagent, the overall mass will remain the same. However, the mass of the reporter group, and its different isotopic variations, will be different because the reporter group has now been changed. This requires that the two amino acids used in the tagging reagents be different and that the two amino acids have different masses.

For example, an 8-plex series of tagging reagents can comprise N,N-dimethyl leucine (which will make up the reporter group) and alanine (which will make up the balancing group) as depicted in Scheme 3 below. This series of tagging reagents can be expanded to a 16-plex series by using tagging reagents that have switched the alanine and leucine amino acids resulting in a reporter group made from the N,N-dimethyl alanine and a balancing group made from leucine. The overall masses of the tagging reagents are the same, but the mass of the different reporter groups will be different for each 16-plex reagent.

Scheme 3

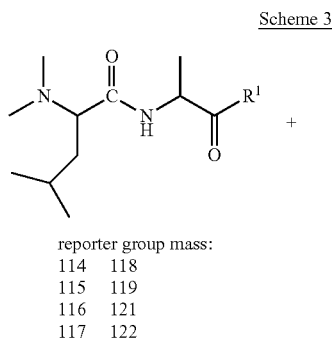

reporter group mass:
114   118
115   119
116   121
117   122

+

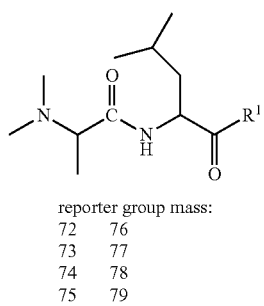

reporter group mass:
72   76
73   77
74   78
75   79

Accordingly, one embodiment of the present invention provides a method of analyzing a mixture containing target molecules comprising the steps of:

a) labeling target molecules within a first sample with a first tagging reagent, thereby generating first labeled target molecules, wherein the first tagging reagent has the formula:

$(CH_3)_2\text{-}AA^1\text{-}AA^2\text{-}R^1$   (formula 3)

where $R^1$ is an aldehyde, ketone, or carboxylic acid reactive group; $AA^1$ is a first amino acid having an N-terminus; $AA^2$ is a second amino acid having an N-terminus; and the two $CH_3$ groups are attached to the N-terminus of $AA^1$;

b) labeling target molecules within one or more additional samples with one or more additional tagging reagents, thereby generating additional labeled target molecules, wherein at least one of the additional tagging reagents has the formula:

$(CH_3)_2\text{-}AA^2\text{-}AA^1\text{-}R^1$   (formula 4)

where $AA^1$ and $AA^2$ in the additional tagging reagent are the same amino acids as in the first tagging reagent with the exception that the amino acids may contain different isotopes; and the two $CH_3$ groups are attached to the N-terminus of $AA^2$ in the additional tagging reagent;

c) combining the labeled target molecules of steps a) and b);

d) fragmenting the combined labeled target molecules; and e) analyzing the fragments of the labeled molecules.

In a further embodiment, $AA^1$ and $AA^2$, independently from one another, are any natural or synthetic amino acid with the provision that $AA^1$ and $AA^2$ cannot be the same amino acid. $AA^1$ and $AA^2$ also cannot have the same mass. Preferably, the amino acid is a natural amino acid selected from the group consisting of leucine, isoleucine, alanine, glycine, valine, histidine, phenylalanine, tryptophan, lysine and tyrosine. Even more preferably, the natural amino acid is selected from the group consisting of leucine, isoleucine, alanine, glycine and valine. Alternatively, $AA^1$, $AA^2$, or both, are unnatural, non-standard or synthetic amino acids including, but not limited to, β amino acids, norleucine, norvaline, 2-aminobutylric acid, 3-aminoisobutylric acid, and 3-aminobutylric acid.

Each tagging reagent comprises a reporter group, an aldehyde, ketone, or carboxylic acid reactive group, and a balancing group located between the reporter group and aldehyde, ketone, or carboxylic acid reactive group, wherein one or more atoms in the reporter group, balancing group, or both, are heavy isotope versions of the atom. The reporter group of each tagging reagent has a mass different than the reporter groups of the other tagging reagents, the balancing group of each tagging reagent has a mass different than the balancing groups of other tagging reagents, and the aggregate mass of the reporter group plus the balancing group for each tagging reagent is the same.

Each tagging reagent is able to generate an immonium ion during the fragmentation step. This method allows for anywhere between 2 to 16 samples to be labeled with 2 to 16 tagging reagents. In one embodiment, 2 to 8 samples are labeled wherein the generated reporter ions from each tagging reagent has a mass that differs from the generated reporter ions from the other tagging reagents by two or more Daltons.

In a further embodiment, the balancing group of the 16-plex tagging reagents has the formula:

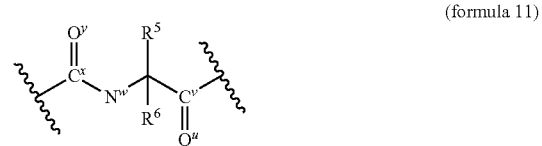

(formula 11)

wherein $R^5$ and $R^6$, independently from one another, are selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein each of $R^5$ and $R^6$ optionally contains one or more $^{13}C$ atoms and one or more deuterium atoms; $C^V$ and $C^x$, independently of one another, are $^{12}C$ or $^{13}C$; $O^U$ and $O^v$, independently of one another, are $^{16}O$ or $^{18}O$; $N^W$ is $^{14}N$ or $^{15}N$. Preferably, $R^6$ is hydrogen or deuterium.

Preferably, $R^5$ is selected from the group consisting of hydrogen, deuterium, branched and unbranched $C_1$ to $C_8$ alkyl groups, $C_1$ to $C_8$ cycloalkyl groups, $C_1$ to $C_8$ alkenyl groups, $C_1$ to $C_8$ cycloalkenyl groups, $C_6$ to $C_{12}$ aryl groups and $C_6$ to $C_{12}$ arylalkyl groups. In one embodiment, $R^5$ is selected from the group consisting of hydrogen, deuterium, branched and unbranched $C_1$ to $C_4$ alkyl groups, $C_1$ to $C_4$ cycloalkyl groups, and $C_2$ to $C_4$ alkenyl groups.

In a further embodiment, the reporter group of the 16-plex tagging reagents has the formula:

(formula 12)

In a further embodiment, $R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$. In a further embodiment, at least one of $R^2$ or $R^3$ contains a deuterium atom, and $N^z$ is $^{15}$ or $N^W$ is $^{15}N$.

Preferably, $R^4$ is selected from the group consisting of branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_6$ to $C_{18}$ aryl groups and $C_6$ to $C_{18}$ arylalkyl groups. In one embodiment, $R^4$ is selected from the group consisting of branched and unbranched $C_1$ to $C_3$ alkyl groups, $C_1$ to $C_3$ cycloalkyl groups, and $C_2$ to $C_3$ alkenyl groups. Preferably, at least one of $R^2$ or $R^3$ contains a deuterium atom, $N^z$ is $^{15}N$, or $N^W$ is $^{15}N$.

A further embodiment comprises labeling target molecules with from 2 to 8 tagging reagents having the formula $(CH_3)_2$-$AA^1$-$AA^2$-$R^1$. A further embodiment comprises labeling target molecules with from 2 to 8 tagging reagents having the formula $(CH_3)_2$-$AA^2$-$AA^1$-$R^1$.

In a further embodiment, $AA^1$ is leucine and $AA^2$ is selected from the group consisting of alanine, glycine and valine.

In a further embodiment, $AA^1$ is isoleucine and $AA^2$ is selected from the group consisting of alanine, glycine and valine.

In a further embodiment, $AA^1$ is alanine and $AA^2$ is selected from the group consisting of leucine, isoleucine, glycine and valine.

In a further embodiment, $AA^1$ is glycine and $AA^2$ is selected from the group consisting of leucine, isoleucine, alanine and valine.

In a further embodiment, $AA^1$ is valine and $AA^2$ is selected from the group consisting of leucine, isoleucine, glycine and alanine.

In some instances, switching the amino acid positions may result in different ionization efficiency during fragmentation, different elution time, and different reporter ion yields. Accordingly, it may be beneficial to introduce means for correcting or normalizing the differences caused by the switching of the amino acid positions in the tagging reagents. For example, the same amount of a standard could be added to each sample, and/or the samples could be labeled with a different tagging system. A correction factor can then be generated from MS analysis of these samples by comparing the different signal response of the same standard compound in different samples.

Tagging Reagent Compounds and Kits

In one embodiment, the present invention provides mass spectrometry tagging reagents comprising a compound having the formula of:

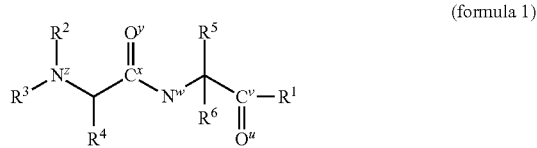

(formula 1)

$R^2$, $R^3$, $R^4$, $R^5$ and $R^6$, independently of one another, are selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein each of $R^2$, $R^3$, $R^4$, $R^5$ and $R^6$ optionally contain one or more $^{13}C$ atoms and one or more deuterium atoms; $C^V$ and $C^x$, independently of one another, are $^{12}C$ or $^{13}C$; $O^U$ and $O^V$, independently of one another, are $^{16}O$ or $^{18}O$; and $N^z$ and $N^W$, independently of one another, are $^{14}N$ or $^{15}N$. In a further embodiment, $R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$. In a further embodiment, $R^6$ is hydrogen or deuterium. Preferably at least one of $R^2$ or $R^3$ contains a deuterium atom, $N^z$ is $^{15}N$, or $N^W$ is $^{15}N$. Preferably these tagging reagents are able to generate an immonium ion during fragmentation.

Preferably, $R^4$ and $R^5$ are selected from the group consisting of hydrogen, deuterium, branched and unbranched $C_1$ to $C_8$ alkyl groups, $C_1$ to $C_8$ cycloalkyl groups, $C_1$ to $C_8$ alkenyl groups, $C_1$ to $C_8$ cycloalkenyl groups, $C_6$ to $C_{012}$ aryl groups and $C_6$ to $C_{12}$ arylalkyl groups. In one embodiment, $R^4$ and $R^5$ are selected from the group consisting of hydrogen, deuterium, branched and unbranched $C_1$ to $C_4$ alkyl groups, $C_1$ to $C_4$ cycloalkyl groups, and $C_2$ to $C_4$ alkenyl groups.

In a further embodiment, the tagging reagent comprises a compound having the formula:

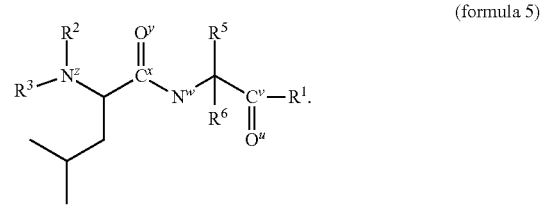

(formula 5)

where $R^5$ is selected from the group consisting of: a methyl group optionally containing one or more deuterium atoms and wherein the carbon is $^{12}C$ or $^{13}C$; hydrogen; deuterium; and an isopropyl group optionally containing one or more deuterium atoms and one or more $^{13}C$ atoms.

In a further embodiment, the tagging reagent comprises a compound having the formula:

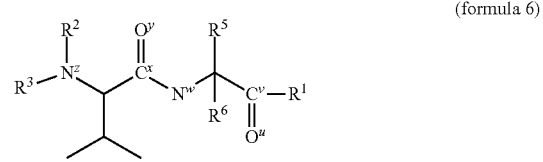

(formula 6)

where $R^5$ is selected from the group consisting of: a methyl group optionally containing one or more deuterium atoms and wherein the carbon is $^{12}C$ or $^{13}C$; hydrogen; deuterium; and a butyl group optionally containing one or more deuterium atoms and one or more $^{13}C$ atoms.

In a further embodiment, the tagging reagent comprises a compound having the formula:

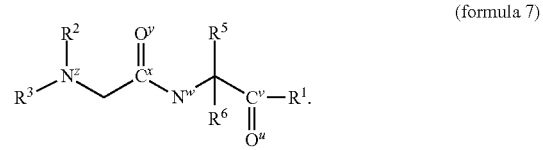

(formula 7)

where $R^5$ is selected from the group consisting of: a methyl group optionally containing one or more deuterium atoms and wherein the carbon is $^{12}C$ or $^{13}C$; an isopropyl group optionally containing one or more deuterium atoms and one or more $^{13}$C atoms; and a butyl group optionally containing one or more deuterium atoms and one or more $^{13}$C atoms.

In a further embodiment, the tagging reagent comprises a compound having the formula:

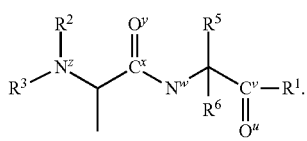

(formula 8)

where $R^5$ is selected from the group consisting of: hydrogen; deuterium; an isopropyl group optionally containing one or more deuterium atoms and one or more $^{13}$C atoms; and a butyl group optionally containing one or more deuterium atoms and one or more 13C atoms.

In a further embodiment, the tagging reagent comprises a compound having the formula:

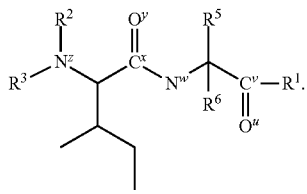

(formula 9)

where $R^5$ is selected from the group consisting of: a methyl group optionally containing one or more deuterium atoms and wherein the carbon is $^{12}$C or $^{13}$C; hydrogen; deuterium; and an isopropyl group optionally containing one or more deuterium atoms and one or more $^{13}$C atoms.

The present invention also provides a kit comprising two or more tagging reagents, wherein each tagging reagent comprises a reporter group, an aldehyde, ketone, or carboxylic acid reactive group, and a balancing group located between the reporter group and aldehyde, ketone, or carboxylic acid reactive group, wherein one or more atoms in the reporter group, balancing group, or both, are isotopically heavy versions of the atom; and wherein the reporter group of each tagging reagent has a mass different than the reporter groups of the other tagging reagents, the balancing group of each tagging reagent has a mass different than the balancing groups of other tagging reagents, and the aggregate mass of the reporter group plus the balancing group for each tagging reagent is the same. Preferably, the tagging reagents are able to generate an immonium ion.

In an embodiment, the balancing group of each tagging reagent has the formula:

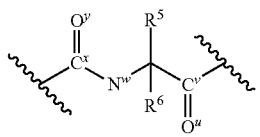

(formula 11)

wherein $R^5$ and $R^6$, independently from one another, are selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein each of $R^5$ and $R^6$ optionally contains one or more $^{13}$C atoms and one or more deuterium atoms; $C^V$ and $C^x$, independently of one another, are $^{12}$C or $^{13}$C, $O^U$ and $O^v$, independently of one another, are $^{16}$O or $^{18}$O; and $N^W$ is $^{14}$N or $^{15}$N. In a further embodiment, $R^6$ is hydrogen or deuterium.

Preferably, $R^5$ is selected from the group consisting of hydrogen, deuterium, branched and unbranched $C_1$ to $C_8$ alkyl groups, $C_1$ to $C_8$ cycloalkyl groups, $C_1$ to $C_8$ alkenyl groups, $C_1$ to $C_8$ cycloalkenyl groups, $C_6$ to $C_{12}$ aryl groups and $C_6$ to $C_{12}$ arylalkyl groups. In one embodiment, $R^5$ is selected from the group consisting of hydrogen, deuterium, branched and unbranched $C_1$ to $C_4$ alkyl groups, $C_1$ to $C_4$ cycloalkyl groups, and $C_2$ to $C_4$ alkenyl groups.

The reporter group of each tagging reagent has the formula:

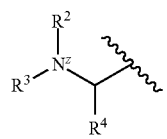

(formula 12)

wherein $R^2$, $R^3$ and $R^4$, independently of one another, are selected from the group consisting of hydrogen, deuterium, branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_4$ to $C_{12}$ aryl groups and $C_4$ to $C_{12}$ arylalkyl groups, wherein each of $R^2$, $R^3$ and $R^4$ optionally contains one or more $^{13}$C atoms and one or more deuterium atoms; and $N^z$ is $^{14}$N or $^{15}$N. In a further embodiment, $R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$. In a further embodiment, at least one of $R^2$ or $R^3$ contains a deuterium atom, $N^z$ is $^{15}$N, or $N^W$ is $^{15}$N.

Preferably, $R^4$ is selected from the group consisting of branched and unbranched $C_1$ to $C_{12}$ alkyl groups, $C_1$ to $C_{12}$ cycloalkyl groups, $C_1$ to $C_{12}$ alkenyl groups, $C_1$ to $C_{12}$ cycloalkenyl groups, $C_6$ to $C_{18}$ aryl groups and $C_6$ to $C_{18}$ arylalkyl groups. In one embodiment, $R^4$ is selected from the group consisting of branched and unbranched $C_1$ to $C_3$ alkyl groups, $C_1$ to $C_3$ cycloalkyl groups, and $C_2$ to $C_3$ alkenyl groups. Preferably, at least one of $R^2$ or $R^3$ contains a deuterium atom, $N^z$ is $^{15}$N, or $N^W$ is $^{15}$N.

The aldehyde, ketone, or carboxylic acid reactive group of each tagging reagent can be any functional group able to react with an amine group of a peptide or small molecule, thereby forming bond between the peptide and the balancing group of the tagging reagent. In one embodiment, the aldehyde, ketone, or carboxylic acid reactive group is an aminooxy group or is —HNNH$_2$.

In one embodiment, the reporter groups of the tagging reagents of the present invention are derived from natural amino acids where the amino group in the amino acid which makes up the reporter group has been dimethylated.

The present invention also provides a kit where at least one tagging reagent has the formula:

(CH$_3$)$_2$-AA$^1$-AA$^2$-R$^1$     (formula 3)

where $R^1$ is an aldehyde, ketone, or carboxylic acid reactive group; AA$^1$ is a first amino acid having an N-terminus; AA$^2$ is a second amino acid having an N-terminus; and the two CH$_3$ groups are attached to the N-terminus of AA$^1$; and wherein at least one tagging reagent has the formula:

(CH$_3$)$_2$-AA$^2$-AA$^1$-R$^1$     (formula 4)

where $AA^1$ and $AA^2$ are the same amino acids as in the first tagging reagent with the exception that the amino acids may contain different isotopes; and the two $CH_3$ groups are attached to the N-terminus of $AA^2$;

$AA^1$ and $AA^2$, independently from one another, are any amino acid, preferably a natural amino acid, with the provision that $AA^1$ and $AA^2$ cannot be the same amino acid or have the same mass. Preferably, $AA^1$ and $AA^2$, independently from one another, are selected from the group consisting of leucine, isoleucine, alanine, glycine and valine.

In a further embodiment, the kit comprises 2 to 8 tagging reagents having the formula $(CH_3)_2$-$AA^1$-$AA^2$-$R^1$. In another embodiment, the kit comprises 2 to 8 tagging reagents having the formula $(CH_3)_2$-$AA^2$-$AA^1$-$R^1$.

In one embodiment, the kit comprises two or more tagging reagents, three or more tagging reagents, four or more tagging reagents, five or more tagging reagents, six or more tagging reagents, seven or more tagging reagents, eight or more tagging reagents, nine or more tagging reagents, ten or more tagging reagents, eleven or more tagging reagents, twelve or more tagging reagents, thirteen or more tagging reagents, fourteen or more tagging reagents, fifteen or more tagging reagents, or sixteen or more tagging reagents.

The tagging reagents disclosed herein serve as attractive alternatives for isobaric tag for relative and absolute quantitation (iTRAQ) and tandem mass tags (TMTs) due to their synthetic simplicity, labeling efficiency and improved fragmentation efficiency. Additionally, these tagging reagents are able to react with aldehyde, ketone, or carboxylic acid groups, allowing them to chemically tag glycans. The tagging reagents disclosed herein enable simultaneous quantitation of multiple glycan/glycan samples and identification based on sequence-specific fragmentation. The isobaric reagents can be synthesized in fewer steps using commercially available reagents (one step or two step synthesis), thus offering synthetic simplicity and much reduced cost as compared to other existing technology. This feature allows the routine application of these isobaric tagging reagents to many large-scale proteomic and glycomic studies. In addition to multiplexed quantitation, the reagents disclosed herein based on dimethylated amino acid tagging promote enhanced fragmentation, thus enabling more confident protein identification and superior capability for de novo sequencing. This feature makes the present invention an important tool for identifying and analyzing glycans in biological studies.

In an embodiment, the invention provides an isotopically enriched sample comprising any of the compounds disclosed herein, including the disclosed compounds having specific isotopic compositions, and methods of using an isotopically enriched sample comprising any of the compounds disclosed herein, including the disclosed compounds having specific isotopic compositions. In a specific embodiment, the invention provides an isotopically enriched sample comprising a compound of the invention having a specific isotopic composition, wherein the compound is present in an abundance that is at least 10 times greater, for some embodiments at least 100 times greater, for some embodiments at least 1,000 times greater, for some embodiments at least 10,000 times greater, than the abundance of the same compound having the same isotopic composition in a naturally occurring sample, and related methods of using these samples, for example for use as a tagging reagent in mass spectrometry. In a specific embodiment, the invention provides an isotopically enriched sample having a purity with respect to a compound of the invention having a specific isotopic composition that is substantially enriched, for example, a purity equal to or greater than 90%, in some embodiments equal to or greater than 95%, in some embodiments equal to or greater than 99%, in some embodiments equal to or greater than 99.9%, in some embodiments equal to or greater than 99.99%, and in some embodiments equal to or greater than 99.999%, and related methods of using these samples, for example for use as a tagging reagent in mass spectrometry. In a specific embodiment, the invention provides an isotopically enriched sample that has been purified with respect to a compound of the invention having a specific isotopic composition, for example using isotope purification methods known in the art, and related methods of using these samples, for example for use as a tagging reagent in mass spectrometry.

BRIEF DESCRIPTION OF THE DRAWINGS

FIG. 17, panel a, shows an unlabeled glycan released from a glycoprotein standard, bovine thyroglobulin (BTG). FIG. 17, panel b, shows partial labeling after reaction with AminoxyTMT. FIG. 17, panel c, shows complete labeling after reaction with the SUGAR tag.

DETAILED DESCRIPTION OF THE INVENTION

Definitions

Figure 1:
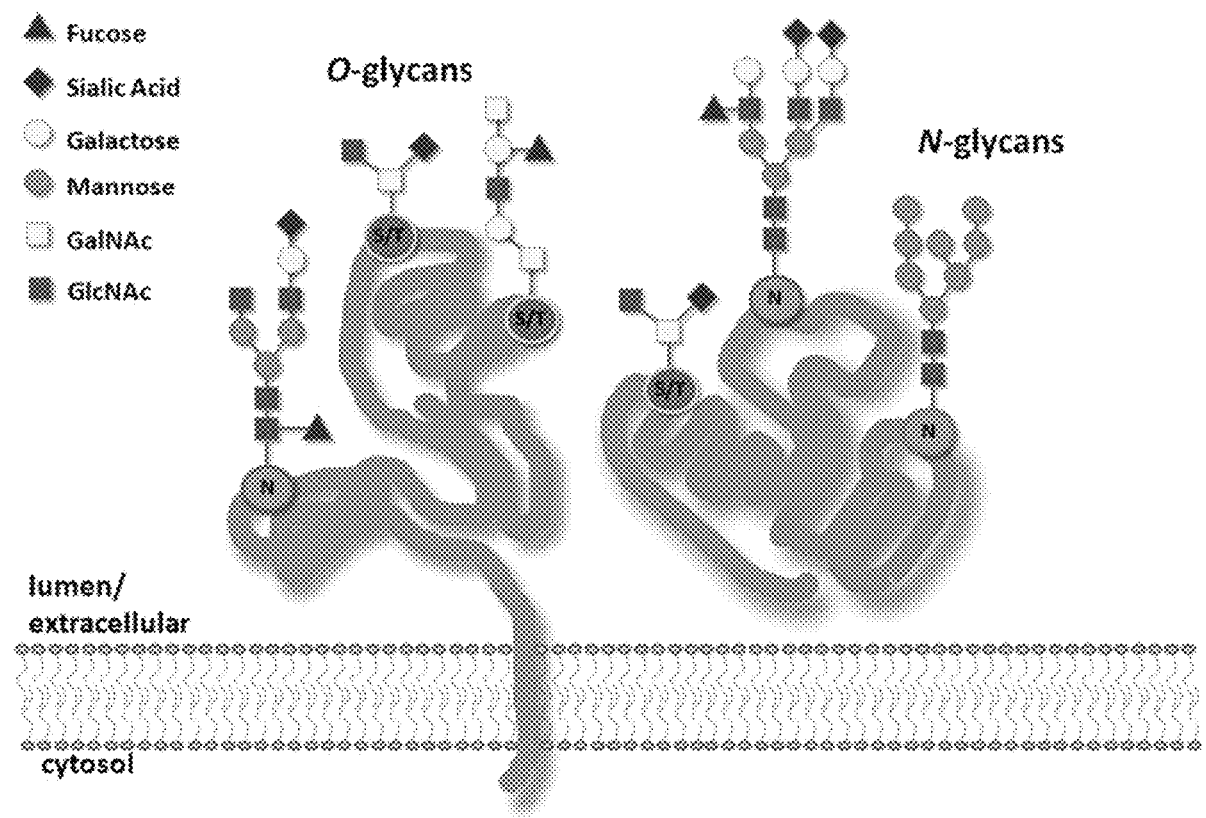
FIG. 1 illustrates different types of glycosylation of peptides, including O-glycans and N-glycans.

As used herein the terms "tagging" and "labeling" refers to reacting a reagent or compound with a molecule of interest, including but not limited to glycans and glycosylated peptides, so that one or more functional groups are attached to the molecule of interest. A "tagged" or "labeled" molecule of interest refers to a molecule of interest having the one or more functional groups attached.

"Glycosylation" refers to the process in which a carbohydrate is attached to a functional group of another molecule, such as a peptide. In particular, glycosylation includes the enzymatic process that attaches glycans to proteins, lipids, or other organic molecules. Examples of glycosylation includes the following:

N-linked glycans attached to a nitrogen of asparagine or arginine side-chains. N-linked glycosylation requires participation of a special lipid called dolichol phosphate;

O-linked glycans attached to the hydroxyl oxygen of serine, threonine, tyrosine, hydroxylysine, or hydroxyproline side-chains, or to oxygen atoms on lipids such as ceramide;

phospho-glycans linked through the phosphate of a phospho-serine;

C-linked glycans, a rare form of glycosylation where a sugar is added to a carbon on a tryptophan side-chain; and glypiation, which is the addition of a GPI anchor that links proteins to lipids through glycan linkages.

The term "glycan" is used herein interchangeably with the terms "polysaccharide" and "carbohydrate" and refers to any biologically occurring form (N- or O-linked glycans, glycolipids, glycosaminoglycans, microbial polysaccharides) each having its own chemical repertoire of presentation or modifications.

The terms "peptide" and "polypeptide" are used synonymously in the present disclosure, and refer to a class of compounds composed of amino acid residues chemically bonded together by amide bonds (or peptide bonds). Peptides are polymeric compounds comprising at least two amino acid residues or modified amino acid residues. Peptides include compositions comprising a few amino acids and include compositions comprising intact proteins or modified proteins. Modifications can be naturally occurring or non-naturally occurring, such as modifications generated by chemical synthesis. Modifications to amino acids in polypeptides include, but are not limited to, phosphorylation, glycosylation, lipidation, prenylation, sulfonation, hydroxylation, acetylation, methionine oxidation, alkylation, acylation, carbamylation, iodination and the addition of cofactors. Peptides include proteins and further include compositions generated by degradation of proteins, for example by proteolytic digestion. Peptides and polypeptides may be generated by substantially complete digestion or by partial digestion of proteins. Identifying or sequencing a peptide refers to determination of is composition, particularly its amino acid sequence, and characterization of any modifications of one or more amino acids comprising the peptide or polypeptide.

"Fragment" refers to a portion of molecule, such as a glycosylated peptide. Fragments may be singly or multiply charged ions. Fragments may be derived from bond cleavage in a parent molecule, including site specific cleavage of polypeptide bonds in a parent peptide. Fragments may also be generated from multiple cleavage events or steps. Fragments may be a truncated peptide, either carboxy-terminal, amino-terminal or both, of a parent peptide. A fragment may refer to products generated upon the cleavage of a polypeptide bond, a C—C bond, a C—N bond, a C—O bond or combination of these processes. Fragments may refer to products formed by processes whereby one or more side chains of amino acids are removed, or a modification is removed, or any combination of these processes. Fragments useful in the present invention include fragments formed under metastable conditions or result from the introduction of energy to the precursor by a variety of methods including, but not limited to, collision induced dissociation (CID), higher-energy collision dissociation (HCD), surface induced dissociation (SID), laser induced dissociation (LID), electron capture dissociation (ECD), electron transfer dissociation (ETD), ultraviolet photo-dissociation (UVPD), or any combination of these methods or any equivalents known in the art of tandem mass spectrometry. Fragments useful in the present invention also include, but are not limited to, x-type fragments, y-type fragments, z-type fragments, a-type fragments, b-type fragments, c-type fragments, internal ion (or internal cleavage ions), immonium ions or satellite ions. The types of fragments derived from a parent analyte, such as a glycosylated polypeptide analyte, often depend on the sequence of the parent, method of fragmentation, charge state of the parent precursor ion, amount of energy introduced to the parent precursor ion and method of delivering energy into the parent precursor ion. Properties of fragments, such as molecular mass, may be characterized by analysis of a fragmentation mass spectrum.

An "aldehyde, ketone, or carboxylic acid reactive group" of a tagging reagent can be any functional group able to react with an amine group of a peptide or small molecule, thereby forming bond between the peptide or small molecule and the balancing group of the tagging reagent. An "aldehyde" generally refers to an organic compound having a functional group with the structure —CHO. A "ketone" generally refers to an organic compound having a functional group with the structure RC(=O)R', where R and R' can be a variety of carbon-containing substituents. A "carboxylic acid" generally refers to an organic compound having a functional group with the structure R—COOH.

An "amino acid" refers to an organic compound containing an amino group ($NH_2$), a carboxylic acid group (COOH), and any of various organic side groups that have the basic formula $NH_2CHRCOOH$. Natural amino acids are those amino acids which are produced in nature, such as isoleucine, alanine, leucine, asparagine, lysine, aspartic acid, methionine, cysteine, phenylalanine, glutamic acid, threonine, glutamine, tryptophan, glycine, valine, proline, serine, tyrosine, arginine, and histidine as well as ornithine and selenocysteine.

The term "alkyl" refers to a monoradical of a branched or unbranched (straight-chain or linear) saturated hydrocarbon and to cycloalkyl groups having one or more rings. Alkyl groups as used herein include those having from 1 to 30 carbon atoms, preferably having from 1 to 12 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cycloalkyl groups include those having one or more rings. Cyclic alkyl groups include those having a 3-, 4-, 5-, 6-, 7-, 8-, 9-, 10-, 11- or 12-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group linked to oxygen and can be represented by the formula R—O. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups.

The term "alkenyl" refers to a monoradical of a branched or unbranched unsaturated hydrocarbon group having one or more double bonds and to cycloalkenyl groups having one or more rings wherein at least one ring contains a double bond. Alkenyl groups include those having 1, 2 or more double bonds and those in which two or more of the double bonds are conjugated double bonds. Alkenyl groups include those having from 1 to 20 carbon atoms, preferably having from 1 to 12 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9-, 10-, 11- or 12-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

The term "aryl" refers to a chemical group having one or more 5-, 6- or 7-member aromatic or heterocyclic aromatic rings. An aromatic hydrocarbon is a hydrocarbon with a conjugated cyclic molecular structure. Aryl groups include those having from 4 to 30 carbon atoms, preferably having from 6 to 18 carbon atoms. Aryl groups can contain a single ring (e.g., phenyl), one or more rings (e.g., biphenyl) or multiple condensed (fused) rings, wherein at least one ring is aromatic (e.g., naphthyl, dihydrophenanthrenyl, fluorenyl, or anthryl). Heterocyclic aromatic rings can include one or more N, O, or S atoms in the ring. Heterocyclic aromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following benzene, naphthalene, naphthoquinone, diphenylmethane, fluorene, fluoranthene, anthracene, anthraquinone, phenanthrene, tetracene, naphthacenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic radical, including monovalent, divalent and polyvalent radicals, of the aromatic and heterocyclic aromatic groups listed above provided in a covalently bonded configuration in the compounds of the present invention. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:
—COOR where R is a hydrogen or an alkyl group or an aryl group and more specifically where R is methyl, ethyl, propyl, butyl, or phenyl groups all of which are optionally substituted;
—COR where R is a hydrogen, or an alkyl group or an aryl groups and more specifically where R is methyl, ethyl, propyl, butyl, or phenyl groups all of which groups are optionally substituted;
—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
—N(R)$_2$ where each R, independently of each other R, is an alkyl group, acyl group or an aryl group and more specifically where R is methyl, ethyl, propyl, butyl, or phenyl or acetyl groups all of which are optionally substituted; or R and R can form a ring which may contain one or more double bonds.
—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;
—OCOOR where R is an alkyl group or an aryl groups;

—SO$_2$N(R)$_2$ where R is a hydrogen, an alkyl group, or an aryl group and R and R can form a ring;

—OR where R is H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

As used herein, the term "alkylene" refers to a divalent radical derived from an alkyl group or as defined herein. Alkylene groups in some embodiments function as attaching and/or spacer groups in the present compositions. Compounds of the present invention include substituted and unsubstituted $C_1$-$C_{30}$ alkylene, $C_1$-$C_{12}$ alkylene and $C_1$-$C_5$ alkylene groups. The term "alkylene" includes cycloalkylene and non-cyclic alkylene groups.

As used herein, the term "cycloalkylene" refers to a divalent radical derived from a cycloalkyl group as defined herein. Cycloalkylene groups in some embodiments function as attaching and/or spacer groups in the present compositions. Compounds of the present invention include substituted and unsubstituted $C_1$-$C_{30}$ cycloalkenylene, $C_1$-$C_{12}$ cycloalkenylene and $C_1$-$C_5$ cycloalkenylene groups.

As used herein, the term "alkenylene" refers to a divalent radical derived from an alkenyl group as defined herein. Alkenylene groups in some embodiments function as attaching and/or spacer groups in the present compositions. Compounds of the present invention include substituted and unsubstituted $C_1$-$C_{20}$ alkenylene, $C_1$-$C_{12}$ alkenylene and $C_1$-$C_5$ alkenylene groups. The term "alkenylene" includes cycloalkenylene and non-cyclic alkenylene groups.

As used herein, the term "cycloalkenylene" refers to a divalent radical derived from a cylcoalkenyl group as defined herein. Cycloalkenylene groups in some embodiments function as attaching and/or spacer groups in the present compositions.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As used herein, the term "halo" refers to a halogen group such as a fluoro (—F), chloro (—Cl), bromo (—Br) or iodo (—I).

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

As used herein, "isotopically labeled", "isotopic", "isotopes", "isotope", "isotopically-different", "isotopically enriched" and the like refer to compounds (e.g., tagging reagents, target analytes, labeled samples and end-products, etc.) whereby a process has introduced one or more isotopes into the relevant compound in excess of the natural isotopic abundance. "Isotopically-heavy" refers to a compound or fragments/moieties thereof that have been enriched with one or more high mass, or heavy isotopes (e.g., stable isotopes such as deuterium, $^{13}$C, $^{15}$N, and $^{18}$O).

In an embodiment, an isotopically enriched sample comprises a compound of the invention having a specific isotopic composition, wherein the compound is present in an abundance that is at least 10 times greater, for some embodiments at least 100 times greater, for some embodiments at least 1,000 times greater, for some embodiments at least 10,000 times greater, than the abundance of the same compound having the same isotopic composition in a naturally occurring sample. In another embodiment, an isotopically enriched sample has a purity with respect to a compound of the invention having a specific isotopic composition that is substantially enriched, for example, a purity equal to or greater than 90%, in some embodiments equal to or greater than 95%, in some embodiments equal to or greater than 99%, in some embodiments equal to or greater than 99.9%, in some embodiments equal to or greater than 99.99%, and in some embodiments equal to or greater than 99.999%. In another embodiment, an isotopically enriched sample is a sample that has been purified with respect to a compound of the invention having a specific isotopic composition, for example using isotope purification methods known in the art.

Isobaric Labeling

Numerous MS-based chemical derivatization quantitation approaches have been developed and widely used for quantitative proteomics and peptidomics (Ong et al., Nat. Chem. Biol. 2005, 1:252-262). Mass-difference labeling approaches introduce a mass difference for the same peptide by incorporating a light or heavy isotopic form of the labeling reagent. Light and heavy labeled peptides are combined prior to MS analysis, and quantitation is accomplished by comparing the extracted ion chromatogram peak areas of light and heavy forms of the same peptide. Methods such as isotope-coded affinity tags (ICAT), stable isotope labeling with amino acids in cell culture (SILAC), 4-trimethylammonium-butyryl (TMAB) labels, and reductive formaldehyde dimethylation have been widely used in mass-difference quantitation proteomics (Gygi et al., Nat. Biotechnol. 1999, 17:994; Li et al., Mol. Cell. Proteomics 2003, 2:1198-1204; Hansen et al., Mol. Cell. Proteomics 2003, 2:299-314; Ong et al., Mol. Cell. Proteomics 2002, 1:376-386; Zhang et al., Anal. Chem. 2002, 74:3662-3669; and Hsu et al., Anal. Chem. 2003, 75:6843-6852).

Although being well-established methodologies for quantitative proteomics, mass-difference labeling has two general limitations. First, typically only a binary set of samples can be compared due to the use of light and heavy labeling of a peptide (although a triplex example can sometimes be obtained where light, medium and heavy isotopes are used for quantifying the samples). Second, mass-difference labeling increases mass spectral complexity by introducing an extra pair of labeled peptides, thus decreasing the confidence and accuracy of quantitation. The first limitation has been addressed and overcome by several research groups by introducing multiple heavy labeled reagents, rather than just one (Hsu et al., Electrophoresis 2006, 27:3652-3660; Morano et al., Anal. Chem. 2008, 80:9298-9309; and Boersema et al., Proteomics 2008, 8:4624-4632). However, the second limitation is an inherent drawback of the mass-difference approach, and the spectral complexity is only increased with the use of multiple heavy isotope labeling reagents.

These limitations can be addressed through the use of isobaric labeling. There are two popular brands of isotopic labeling reagents, iTRAQ and TMT, currently sold in order to tag peptides when performing quantitative analysis of peptides using MS. Tandem mass tags (TMTs) were the first isobaric labeling reagents used to improve the accuracy for peptide and protein quantitation by simultaneous identification and relative quantitation during tandem mass spectrometry (MS/MS or $MS^2$) experiments (Thompson et al., Anal. Chem. 2003, 75:1895-1904). Two generations of TMTs were reported (TMT1 and TMT2), and each generation had two isobaric labels. Amine groups (N-terminus and ε-amino group of the lysine side chain) in peptides labeled with TMT1 produce fragments at m/z 270 and 273 at 70 V collision energy, whereas TMT2 produces fragments at m/z 287 and 290 at 35 V collision energy. Relative quantitation can be performed by comparing the intensities of these fragments to one another. A 6-plex version of TMTs was also recently reported (Dayon et al., Anal. Chem. 2008, 80:2921-2931), and 10-plex and even 11-plex quantifications may be obtained using additional mass defect tags.

iTRAQ follows the same principle as TMTs quantitation, but it improves the quantitation further by providing four isobaric labels with signature reporter ions that are one Da apart upon $MS^2$ fragmentation (Ross et al., Mol. Cell. Proteomics 2004, 3:1154-1169). Thus, iTRAQ allows for the quantitation of proteins present in four different biological states simultaneously (a 4-plex quantitation). These tags are structurally identical isobaric compounds with different isotopic combinations. Each sample is labeled individually, pooled together, and introduced into the mass spectrometer for quantitative analysis. Since samples are isobarically labeled, the same peptide from four samples produces a single peak in MS mode, but upon $MS^2$ fragmentation, each labeled sample gives rise to a unique reporter ion (m/z 114.1, 115.1, 116.1, and 117.1) along with sequence-specific backbone cleavage for identification. Relative quantitation is achieved by correlating the relative abundance of each reporter ion with its originating sample.

iTRAQ 8-plex quantitation follows the same quantitation principle as iTRAQ 4-plex quantitation (C. Leila, et al., Proteomics 2007, 7. 3651-3660). Instead of using four reporter ions (m/z 114.1, 115.1, 116.1, and 117.1) for quantitation of four samples, eight reporter ions (m/z 114.1, 115.1, 116.1, 117.1, 118.1, 119.1, 121.1 and 122.1) can be produced and used for simultaneous quantitation of eight samples. iTRAQ 8-plex reagents double the quantitation throughput over the 4-plex reagents. In addition to the higher throughput over a wider quantitation dynamic range, 8-plex reagents can also provide more accurate quantitation.

A common problem with the 4-plex iTRAQ reagent is that because the four reporter ions are only one Dalton apart, isotope peak gains from or losses to adjacent reporter ions affect both the accuracy and dynamic range of quantitation for 4-plex samples. The quantitation accuracy problem can be overcome by employing a complicated mathematic algorithm to quantify the reporter ions (A. Boehm, et al., BMC Bioinformatics 2007, 8. 214). A software package is needed for 4-plex quantitation which brings extra cost for data analysis. The mathematic approach works well for quantifying samples within ten-fold ratio difference. However, if two samples labeled by two adjacent reporter ions have abundance difference greater than ten-fold, the reporter ion representing lower concentration sample could potentially be buried by the isotope peak of the adjacent reporter ion representing high concentration sample (S. Y. Ow, et al., J. Proteome Res. 2009, 8. 5347-5355). Therefore, the quantitation dynamic range is reduced. Two adjacent reporter ions with one Dalton mass difference should be avoided to quantify samples varying in concentration greater than ten-fold. In this situation, 4-plex reagents can only be used to quantify two samples. 8-plex reagents can provide two Dalton mass difference reporter ions for quantitation of four samples. Because of the minimal interference of adjacent reporter ions, accurate quantitation and wider quantitation dynamic range can be achieved for four samples without sophisticated mathematical processing. Demand of high throughput protein/peptide LC/MS/MS quantitation in practice makes iTRAQ 8-plex highly desirable for multiple sample quantitation. However, the trade-off of accurate quantitation and wider dynamic range is the high price of iTRAQ 8-plex reagents (about $2,500 for a kit for five trials).

Isobaric $MS^2$ tagging approaches have also been successfully used in MS-based quantitative proteomics. However, their application as a routine tool for quantitative MS studies is limited by high cost. The high cost of commercial TMTs and iTRAQ comes from the challenge of synthesizing these compounds as multiple steps involved in the synthesis lead to moderate to low yields. A set of 6-plex deuterium-labeled DiART reagents was reported very recently with reduced cost of isobaric labeling. However, seven steps were still required to synthesize these compounds with only 30%-40% overall yield (Zeng et al., Chem. Commun. 2009, 3369-3371). Additionally, many alternate MS labels are too labile which leads to cleaving the tag from the peptide of interest during mass spectrometry analysis.

A new type of isobaric $MS^2$ tags with fewer steps involved in synthesis is desirable to further reduce experimental cost while taking full technical advantages of the isobaric $MS^2$ tagging approach. Formaldehyde dimethylation represents one of the most affordable approaches among all isotopic chemical derivatization techniques used for MS-based peptide and protein quantitation (Boersema et al., Proteomics 2008, 8:4624-4632; Ji et al., Proteome Res. 2005, 4:2099-2108; Ji et al., Proteome Res. 2005, 4:1419-1426; Ji et al., Proteome Res. 2005, 4:734-742; Huang et al., Proteomics 2006, 6:1722-1734; Ji et al., Proteome Res. 2006, 5:2567-2576; Ji et al., Anal. Chim. Acta 2007, 585:219-226; Guo et al., Anal. Chem. 2007, 79:8631-8638; Wang et al., J. Proteome Res. 2009, 8:3403-3414; Raijmakers et al., Mol. Cell. Proteomics 2008, 7:1755-1762; Synowsky et al., J. Mol. Biol. 2009, 385:1300-1313; Lemeer et al., Mol. Cell. Proteomics 2008, 7:2176-2187; Khidekel et al., Nat. Chem. Biol. 2007, 3:339-348; Rogers et al., Proc. Natl. Acad. Sci. U.S.A. 2007, 104:18520-18525; Aye et al., Mol. Cell. Proteomics 2009, 8:1016-1028; and Boersema et al., Nat. Protocols 2009, 4:484-494). However, isotopic formaldehyde labeling is a mass-difference labeling approach and, thus, lacks the advantages offered by the isobaric labeling approach.

A set of novel and cost effective N, N-dimethylated leucine (DiLeu) 4-plex reagents were developed as an attractive alternative to iTRAQ reagent for protein and peptide quantitation (Xiang, et al., Anal. Chem. 2010, 82. 2817-2825). Additional isobaric tagging reagents containing amine reactive groups were also developed and described in U.S. Pat. No. 9,388,132.

Isobaric Tandem Mass Tags Suitable for Carbohydrate and Glycan Labelling

Glycosylation refers to the process in which one or more of a wide variety of carbohydrates is attached to a functional group of another molecule, such as O-glycans and N-glycans attached to peptides (FIG. 1). Detection and quantification of glycans and glycosylation is highly important as glycosylation is involved in several biological processes and abnormal glycosylation is involved in several diseases including cancer, cardiovascular problems, and immunological disorders. Accordingly, intensive research efforts have been directed to mass spectrometry (MS)-based quantitative glycomics.

Figure 2:
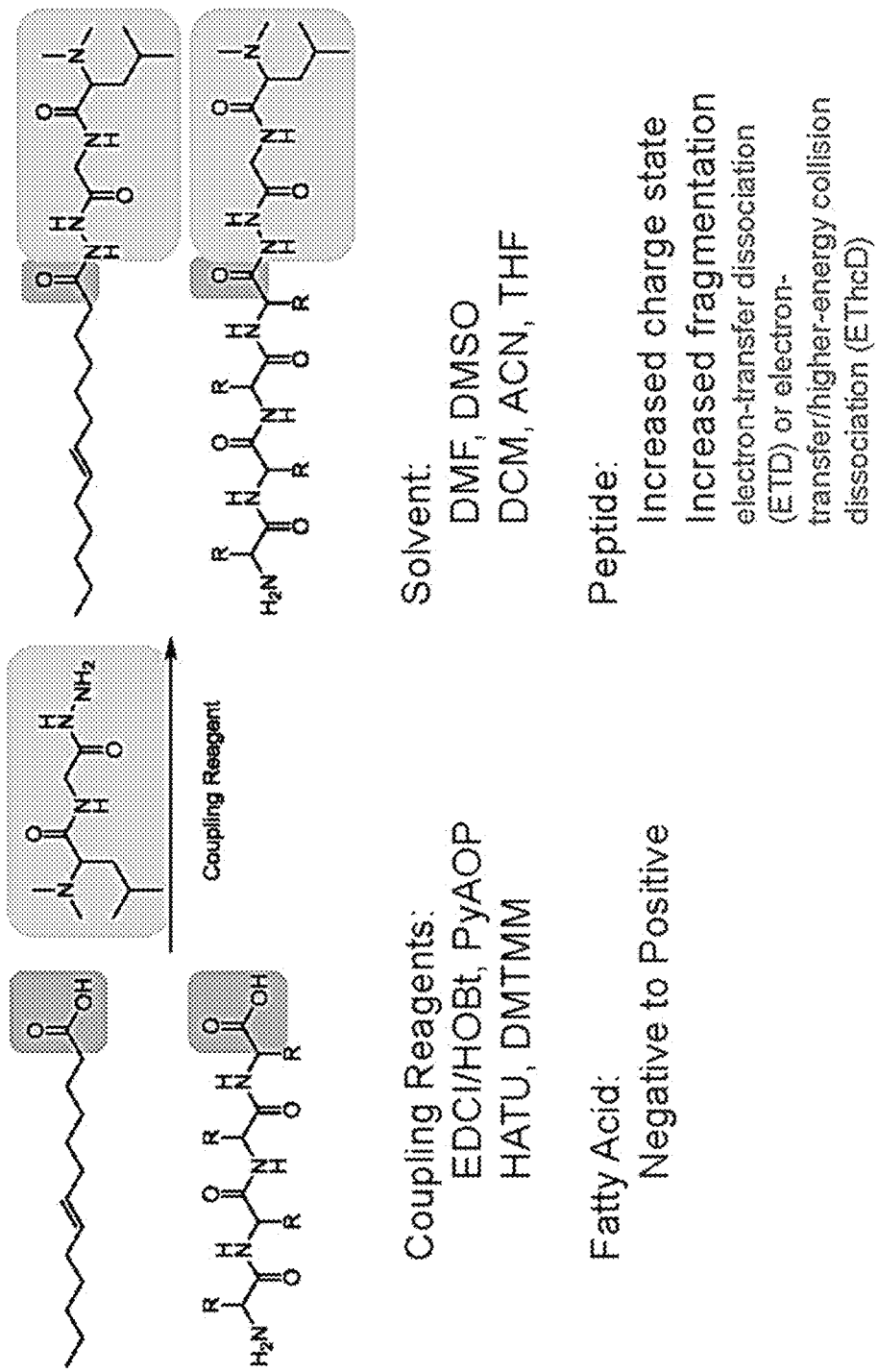
FIG. 2 illustrates a carboxylic acid labeling scheme for peptides and fatty acids according to an embodiment of the present invention.

A limiting factor of previous isobaric tagging reagents is that they were designed to attach to the amine groups of peptides and are unable to react with carboxylic acid groups, or similar reactive groups, present in glycans. The present invention provides a set of novel isobaric chemical tags, also referred herein as SUGAR (Isobaric Multiplex Reagents for Carbonyl Containing Compound). These labeling tags are compact and easy to synthesize at high yield and purity in just a few steps using commercially available starting materials. More importantly, the multiplex SUGAR tags are aldehyde-reactive, ketone-reactive and carboxylic acid-reactive, which offer the capability for labeling and quantitation of glycans, proteins/peptides, and fatty acids (FIG. 2).

The tagging reagents of the present invention comprise: a) a reporter group, having at least one atom that is optionally isotopically labeled; b) a balancing group, also having at least one atom that is optionally isotopically labeled, and c) an aldehyde, ketone, or carboxylic acid reactive group able to react with an aldehyde, ketone, or carboxylic acid group of the molecule to be tagged, such as a glycosylated side chain of a peptide.

A notable feature of this labeling approach is the production of intense immonium al ions when a dimethylated amino acid (such as a dimethylated leucine) undergoes tandem mass spectrometry ($MS^2$) dissociation. Additionally, the use of these tags enable multiplex analysis (i.e., at least 4 plex, 8 plex, 12 plex, and even 16 plex analysis).

For 4-plex SUGAR tags, reporter ions with 1 Da mass difference in $MS^2$ spectra enable the use of mass spectrometers even with modest resolution, making it more broadly applicable to a wide variety of instrument platforms and accessible to a larger number of researchers. The performance of one of the SUGAR tags, hydrazide glycine dimethyl leucine, has been benchmarked using both non-isotope version and 4-plex version and have observed high labeling efficiency of glycans released from glycoprotein bovine thyroglobulin (>90% of all glycans, >95% of average), enhanced backbone fragmentation at reduced normalized collision energies with improved intensity of reporter ions. This improved performance will help to increase the accuracy and dynamic range of glycan quantitation.

The tags of the present invention are beneficial in that they have the capability to label both aldehyde, ketone, and carboxylic acid containing compounds. More specifically, the SUGAR tags are aldehyde-reactive, ketone-reactive, and carboxylic acid-reactive, which offer the capability for labeling and quantitation of glycans, proteins/peptides, and fatty acids. No commercially available tag has been applied for aldehyde, ketone and carboxylic acid labeling.

SUGAR tags are also easy to synthesize at high yield and purity in just a few steps using commercially available starting materials, including amino acids, formaldehyde, sodium cyanoborohydride, amino acids methyl ester, N-(3-Dimethylaminopropyl)-N'-ethylcarbodiimide hydrochloride, hydroxybenzotriazole, and hydrazine, thus providing an easy and cost-efficient synthesis approach.

The present tags also provide a simple labeling protocol and high labeling efficiency. It only takes 2 hours to perform labeling chemistry for SUGAR tags with glycans because of the high reactivity of hydrazide group. Additionally, high labeling efficiencies were observed for neutral and acidic N-glycans (>90%). Near complete labeling were observed for most of N-glycans, especially for some larger N-glycans, such as $H_9N_2$. (The labeling efficiency has been significantly improved compared to AminoxyTMT (~50%), which is a commercially available isobaric tag for quantitative glycan analysis.)

The present tags also provide high reporter ion yield with complete backbone fragment ions at a single collisional energy level. SUGAR tags allow high reporter ion yield at a relatively low collisional energy level, at which the backbone fragments were also preserved in a single spectrum. Both the N-glycan backbone composition (backbone fragment ions) and the relative quantitation (reporter ion intensities) can be obtained in a single scan event. In contrast, difficulty is experienced when using AminoxyTMT, which requires higher collisional energy to release the reporter ion, thus, losing backbone fragment information. In order to obtain both structure and quantity information with AminoxyTMT, one glycan has to be fragmented with two different collisional energy levels: one at lower energy to obtain backbone fragments but minimal reporter ions; one at higher energy to obtain reporter ions but no backbone fragments.

The present tags also provide good quantification performances (accuracy and precision) as well as high throughput multiplexed quantitative analysis. The quantification performance of SUGAR tags has been evaluated by labeling N-glycans from glycoproteins and labeled with 4-plex SUGAR tags at a ratio of 1:1:1:1. Low relative error (<15%) and small standard deviation were observed on various types of N-glycans (neutral/high mannose, neutral/complex, acidic/complex). Additionally, 4-plex SUGAR tags can be synthesized at a fast and cost-effective fashion, which significantly reduces instrument time and inter-sample variance. Higher-plex versions of SUGAR tag are further possible with slight modifications.

SUGAR tags can also be applied on a wide variety of instrument platforms with MS/MS capabilities. It does not require special dissociation techniques (ETD, ECD, etc.) which are only available on certain instruments. Moreover, as 4-plex SUGAR is not a mass-defect based tag, it does not rely on high-resolution instrument platform. The reporter ions with 1 Da difference in $MS^2$ spectra enable the use of instrument with low resolving power, making it more broadly accessible.

Additionally, the present invention provides isobaric 8-plex tagging reagents which can also be used to provide 16-plex reagents. In the case of previous 4-plex reagents, the number of reporter ions was limited by the balancing group, in that case a carbonyl group. Unfortunately, the carbonyl group could only be modified 4 different ways using $^{13}C$ and $^{18}O$. To overcome this limitation, the present invention uses an amino acid to form the balancing group. Amino acids were chosen for the balancing group for several reasons: they can bear more isotopes than a carbonyl group, isotopic amino acids with various isotopic combinations are readily commercially available, and the methods of coupling two amino acids are well established.

With the general 8-plex reagent structure, instead of four reporter ions for four samples, eight reporter ions can be used to double the throughput. Introducing 8 or more mass differences to the same analyte allows 8 or more different concentrations of the same analyte to be detected in a single LC/MS run. The four reporter ions produced from previous 4-plex dimethyl leucine tagging reagents (m/z 115.1, 116.1, 117.1, and 118.1) were extended to eight reporter ions (m/z 114.1, 115.1, 116.1, 117.1, 118.1, 119.1, 121.1, and 122.1) by incorporating different numbers of stable isotopes (deuterium, $^{13}$C, $^{15}$N, and $^{18}$O) in an alanine based balancing group.

In addition, the 8-plex reagents provide increased quantitation accuracy and a wider quantitation dynamic range. A common problem for quantitation with 4-plex reagents using reporter ions which are only 1 Da apart is the interference from adjacent isotopic peaks. Oftentimes, a mathematic algorithm is needed to achieve accurate quantitation, as is the case with the 4-plex reagents. In contrast, 8-plex and 16-plex reagents will offer a 2 Da separation between reporter ions if used in a 4-plex manner. This mitigates the isotope interferences present with 1 Da difference reporter ions thereby eliminating the need for complex mathematical processing in isobaric quantitative experiments.

Besides multiplex quantitation, the 8-plex and 16-plex dimethylated amino acid tags also promote enhanced fragmentation, thereby allowing more confident protein identification from tryptic peptides and de novo sequencing of neuropeptides and metabolites.

The isobaric tagging reagents of the present invention can generally be synthesized in simple three or four step synthesis. The ease of synthesis provides high yields lowering the cost as compared to other commercially available reagents. The ease of synthesis allows the synthesis of tagging reagents with varying numbers of isotopes (primarily deuterium). Because each tagging reagent would produce a reporter group having a unique molecular weight, each differently labeled molecule is able to be detected and relatively quantified by tandem mass spectrometry. It is believed using these different labels in a single experiment would act like multiple standards. The quantities of labeled molecules can be calculated from a standard curve created using the different amounts of the different isotopically labeled molecules. Instead of having to run multiple different analyses, the same information can be gleaned from a single experiment.

The development and application of a set of novel N,N-dimethylated amino acid 8-plex, 12-plex, and 16-plex isobaric tandem mass (MS$^2$) tagging reagents with high quantitation efficacy and greatly reduced cost for neuropeptide, protein and small molecule analysis are described below. These tagging reagents resemble the general structure of a tandem mass tag in that it contains an aldehyde, ketone, or carboxylic acid reactive group, a balance group, and a reporter group. All labeling reagents are readily synthesized from commercially available chemicals with greatly reduced cost.

EXAMPLES

Example 1—Isobaric Aldehyde-Reactive Dimethyl Leucines with Improved Reporter Ion Yield as Chemical Tools for Quantitative Glycomics Glycosylation is one of the most important post-translational modifications as it is involved in several biological processes such as cell-cell recognition, communication and immunity response (Varki et al., Biological Roles of Glycans. In Essentials of Glycobiology, 2nd ed., Cold Spring Harbor (N.Y.), 2009; Moremen et al., Nat Rev Mol Cell Biol, 2012, 13 (7): 448-62; Dwek, R. A., Chem Rev, 1996, 96 (2): 683-720; and Defaus et al., Analyst, 2014, 139 (12): 2944-67). Abnormal glycosylation is relevant to diseases including cancer, cardiovascular problems, neurodegenerative diseases, and immunological disorders (Taniguchi et al., Mol Cell Proteomics 2008, 7 (3): 626-7; An et al., Curr Opin Chem Biol, 2009, 13 (5-6): 601-7; Alley et al., Chem Rev, 2013, 113 (4): 2668-732; and Arnold et al., Proteomics, 2008, 8 (16): 3284-93). Therefore, quantification of glycans is highly important and intensive research efforts have been directed to MS-based quantitative glycomics. However, the difficulty in detection of native glycans limits the characterization and quantification because of the hydrophilic property, relatively low basicity as well as the lack of chromophore for optical detection, resulting in poor ionization and detection using both MS and optical methods.

Dimethyl leucine (DiLeu) is a set of isobaric tags originally designed and developed to have amine reactive groups for protein quantitative analysis (Xiang et al., Anal Chem 2010, 82 (7): 2817-25). By incorporating $^2$H, $^{13}$C, and $^{15}$N isotopes into the DiLeu structure, up to 12-plex DiLeu tags can be synthesized and utilized for simultaneous quantification of 12 samples or performing quantitative analysis of triplicates of four different samples (Frost et al., Anal Chem, 2015, 87 (3): 1646-54). Although DiLeu has recently become a powerful tool for quantitative proteomics, several challenges remain unsolved for use with glycans and similar molecules: (1) the difficulty in producing sufficient reporter ions during fragmentation for quantitation; (2) the difficulty in obtaining glycan identification and relative quantification.

Figure 3:
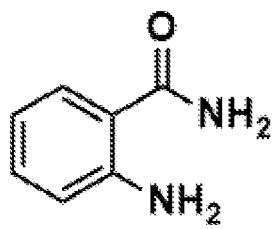
FIG. 3 shows exemplary fluorescent agents used to detect the presence of glycans.
Figure 3:
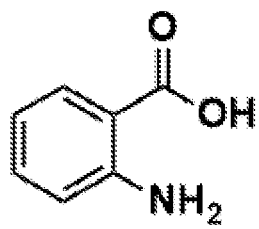
Figure 3:
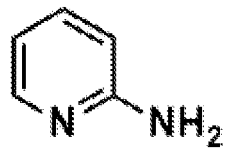
Figure 3:
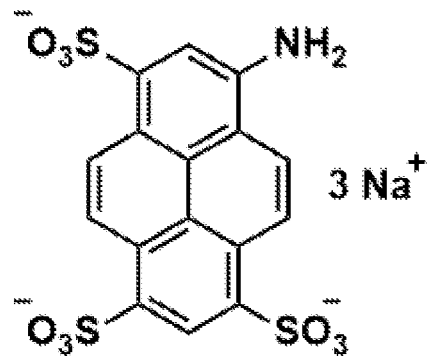
Figure 3:
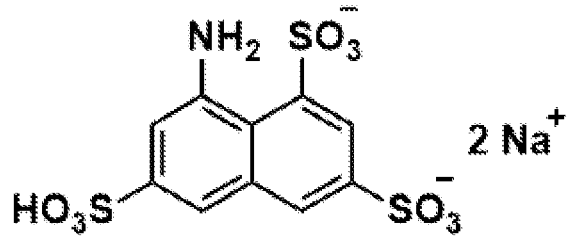

Several previous strategies have been developed to overcome the inherent limitations of natural glycan detection. The most widely used fluorescence detection (FIG. 3) was developed by Bigge et al. (Anal Biochem, 1995, 230 (2): 229-38). In this method, glycans were labeled with 2-aminobenzamide (2-AB) or 2-aminobenzoic acid (2-AA) via reductive amination to enable the fluorescence detection. 2-AB has since been widely applied in chromatographic analysis of glycans. The structural assignment could be performed by comparing the elution positions with extensively developed database of 2-AB labeled glycans in hydrophilic interaction liquid chromatography (HILIC) with fluorescence detection (Royle et al., Anal Biochem, 2008, 376 (1): 1-12). 2-AA is also widely used in HPLC and CE separations for glycan analysis. It is a carboxylic acid which has capability to be detected in both positive and negative mode for neutral and sialic acid-rich glycan species (Anumula et al., Glycobiology 1998, 8 (7): 685-94). Later, 2-aminopyridine (PA), 1-aminopyrene-3,6,8-trisulfonic acid (APTS) and 2-aminonaphthalene trisulfonic acid (ANTS) were well developed for different separation and detection methods (Anumula et al., Anal Biochem 2006, 350 (1): 1-23).

With technological advancement of MS, MS-based quantitative glycomics has become promising. The structural characterization as well as relative quantification can be performed in a high-throughput manner. The native glycans can be labeled with hydrophobic small molecules that could increase the ionization efficiency. The backbone fragments produced during fragmentation can be used to elucidate structure for characterization while intensities of parent ions or fragment peaks enable relative quantification of glycans.

There are three major strategies for relative quantification purpose. The most common strategy is isotopic labeling in which the target molecule is labeled with the same small molecule with different isotope configurations. Different isotope configuration incorporates different mass to the target. Thus, the relative quantification could be obtained by comparing the intensities of the labeled glycan ions. For example, [H$_4$]-PA and [D$_4$]-PA labels were applied in the glycosylation analysis (Yuan et al., J Chromatogr A, 2005, 1067 (1-2): 145-52). Promising relative quantitative glycomics results were obtained by intensity comparison of target ions with 4 Da difference. However, the retention time shift was observed between [$H_4$]-PA and [$D_4$]-PA labeled glycans on a $C_{18}$ column. To address the problem of retention time shift, [$^{12}C_6$]-alanine and [$^{13}C_6$]-alanine were used (Xia et al., Anal Biochem, 2009, 387 (2): 162-70). No retention time shift was observed on $C_{18}$ column. The other strategy performed separation of [$H_4$]-2-AA and [$D_4$]-2-AA labeled glycans by size exclusion to avoid the retention time shift (Hitchcock et al., Proteomics, 2008, 8 (7): 1384-97). However, several disadvantages of isotopic labeling strategy are noted. First, the pairs of isotopic peaks add the complexity of the full MS scan, which could complicate spectral interpretation. Second, most isotopic labels only contain dual plex that allow for binary quantitation. Since the mass difference between each plex should be greater than 4 Da to enable accurate quantification, the number of isotopes to be incorporated in labels imposes a limit on the plex number for multiplex quantitation using stable isotope labeling method.

Another labeling strategy is called mass defect labeling. Because of the different nuclear binding energy for each atom, the 'missing mass' or mass defect for each atom is slightly different according to the Einstein's equation. The mass defect labeled glycan would have the same nominal mass while the accurate mass is slightly different. Thus, the intensity of pair of peaks could be used for relative quantification using high-resolution mass spectrometer. $^{13}CH_3I$ and $^{12}CH_2DI$ were used (Atwood et al., J Proteome Res, 2008, 7 (1): 367-74) in glycan analysis via permethylation while 3 mDa difference was added by labeling with either derivatization reagent for each permethylation site. The advantage of mass defect labeling is the ease of spectral interpretation since the pair of peaks would merge together under low-resolution mass measurement which also increases the detection sensitivity. However, high-resolution requires longer time for scanning process so that fewer spectra could be obtained during acquisition. The higher plex also requires ultra-high resolution, sometimes over 1 M resolving power is required for separating subtle mass differences between isobaric labels, which restricts the application of mass defect quantification.

Besides these two full MS-based quantification strategies, isobaric labeling becomes popular recently because of the simplified spectra, increased detection sensitivity, high plexing capability and low-resolution requirement (Hahne et al., Anal Chem, 2012, 84 (8): 3716-24; Yang et al., Sci Rep, 2015, 5: 17585; and Yang et al., Anal Chem, 2013, 85 (17): 8188-95). The isobaric tags contain a reporter, a balancer and a reactive group. Different configurations of isotopes are incorporated into the reporter which can be fragmented to produce reporter ions in low mass range for quantification purpose. The balancer has another set of isotopes to keep the same nominal mass between each tag. The reactive group is labeled with glycan to form the conjugate. Since each tag has the same nominal mass, the full MS spectra from multiple samples remain relatively simple to interpret. Moreover, the low-resolution requirement allows the profile to be acquired on most instrument platforms. The quantitative results could then be obtained with identification via backbone fragmentation. The intensities of reporter ions can be used for quantification purpose.

Figure 4:
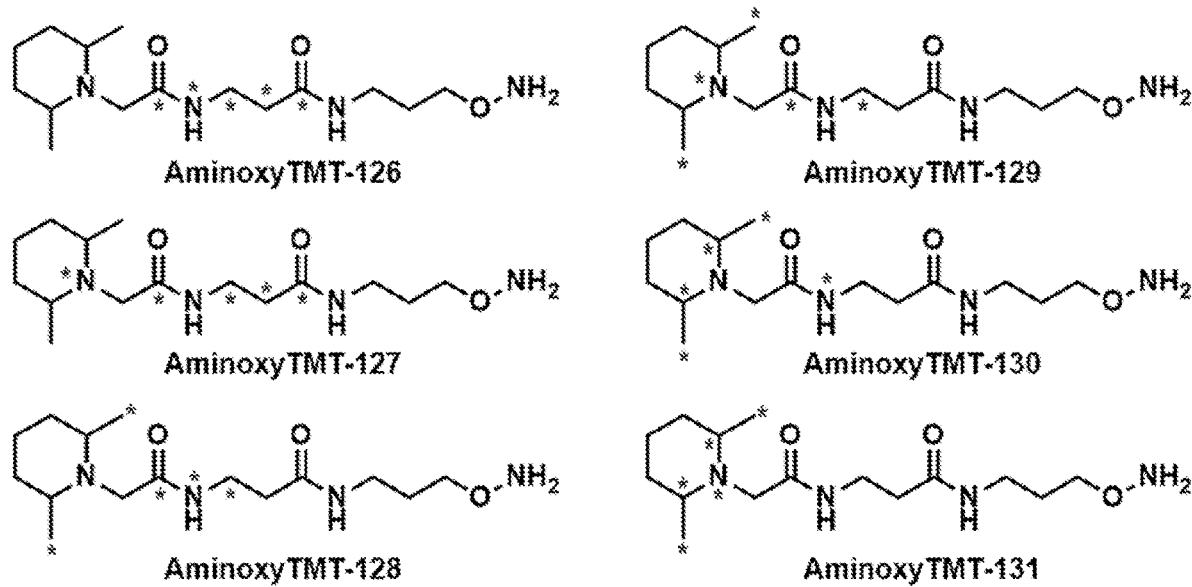
FIG. 4 shows isotopically labeled AminoxyTMT reagents.

Although several isobaric tags have been developed for glycan MS analysis recently, the performances of these tags are limited. For example, AminoxyTMT (FIG. 4), which is a set of commercially available isobaric tags for glycans, suffers from poor reporter ion yield and poor labeling efficiency for some complex glycans. In general, the most common labeling reaction for native glycan is reductive amination because of the high specificity and complete labeling efficiency. The labeling condition for AminoxyTMT has been optimized decades ago (Bigge et al., Anal Biochem, 1995, 230 (2): 229-38). The concentration of the labels was recommended to be at least 0.25 M while 1 M reducing agent was required. The derivatization was performed in 30% acetic acid of dimethyl sulfoxide within 2 hours. The reaction temperature of 60° C. was found to be optimal while higher temperature would accelerate the reaction with partial degradation and loss of sialic acid. However, AminoxyTMT performs labeling reaction via reversible imine formation without any reduction. Thus, it is possible for the conjugated glycan to move back to the native glycan.

Figure 5:
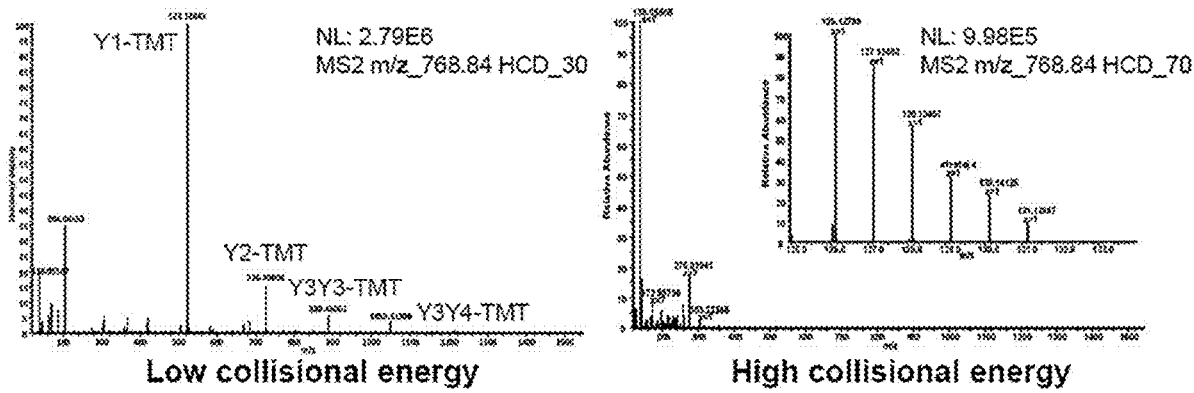
FIG. 5 illustrates limitations of AminoxyTMT reagents including MS spectra obtained using AminoxyTMT reagents at low collisional energy and high collisional energy.

Additionally, if low collisional energy is used with AminoxyTMT, the reporter ion will not fully release. AminoxyTMT therefore requires higher collisional energy to release the reporter ion; however, this will result in the fragmentation of the backbone fragment (FIG. 5). In order to obtain both structure and quantity information with AminoxyTMT, the glycan has to be fragmented with two different collisional energy levels: one at lower energy to obtain backbone fragments but minimal reporter ions; one at higher energy to obtain reporter ions but no backbone fragments.

Figure 6:
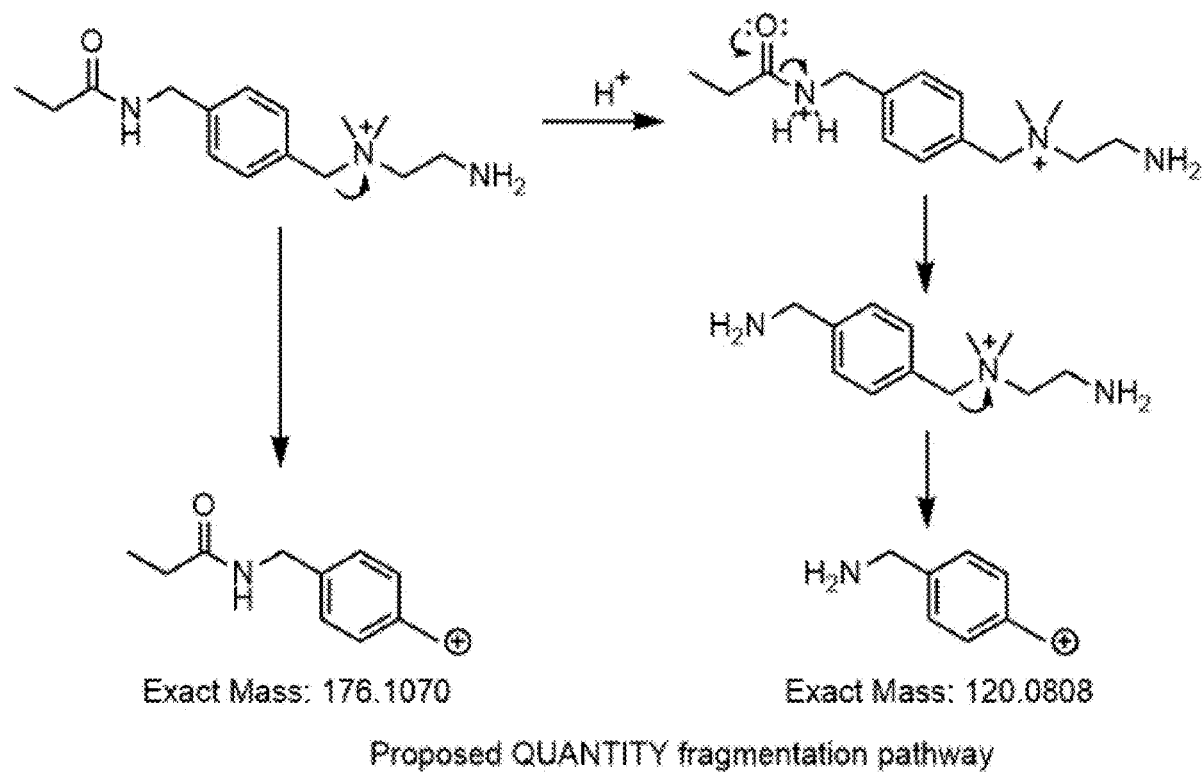
FIG. 6 shows QUANTITY isobaric tags used for glycan detection including proposed fragmentation pathways.

QUANTITY (Yang et al., Sci Rep, 2015, 5: 17585) is another set of isobaric tags for glycan analysis which contains quaternary amine with permanent charge to improve the ionization efficiency. The labeling reaction yields near complete conjugated glycan via reductive amination while the reporter ion yield is limited for some complex glycans because of the two cleavage sites of the reporter (FIG. 6). Lower energy could only produce limited reporter ions while higher energy would cleave the second site to diminish the intensity of reporter ion. The optimized collisional energy is critical for QUANTITY-labeled glycan moiety.

The successful development of high performance quantitative glycomics chemical tool provides an ideal workflow for quantitative glycan analysis in biological samples. Herein, the present example proposes a set of novel isobaric tags based on the customized DiLeu structure to overcome poor labeling efficiency and limited reporter ion yield by combining DiLeu backbone with aldehyde-reactive group to create a high performance quantitative glycomics chemical tool.

Candidate Labeling Tag Structure Design.

DiLeu is a scaffold used with isobaric tags that was designed and developed for protein quantitative analysis almost a decade ago (Xiang et al., Anal Chem, 2010, 82 (7): 2817-25). 12-plex DiLeu is available which can perform triplicate quantitative analysis of proteins from four different samples by incorporating $^2H$, $^{13}C$ $^{15}N$ isotopes into the DiLeu structure (Frost et al., Anal Chem, 2015, 87 (3): 1646-54). Although DiLeu has become a powerful tool for quantitative proteomics recently, several challenges remain unsolved: the difficulty in producing sufficient reporter ions during fragmentation and the difficulty in glycan identification and relative quantification. However, by incorporating specific linkers and aldehyde reactive groups into the DiLeu structure, both challenges can be solved. The isobaric tags for quantitative glycomics always suffer from the limited reporter ion yield while DiLeu backbone fragmentation requires lower energy to produce reporter ions. In addition, the reactive group incorporated in the tag would increase the labeling activity and enable simultaneous identification and quantification of labeled glycan. Thus by combining DiLeu backbone with aldehyde-reactive group, a set of novel isobaric tags is provided to overcome poor labeling efficiency and limited reporter ion yield.

As used in the examples below, "DiLeu" refers to a SUGAR tag based on N,N-dimethylated leucine having an aldehyde, ketone, and/or carboxylic acid reactive group. However it should be understood that SUGAR tags may include compounds other than N,N-dimethylated leucine.

Preliminary Results.

Figure 7:
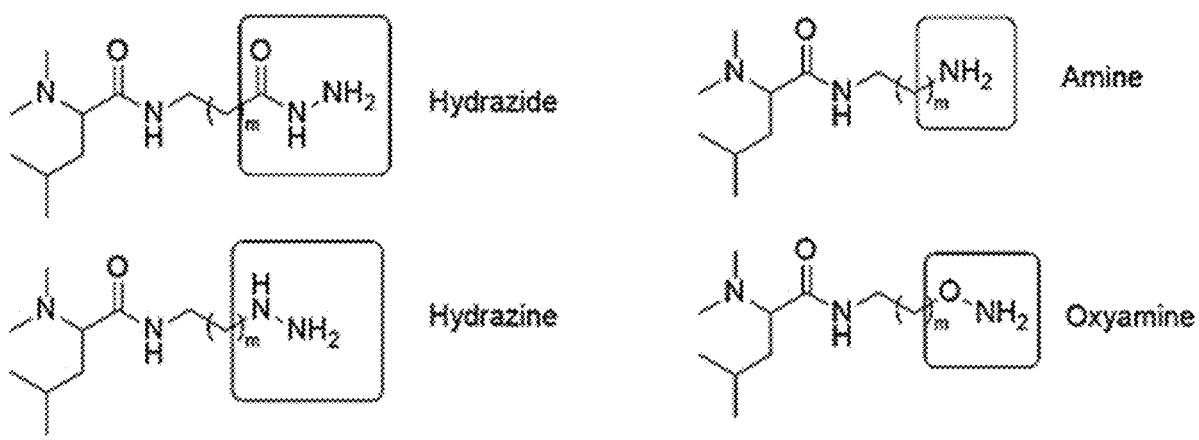
FIG. 7 shows exemplary aldehyde, ketone, or carboxylic acid reactive groups for SUGAR tags in an embodiment of the invention.
Figure 8:
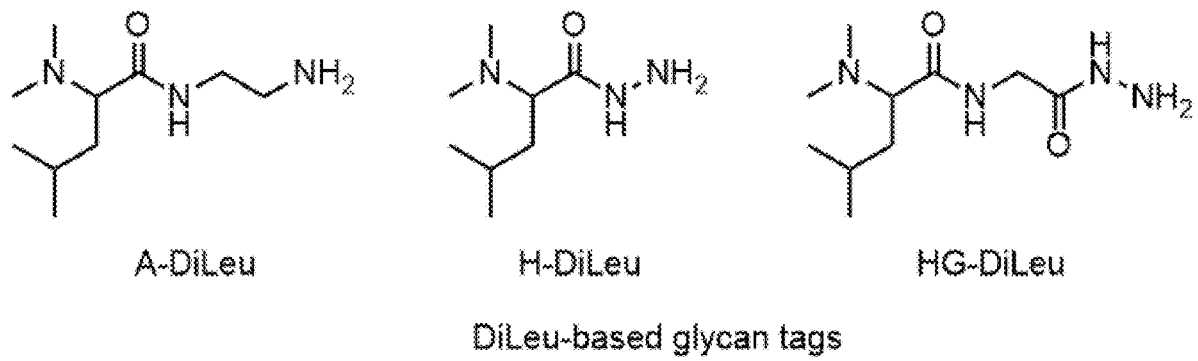
FIG. 8 shows DiLeu-based labeling tags (A-DiLeu, H-DiLeu, and HG-DiLeu) for glycan detection (top), and a synthesis pathway for producing the A-DiLeu glycan tag (bottom) according to an embodiment of the present invention.
Figure 8:
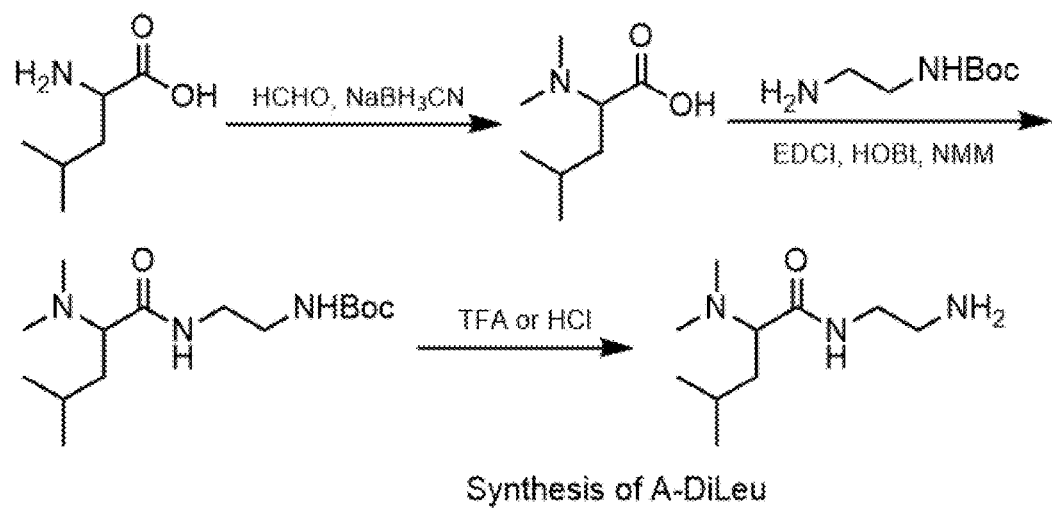

The reactive group can be any functional group able to react with any aldehyde, ketone, or carboxylic acid group of a molecule, including but not limited to a hydrazide, hydrazine, amine, or oxyamine (FIG. 7). As linkers could affect the fragmentation behavior while reactive groups have different labeling activities, three candidates were proposed (amine-DiLeu (A-DiLeu), hydrazide-DiLeu (H-DiLeu) and hydrazide-glycine-DiLeu (HG-DiLeu)) with different linkers (FIG. 8), including ethylenediamine, hydrazine and glycine; and reactive groups, including primary amine and hydrazide. With the DiLeu backbone structure, the reporter ions could be released with lower collision energy. Either primary amine or hydrazide would allow regular reductive amination for labeling reaction to achieve high yield.

Synthesis Strategy Design.

With the structures of three candidates being designed, the synthetic strategies were subsequently developed. Because of the relatively simple functional group transformation, all the candidates can be made within 3 steps from commercially available materials in high yield.

Figure 9:
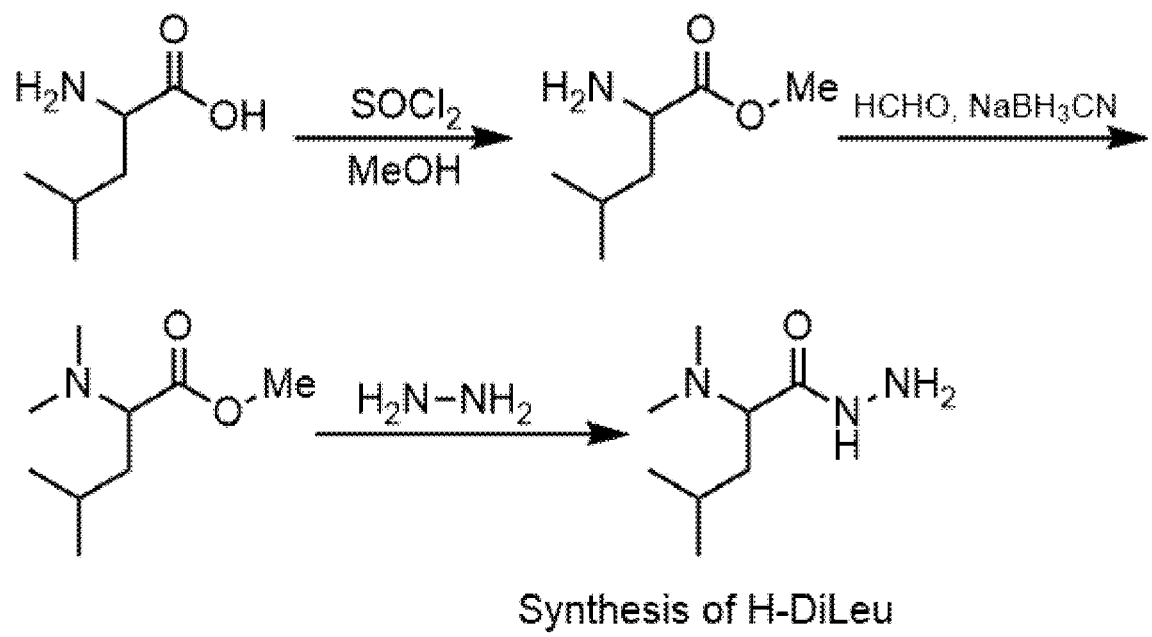
FIG. 9 shows a synthesis pathway for producing the H-DiLeu glycan tag according to an embodiment of the present invention.
Figure 10:
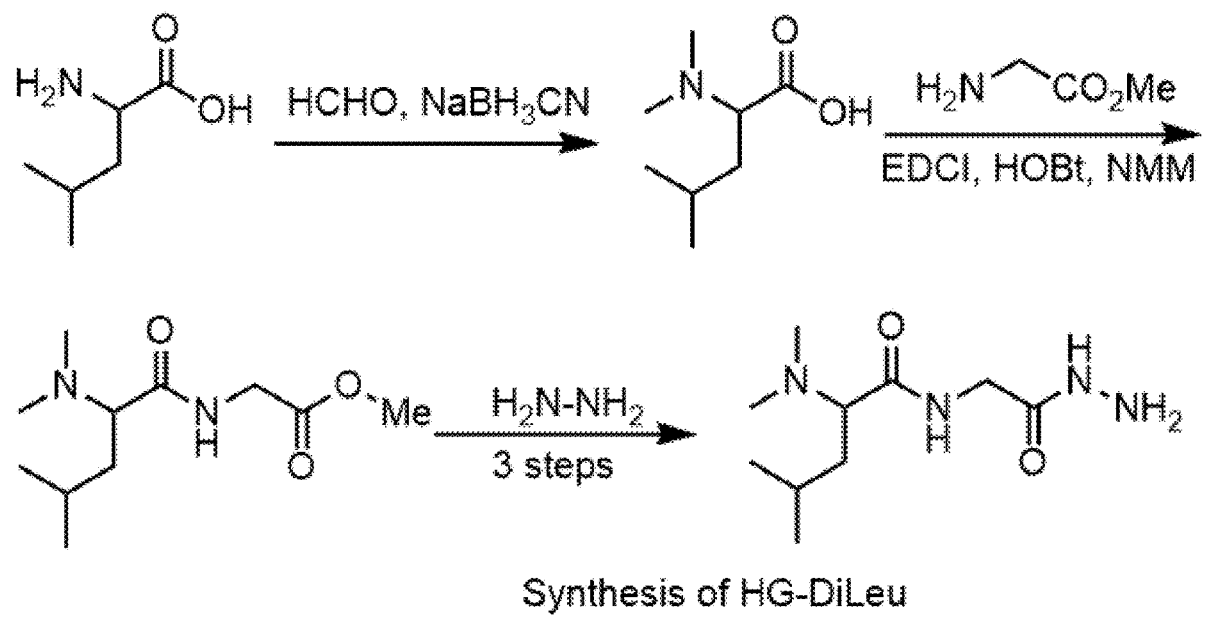
FIG. 10 shows a synthesis pathway or producing the HG-DiLeu glycan tag according to an embodiment of the present invention.

For A-DiLeu (FIG. 8), starting with leucine, reductive amination reaction was applied to add dimethyl group onto the primary amine. Then, the mono-Boc-protected ethylenediamine was coupled with DiLeu to form a Boc-protected amide. In the last step, the Boc protecting group was removed by adding acid, like HCl in dioxane or trifluoroacetic acid (TFA) to produce desired A-DiLeu tag. The synthesis of H-DiLeu could be done in 3 steps as well (FIG. 9). Leucine was treated with thionyl chloride in methanol to convert carboxylic acid into methyl ester. Next, reductive amination added two methyl groups at the N-terminus of leucine. In the final step, hydrazine was added to the dimethyl leucine methyl ester in methanol or ethanol solution. The reaction was completed within 1 hour to convert ester to desired hydrazide DiLeu. However, as DiLeu reporter ion release undergoes amide cleavage, the hydrazide group in H-DiLeu might affect the fragmentation behavior. HG-DiLeu was developed by employing glycine as linker between DiLeu and reactive hydrazide group to keep the amide cleavage possible (FIG. 10). The synthesis was done in 3 steps with 56% overall yield. Dimethylation in first step is the same as regular DiLeu synthesis. Second, glycine methyl ester was coupled with DiLeu by EDCI/HOBt amidation. Last, hydrazide was obtained from the methyl ester attacked by hydrazine in almost quantitative yield.

Results.

After the candidates were synthesized, the structure was confirmed by nuclear magnetic resonance spectroscopy (NMR) and MS, and the candidates were aliquoted to 1 mg for performance evaluation were the labeling efficiency, fragmentation behavior and quantitation accuracy were examined.

Figure 11:
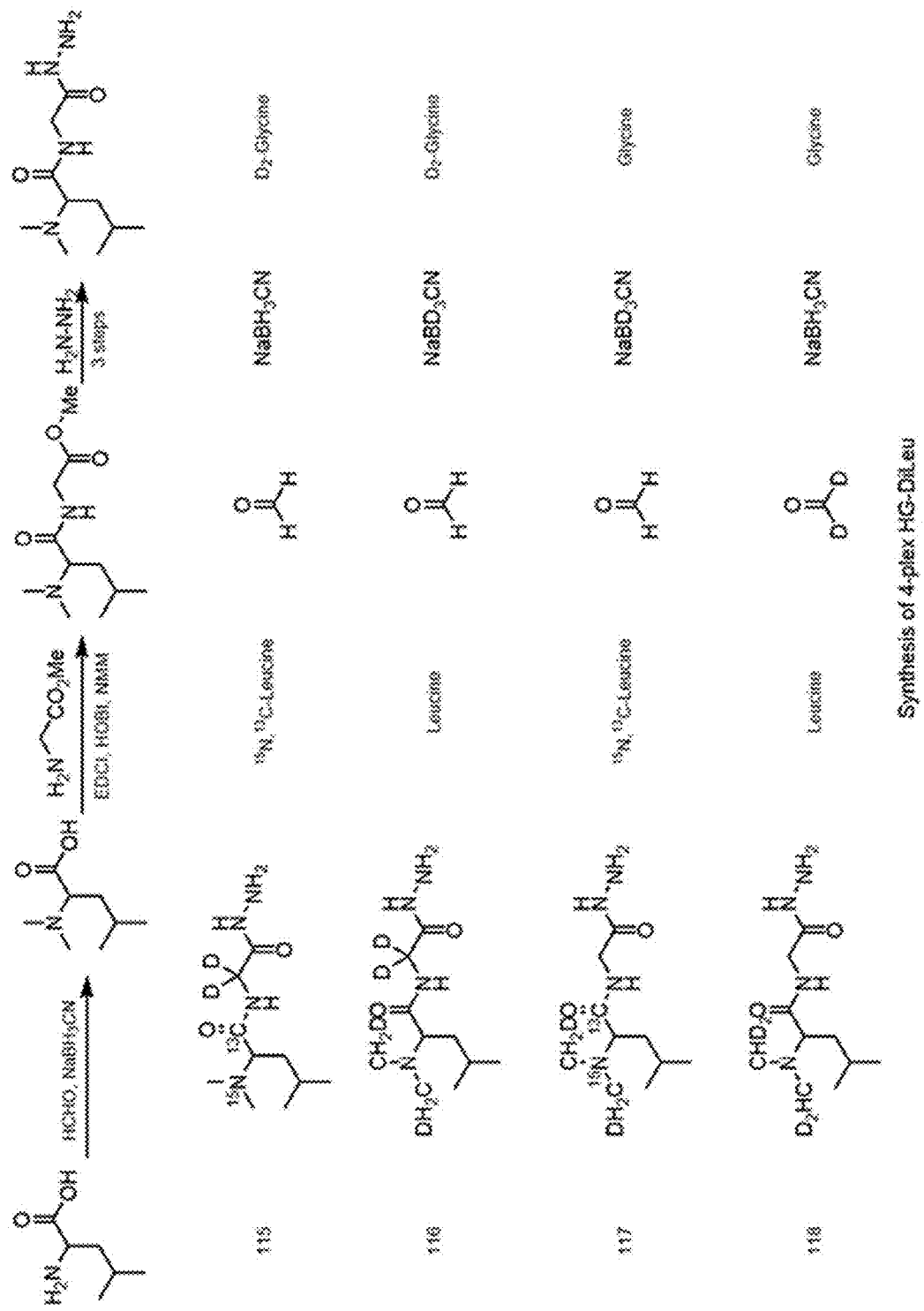
FIG. 11 shows isotope positions and synthesis of a 4-plex HG-DiLeu (SUGAR) tagging system in an embodiment of the invention.
Figure 12:
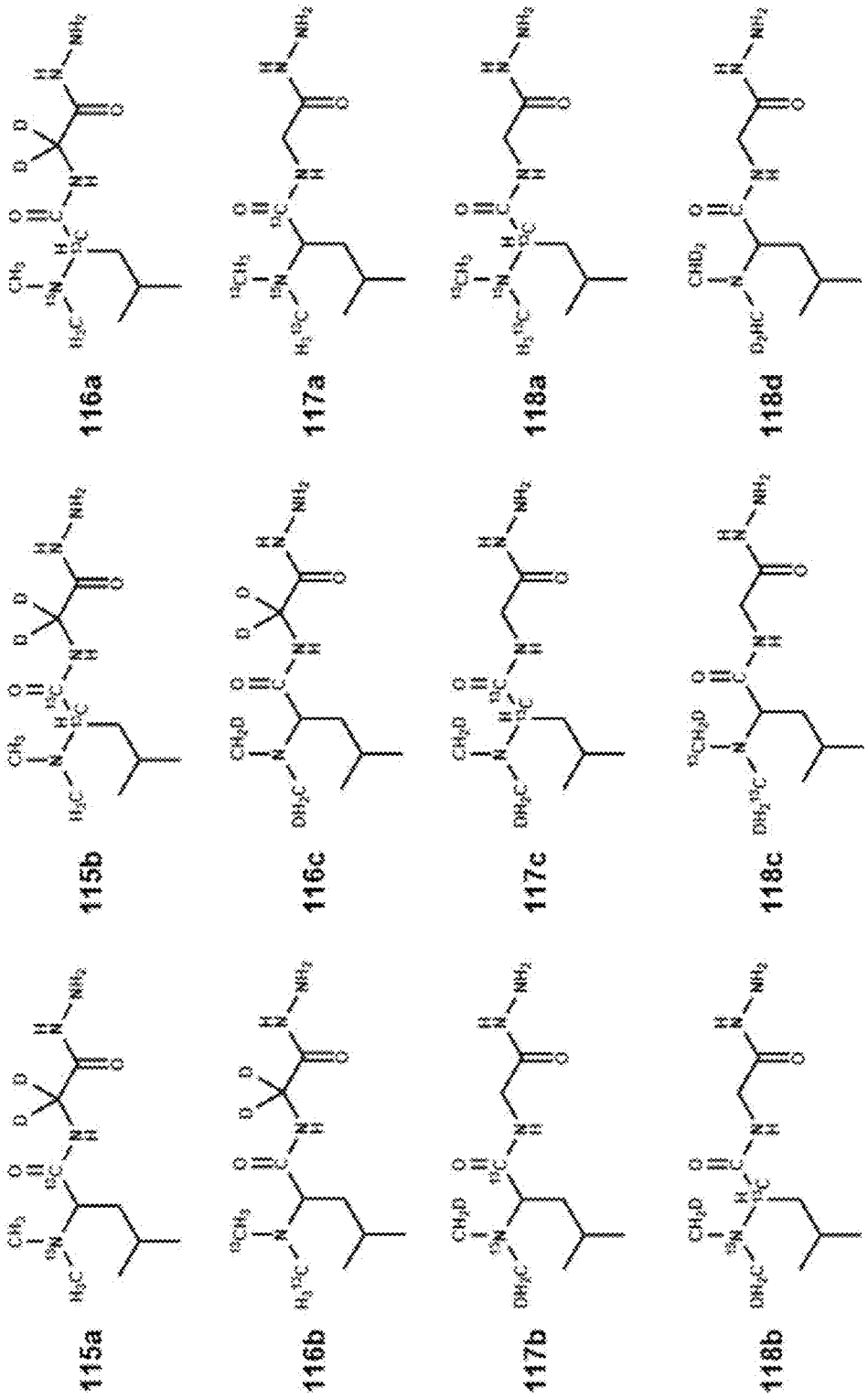
FIG. 12 shows isotope positions of a 12-plex HG-DiLeu (SUGAR) tagging system in an embodiment of the invention.
Figure 13:
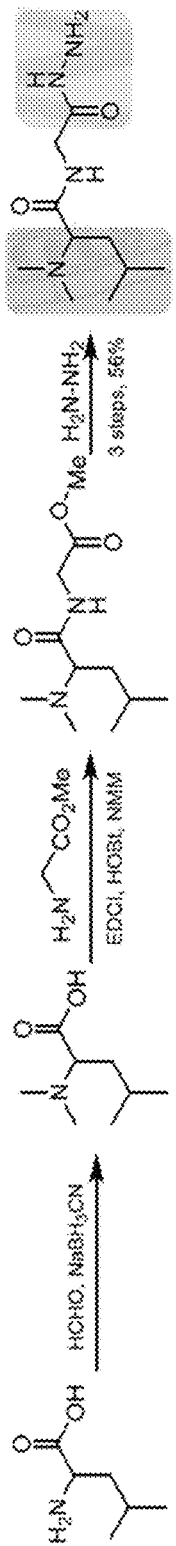
FIG. 13 shows a $MS^1$ spectrum of SUGAR labeling with $(Glc)_8$ as a glycan standard in an embodiment of the present invention. In this example, over 85% yield was achieved by SUGAR labeling.
Figure 13:
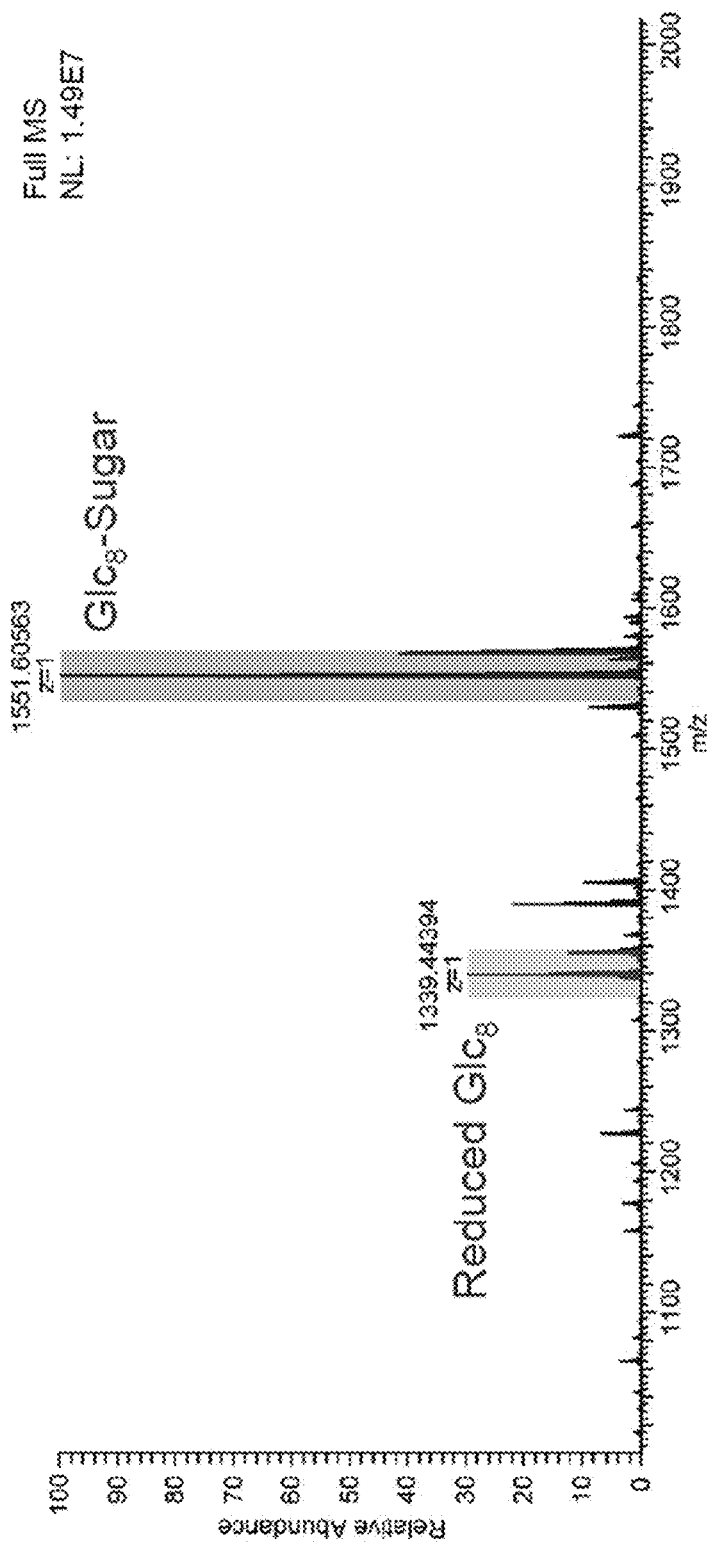
Figure 14:
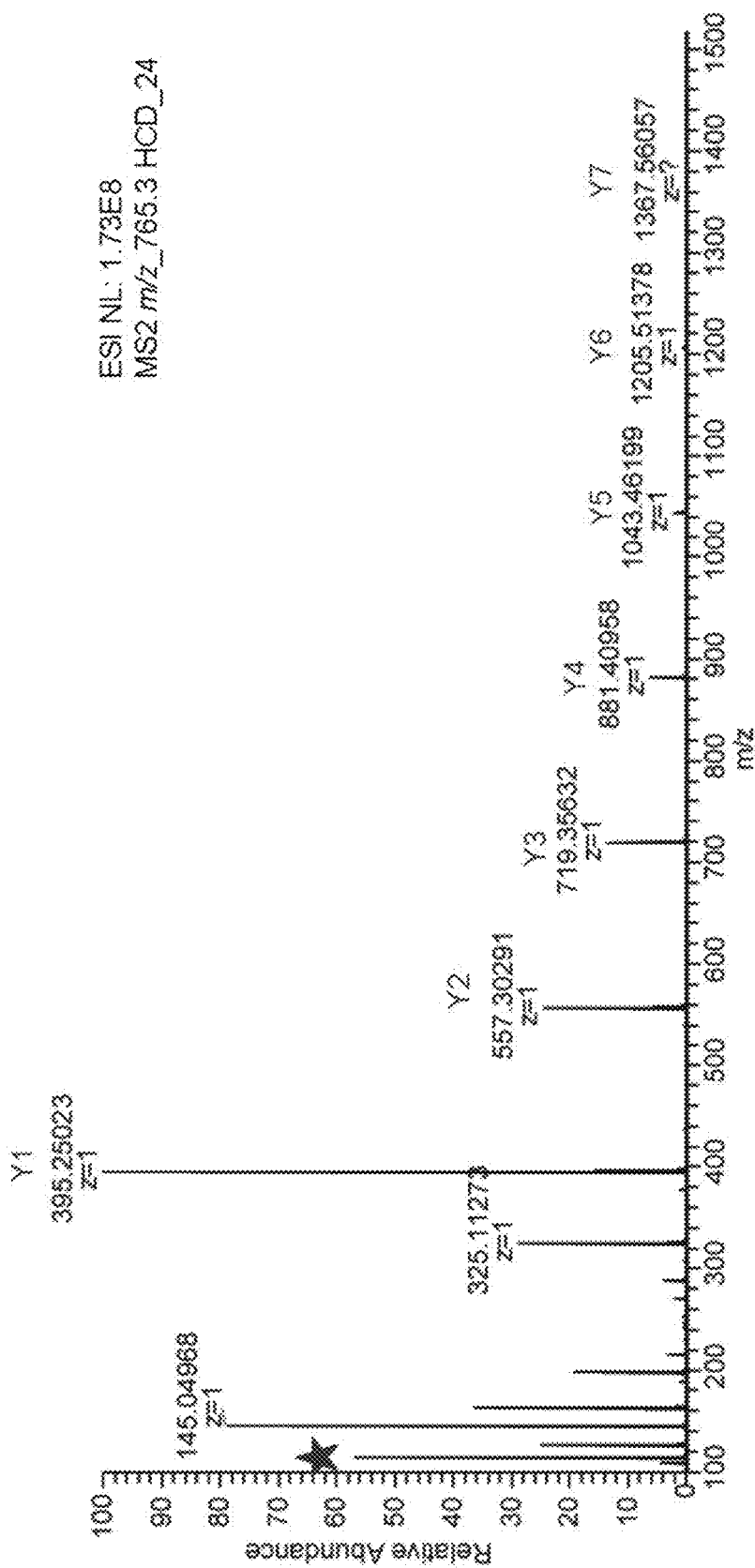
FIG. 14 shows a $MS^2$ fragmentation spectrum of a SUGAR labeled $(Glc)_8$. All the Y ions could be identified with high intensity of the reporter ion (shown at the peak labeled with star) in this example.
Figure 15:
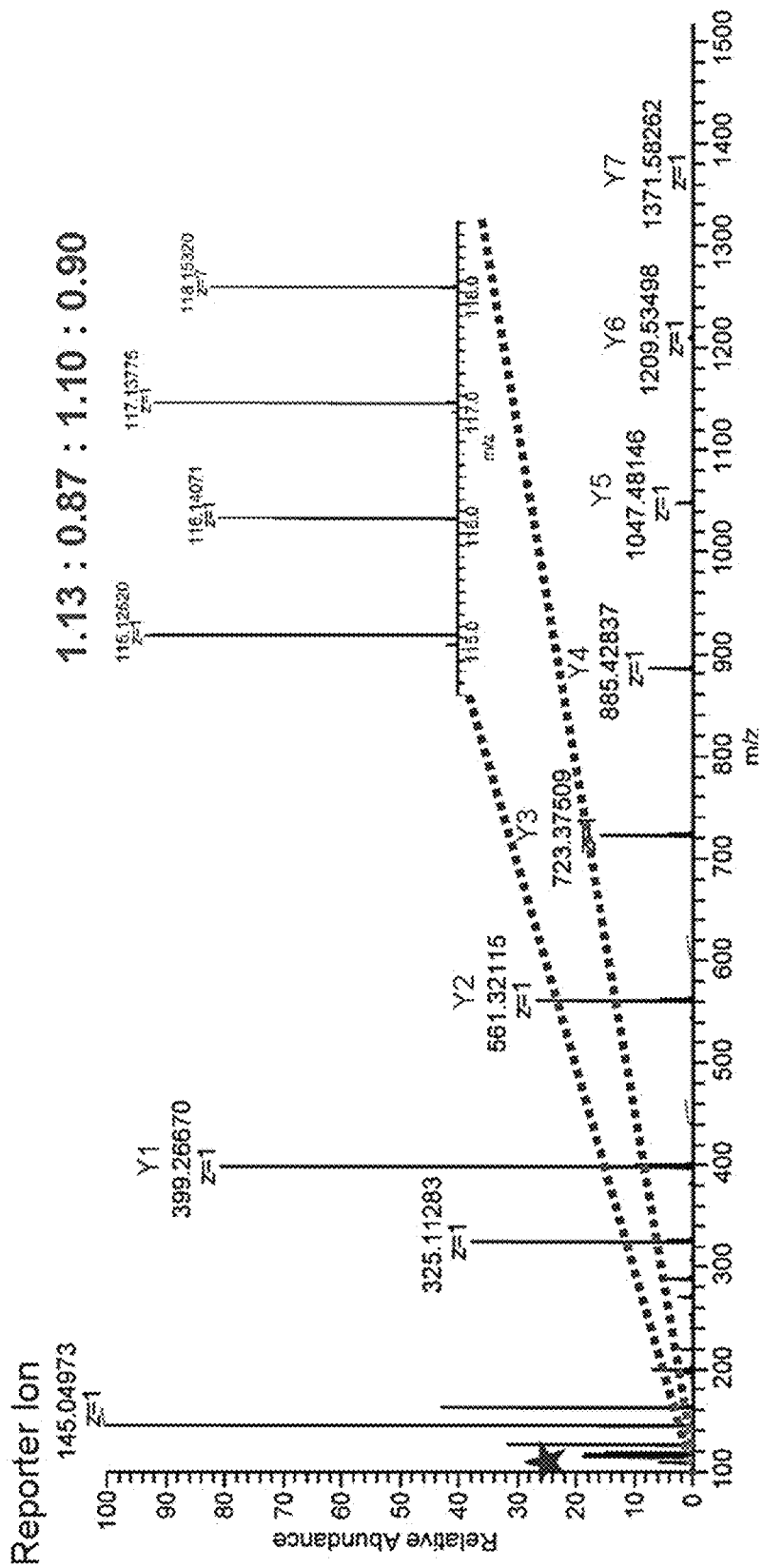
FIGS. 15 and 16 show $MS^2$ fragmentation spectra illustrating quantification accuracy of labeled $(Glc)_8$. Either 1:1:1:1 or 10:1 ratios provide accurate result within a 15% relative error.
Figure 16:
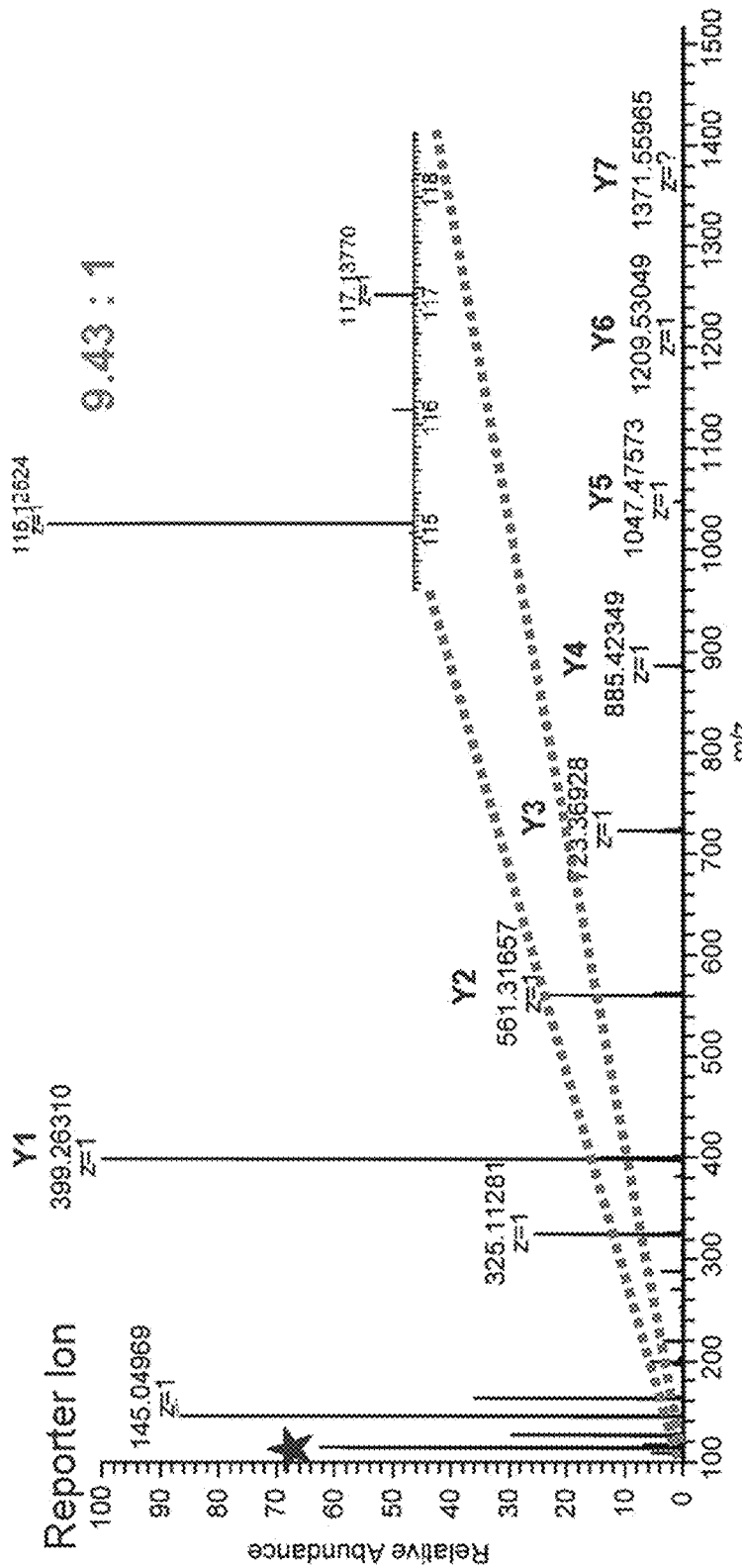

The isotope atoms for the different isobaric tags can be placed at dimethyl group of N-terminus, N atom, carboxylic acid C atom as well as linker positions. For example, isotope configuration of HG-DiLeu could be arranged as FIG. 11 shown for 4-plex isobaric tags. $^{15}N$, $^{13}C$-leucine were used for HG-DiLeu 115 and 117 tags while the rest of two plex used non-isotope leucine as starting material. For dimethylation step, $D_2$-formaldehyde was used for 118 tag to add 4 deuterium atoms at the N-terminus. Sodium cyanoborodeuteride was used for 116 and 117 tags to add 2 deuterium atoms. The balancer was designed by using $^{18}O$ atom at carboxylic acid in the original 4-plex DiLeu. However, the 4 deuterium atom difference between 115 and 118 tags produced several seconds LC retention time shift which could affect quantitation accuracy in isobaric labeling strategy. Thus, $D_2$-glycine methyl ester was used in the 115 and 116 plex tags to decrease the deuterium number difference and improve the quantitation performance. FIG. 11 only shows 4-plex HG-DiLeu synthesis. 12-plex, or higher plexes, is available by adding $^{13}C$ atoms at N-terminus with mass defect and high-resolution mass spectrometer (FIG. 12). A 12-plex system is useful in that it enables triplicate analysis of four different samples.

As the isotope-coded material is often expensive, the reaction yield is critical for the tag synthesis. In the 3-step synthesis, the amidation step might be a low yield reaction since the side chain of leucine would be a steric issue which makes it difficult for EDCI to approach the carboxylic acid as well as the glycine to attack the activated ester. However, the steric issue could be addressed with higher reaction temperature, longer reaction time and stronger condensation reagents, such as PyAOP, HATU, DMTMM. Another potential pitfall is the fragmentation behavior change after connecting a linker. Since the fragmentation process often involves electron transfer, the linkers with electron donating or electron withdrawing group were employed to alter fragmentation behavior.

Performance Evaluation.

Figure 34:
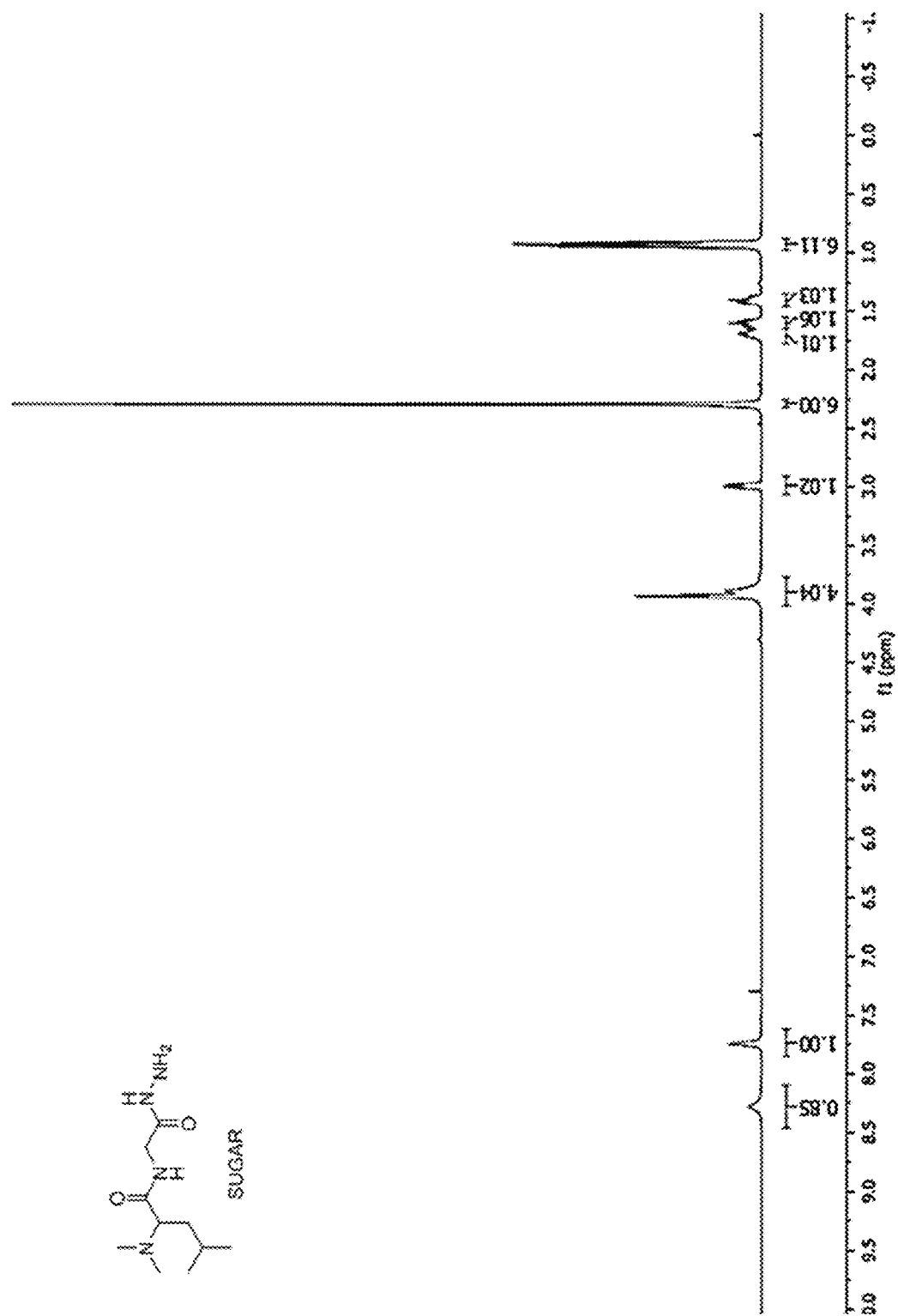
FIG. 34 shows $^1H$ NMR of an exemplary SUGAR tag.
Figure 35:
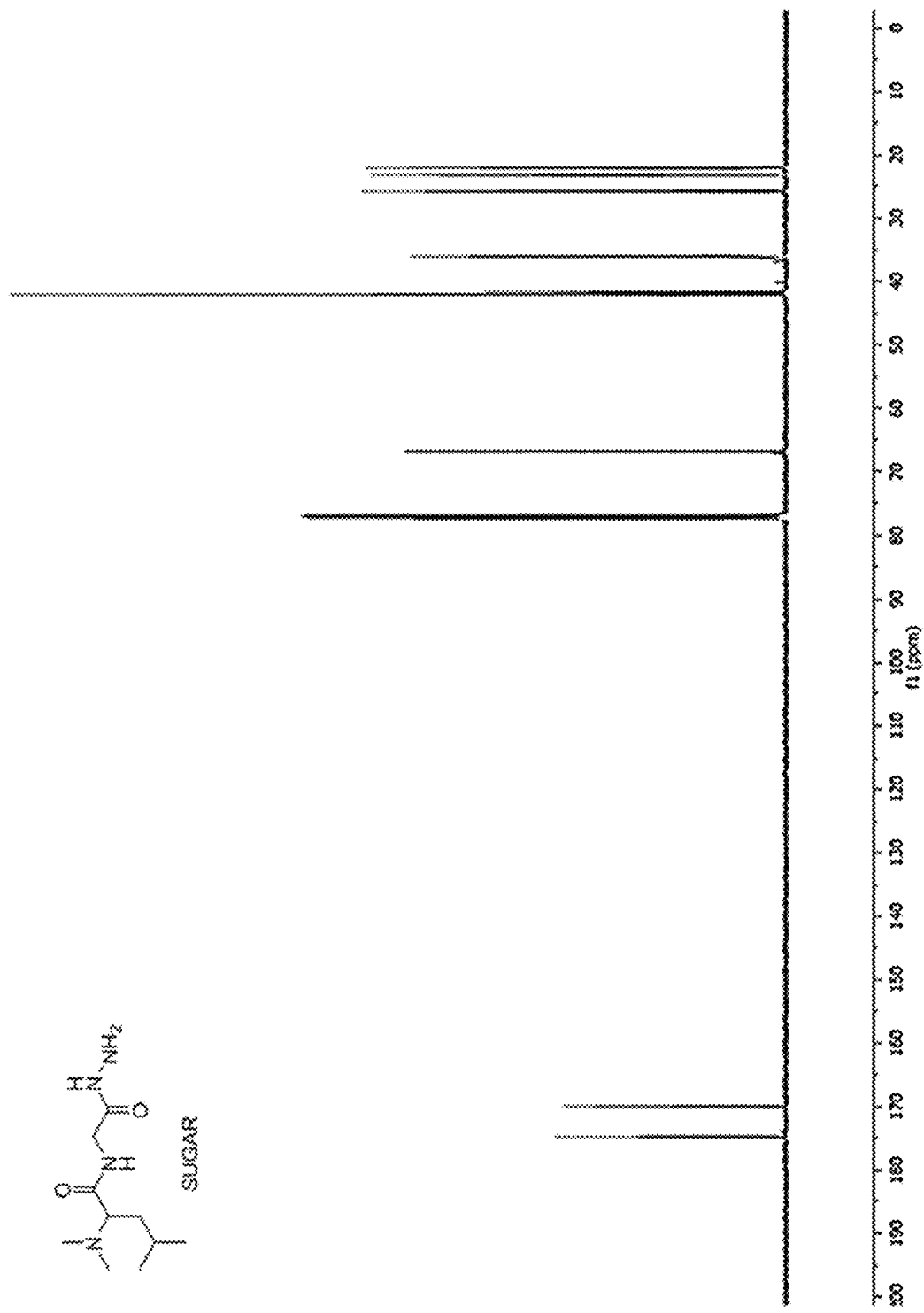
FIG. 35 shows $^{13}C$ NMR of an exemplary SUGAR tag.

After the tags were synthesized ($^1H$ and $^{13}C$ NMR of a SUGAR tag is shown in FIGS. 34 and 35), performance evaluation was conducted to examine the labeling efficiency, fragmentation, quantitation accuracy, as well as ionization properties (FIGS. 13-26). Labeling efficiency is a very important performance metric to evaluate since the complete yield of labeled glycan would provide more information for characterization and less variation for the quantitation result, while low labeling efficiency would limit the detection of low abundance glycans. Also, the variable labeling yield could lead to inaccurate quantitation analysis. As the $MS^2$-based quantitative glycomics relies on the reporter ions produced via fragmentation, the fragmentation behavior is another important aspect to be evaluated. In this study, both labeling efficiency and fragmentation behavior were examined with linear $(Glc)_8$ as the standard.

$(Glc)_8$ was aliquoted to 100 ug for labeling and fragmentation performance evaluation. The labeling reaction employed either imine formation for fast labeling or reductive amination for irreversible labeling. For imine formation labeling, the glycan standard was mixed with 1 mg tag in 100 ul MeOH with 1% FA. The solvent was removed in SpeedVac after 10 min vortex. The labeling reaction was repeated twice. For reductive amination, the glycan standard was mixed with 1 mg tag in 100 ul 30% acetic acid in DMSO containing 1 M $NaBH_3CN$. The labeling reaction was performed for 2 hours at 70° C. After the labeling, sample cleanup was carried out using 1 cc HLB Oasis cartridge. The cartridge was conditioned with 3 ml 95% ACN, 1 ml 50% ACN and 3 ml 95% ACN. Then, the labeling solution was added in the cartridge filled with 1 ml 95% ACN. The cartridge was washed with 6 ml 95% ACN. The labeled glycan was eluted with 1 ml 50% ACN and 1 ml $H_2O$. The elution was dried in SpeedVac and stored in −20° C. for further use. The evaluation of labeling efficiency was carried out with a MALDI-linear ion trap-Orbitrap mass spectrometer. The evaluation of fragmentation behavior was carried out using a Q-Exactive Orbitrap mass spectrometer.

Both H-DiLeu and HG-DiLeu exhibited high labeling efficiency with imine formation which indicated the higher reactivity for hydrazide group. Over 85% yield could be obtained for either H-DiLeu or HG-DiLeu candidates with reductive amination while A-DiLeu could only produce less than 50% labeled glycan. With further development of the labeling strategy, over 95% yield could be achieved for H-DiLeu and HG-DiLeu by stepwise reductive amination. The tag was mixed with glycan in MeOH containing 1% FA. The solvent was removed in SpeedVac after 10 min vortex. The labeling reaction was repeated twice. Then, 100 ul 30% acetic acid in DMSO containing 1 M NaBH3CN was added into the tube and allowed to react for 2 hours at 70° C. The fragmentation behavior was studied for both hydrazide containing DiLeu candidates. The reporter ion was only obtained from HG-DiLeu labeled glycans.

Evaluation of DiLeu Tag Candidates with Glycoprotein Standards.

After the performance evaluation with $(Glc)_8$ standard (FIGS. 13-16), HG-DiLeu was selected as the best candidate while stepwise reductive amination was selected for the labeling reaction. The labeling efficiency, fragmentation behavior for several types of glycans and quantitative accuracy results were evaluated by labeling 4-plex HG-DiLeu with glycoprotein standards.

N-glycans were released from thyroglobulin from bovine thyroid (BTG) using the modified Filter Assisted N-Glycan Separation (FANGS) protocol (Abdul Rahman et al., J Proteome Res, 2014, 13 (3): 1167-76). HG-DiLeu labeling reaction was performed by reductive amination reaction. For MALDI analysis, cotton HILIC SPE microtip was used for sample clean-up and data acquisition was carried out with a MALDI-linear ion trap-Orbitrap mass spectrometer. For ESI analysis, 1 cc Oasis HLB cartridge was used for sample clean-up and data acquisition was performed with a Q-Exactive Orbitrap mass spectrometer. The identification of glycans was performed by accurate mass matching at the $MS^1$ (i.e., full MS) level with fragmentation analysis at the $MS^2$ level. The relative quantitation between different samples was achieved by comparing the intensities of the reporter.

Figure 17:
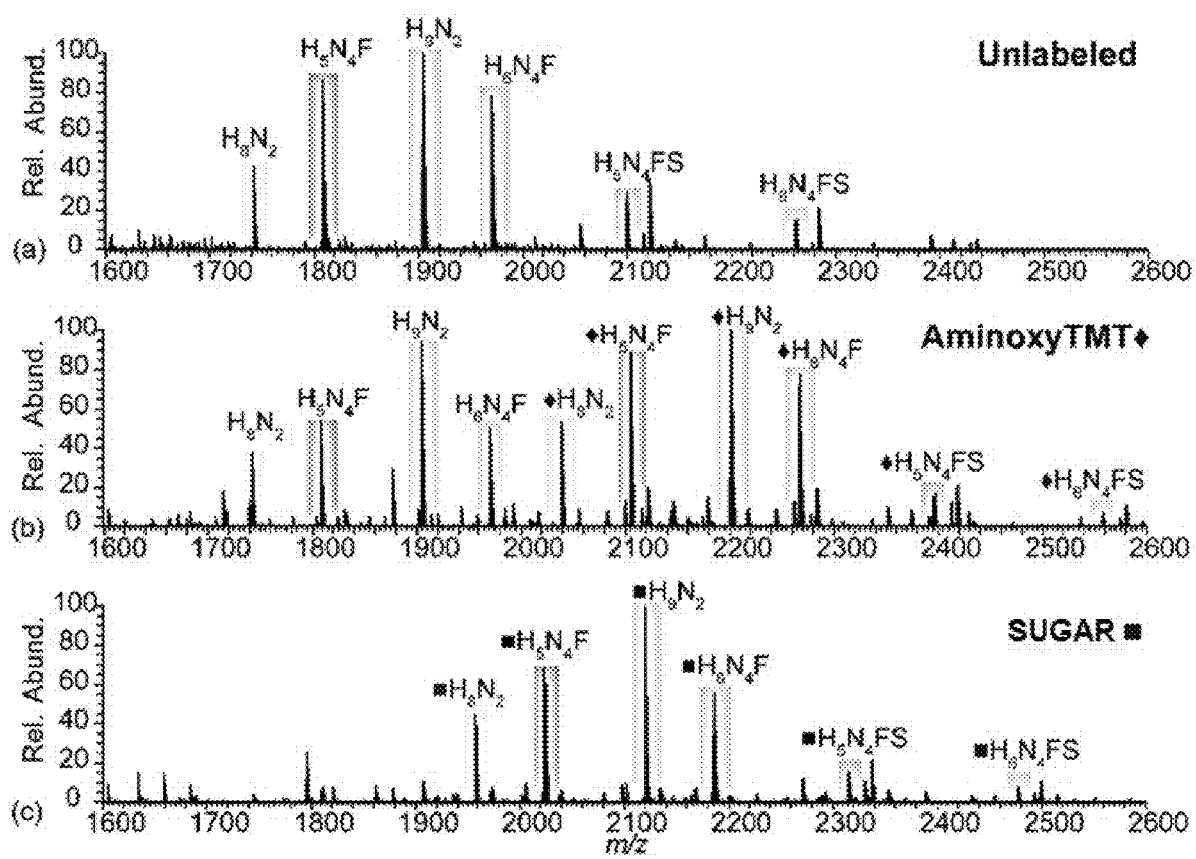
FIG. 17 shows labeling comparison of an AminoxyTMT tag and a SUGAR tag.
Figure 21:
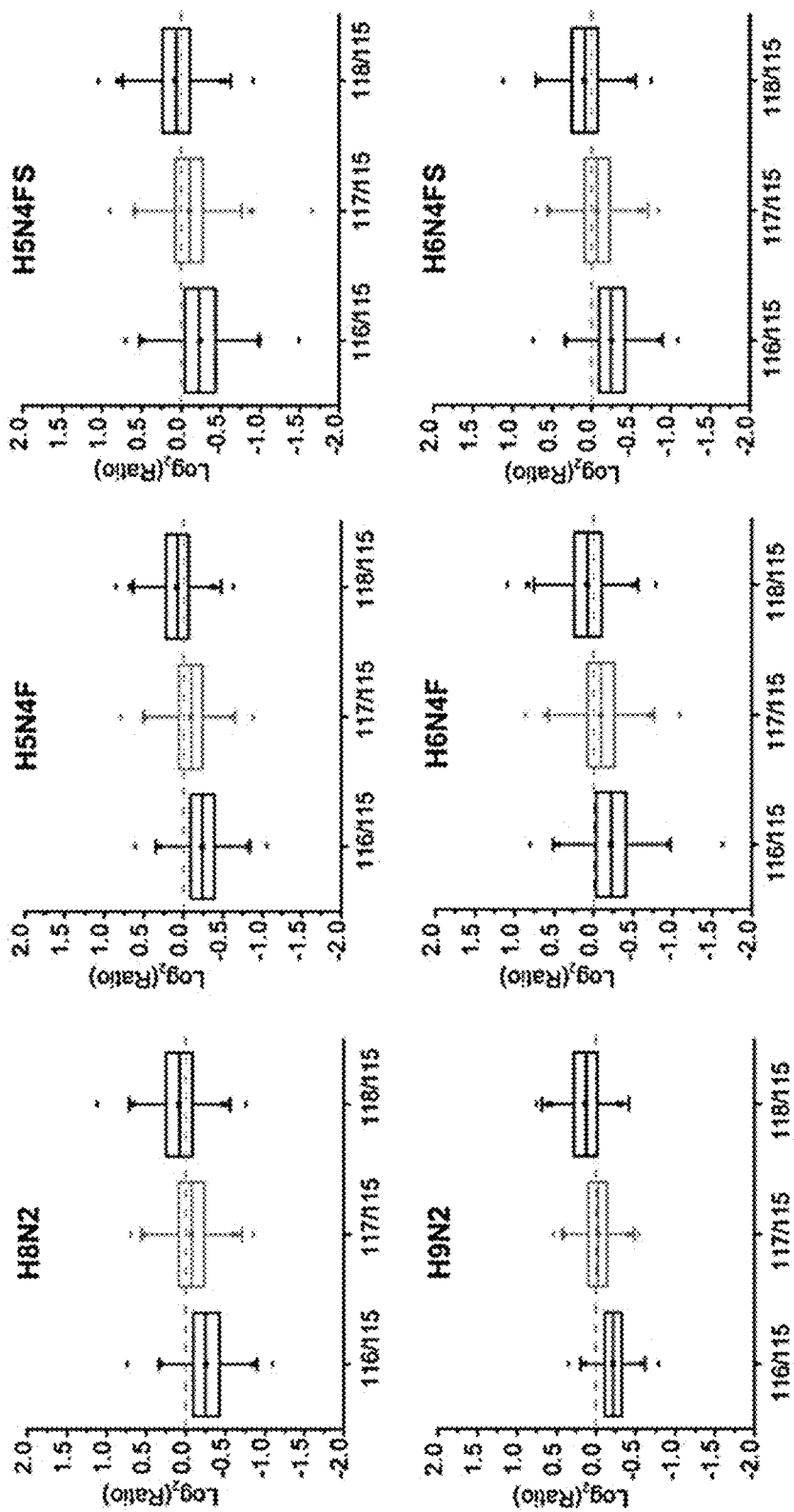
FIG. 21 shows the quantitation accuracy of a 4-plex SUGAR tagging system with various different glycans. The result shows the performance of the SUGAR tagging system with accurate quantification and small deviation.
Figure 22:
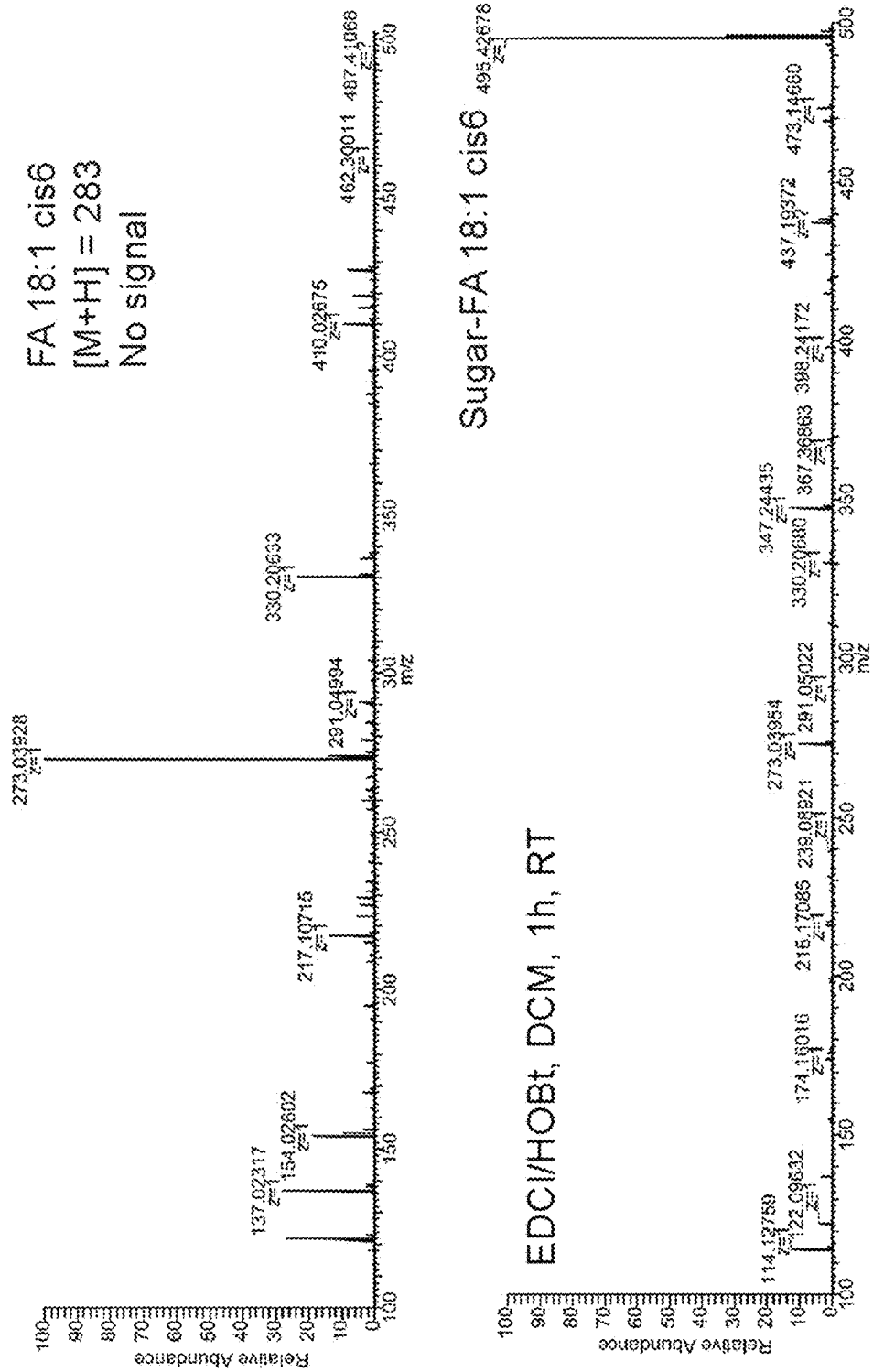
FIGS. 22-23 show charge switch labeling of a fatty acid with a SUGAR tagging system. The free fatty acid could not be identified in positive mode (FIG. 22, panel a), while the SUGAR labeled fatty acid was able to be identified (FIG. 22, panel b). Also, the SUGAR labeled fatty acid was able to produce a suitable reporter ion during fragmentation to facilitate quantitative lipidomics.
Figure 23:
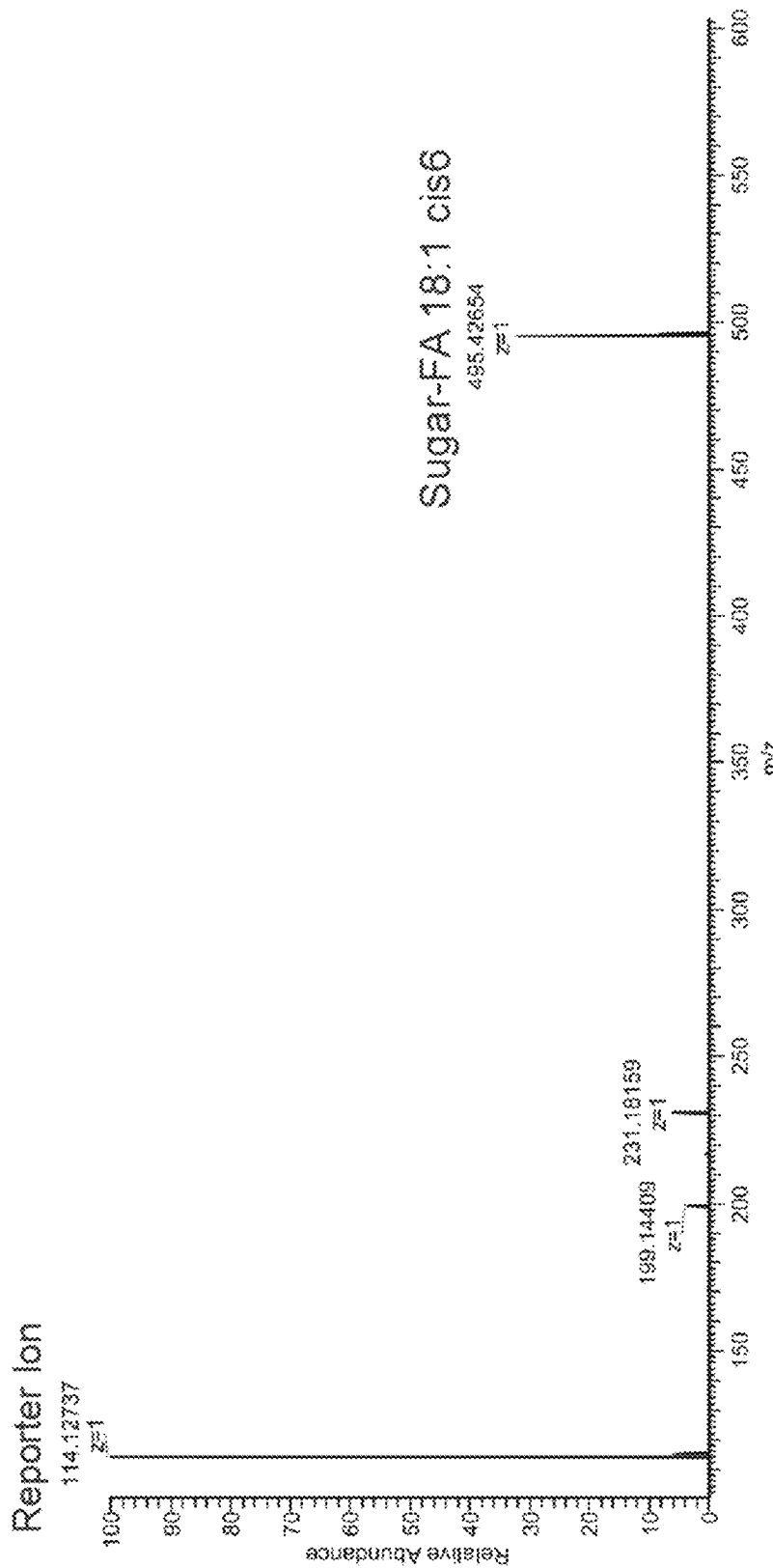
Figure 24:
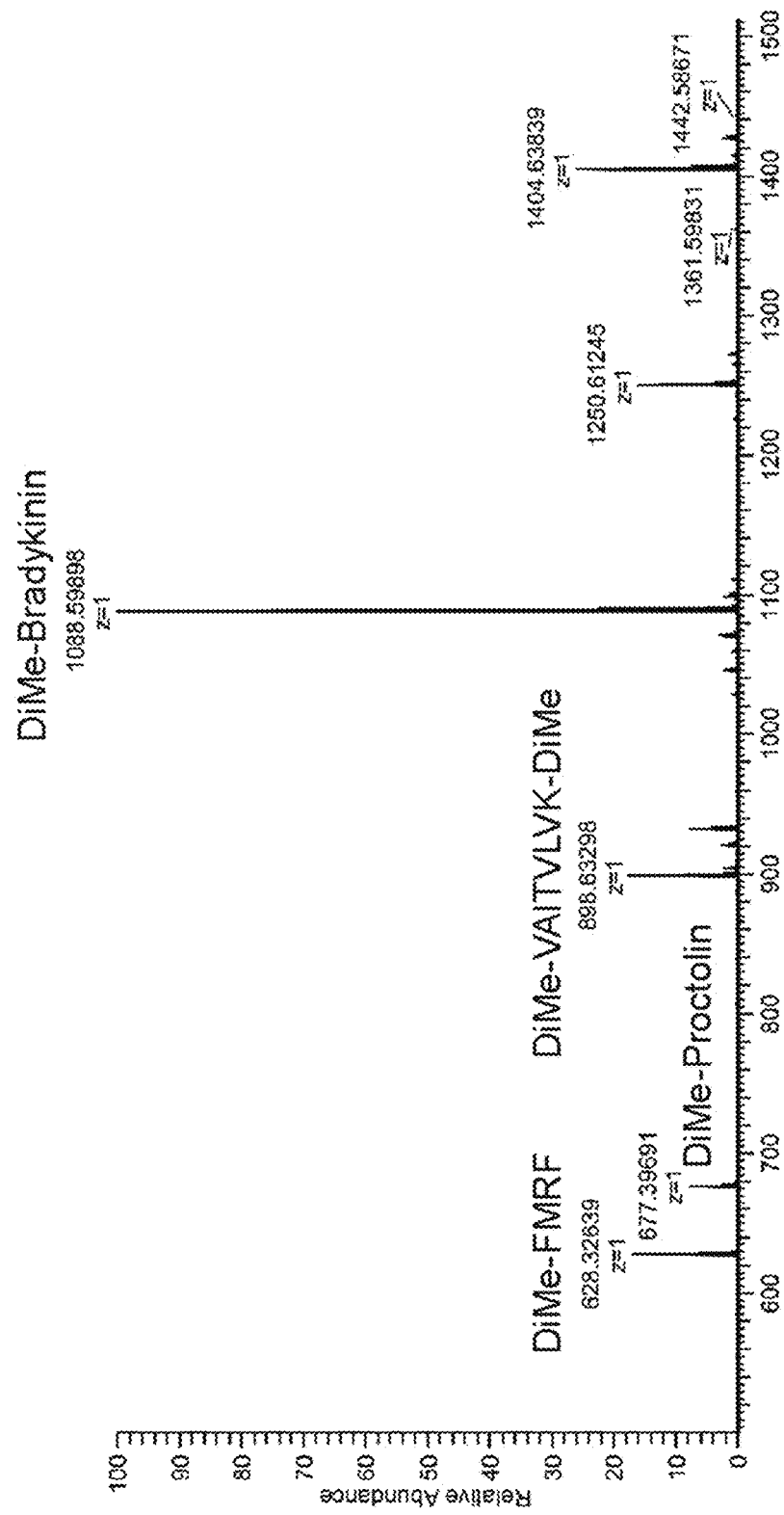
FIGS. 24-25 show dimethylated peptide mixtures (FIG. 24) and the same dimethylated peptide mixtures labeled with a SUGAR tag (FIG. 25).
Figure 25:
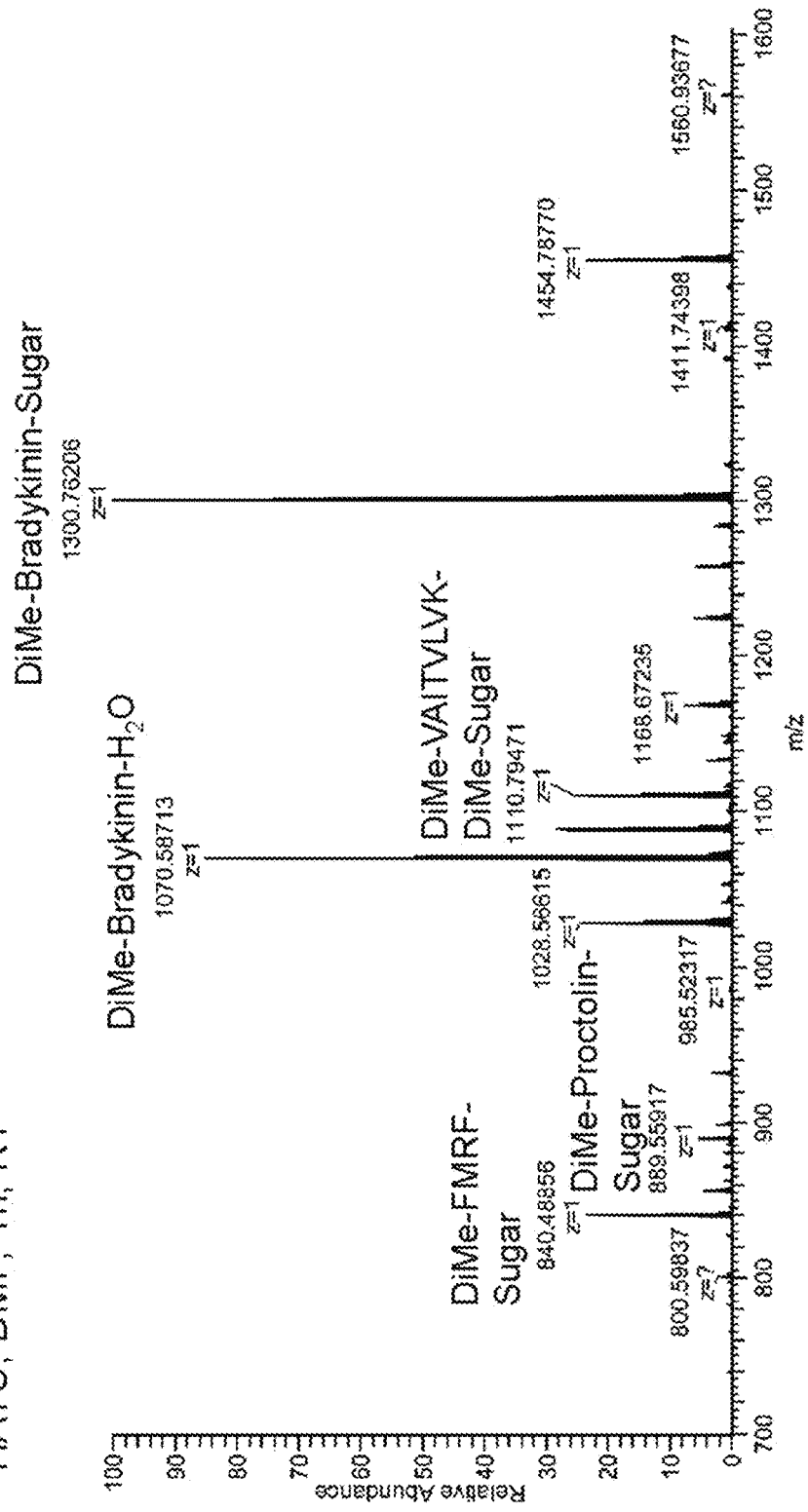
Figure 26:
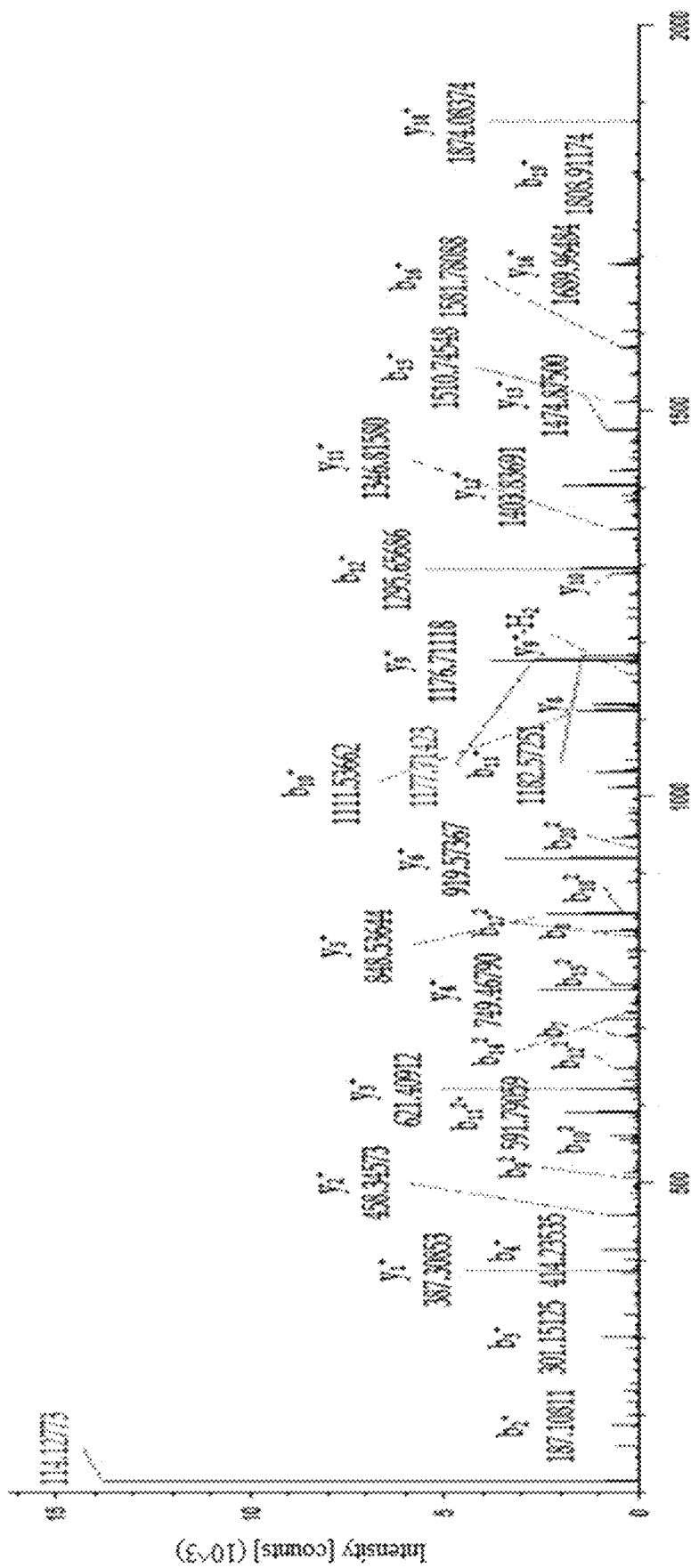
FIG. 26 shows tandem MS fragmentation of SUGAR labeled peptide with extensive backbone b-/y-fragment ions that enabled sequence identification. In this instance the peptide is sANLmAGHWVAISGAAGGLGSLAVQYAk, where the lower case letters represent modifications at the different position: N-term (Dimethyl), M5 (Oxidation), K28 (Dimethyl), C-term (SUGAR-114 tag).

With the stepwise reductive amination strategy, the glycans released from BTG were labeled with HG-DiLeu in high yield (FIG. 17). The fragmentation produced relatively high intensity reporter ions for several types of glycans, especially, 11% comparing to the AminoxyTMT labeled glycan which is only 2% intensity. For the quantitative accuracy experiment, glycans released from the same amount of BTG were labeled with different plex of HG-DiLeu. The preliminary quantitation results showed relatively high accuracy with less than 15% relative error and low standard deviation (FIG. 21).

Other ratios between different plex can be tested to further evaluate the quantitation accuracy, such as 10:5:1:1 and 1:1:5:10. Also, different glycoproteins can be used to evaluate the performance of the HG-DiLeu tags with more types of glycans. Cells or human serum could be used for even more complex sample analysis. There are several potential pitfalls including sialic acid loss during labeling reaction and limited glycan release yield from complex samples. One strategy to reduce sialic acid loss is amidation for carboxylic acid. After the acid is converted to amide, the stability is greatly enhanced. Since the sialic acid loss happens in acidic solution, recently developed reductive amination labeling condition could be used, such as methanol, ethanol and tetrahydrofuran (Anumula, K. R., Anal Biochem, 1994, 220 (2): 275-83; and Evangelista et al., Electrophoresis, 1996, 17 (2): 347-51). In general, glycans are released from glycoproteins with PNGaseF. However, the glycan release yield is not complete because the steric structure makes it difficult for enzyme to access the glycosylation site. Complex glycoproteins could be digested with trypsin. Then PNGase F could be used to release glycans from glycopeptides to improve the overall glycan yield.

Example 2—Synthesis of Probes for Quantitative Glycomic Analysis

Materials and Reagents.

Methanol (MeOH), ethanol (EtOH), acetonitrile (ACN), dichloromethane (DCM), dimethyl sulfoxide (DMSO), acetic acid (AA), formic acid (FA) and water were purchased from Fisher Scientific (Pittsburgh, Pa.). Formaldehyde, sodium cyanoborohydride, N-(3-Dimethylaminopropyl)-N'-ethylcarbodiimide hydrochloride (EDCI), N-methylmorpholine (NMM), 1-Hydroxybenzotriazole hydrate (HOBt), glycine methyl ester hydrochloride, hydrazine, triethylammonium bicarbonate buffer (TEAB, 1.0 M), tris(2-carboxyethyl) phosphine hydrochloride (TCEP) were purchased from Sigma-Aldrich (St. Louis, Mo.). PNGase F was purchased from Promega (Madison, Wis.). Oasis HLB 1 cc (30 mg) extraction cartridges were purchased from Waters Corporation (Milford, Mass.). Bovine thyroglobulin (BTG) was provided by Thermo Fisher Scientific (Rockford, Ill.). Microcon-30 kDa centrifugal filters (30K MWCO) were purchased from Merck Millipore Ltd. (Darmstadt, Germany). PolyGLYCOPLEX A™ beads (3 μm) were purchased from PolyLC Inc. (Columbia, Md.). Fused silica capillary tubing (inner diameter 75 μm, outer diameter 375 μm) was purchased from Polymicro Technologies (Phoenix, Ariz.). All reagents were used without additional purification.

Synthesis of SUGAR Tags.

Formaldehyde (285 μL, 37% w/w) was added to a stirred solution of sodium cyanoborohydride (120 mg) and L-leucine (100 mg) in water (5 mL) at 0° C. After being stirred at room temperature for 1 h, the reaction mixture was concentrated in vacuo. Purification of the residue through column chromatography on silica gel (eluted with DCM/MeOH) afforded dimethyl leucine as a white solid.

Dimethyl leucine was dissolved in 10 mL DCM with 125 mg glycine methyl ester hydrochloride, 192 mg EDCI, 153 mg HOBt and 500 μL NMM. After being stirred at room temperature overnight, the reaction was purified with a short column to remove solid byproduct. The crude residue was concentrated in vacuo and dissolved in 10 mL EtOH with 10% hydrazine. After being stirred for 3 hours at room temperature, the purification through column chromatography on silica gel (eluted with DCM/MeOH) afforded SUGAR tag as a light-yellow oil (117 mg, 67% yield for 3 steps). The 4-plex SUGAR tags were synthesized with heavy isotope encoded starting materials (see FIG. 11).

$^1$H NMR (400 MHz, CDCl3): δ 0.93 (dd, J=9.2, 6.5 Hz, 6H), 1.50 (dddd, J=81.9, 13.4, 8.5, 5.3 Hz, 2H), 1.65-1.77 (m, 1H), 2.29 (s, 6H), 2.94-3.05 (m, 1H), 3.71-4.04 (m, 4H), 7.74 (t, J=6.0, 1H), 8.28 (s, 1H). $^{13}$C NMR (100 MHz, CDCl3): δ 22.1, 23.3, 25.2, 36.1, 41.6, 42.1, 66.8, 170.0, 174.7.

Human Serum Protein Preparation.

The Health Sciences Institute Review Board of the University of Wisconsin-Madison granted the permission to perform this study (2015-0864). Treatment was conducted according to protocols AALL1131 or AALL0932. Serum samples from three B-cell acute lymphoblastic leukemia (ALL) pediatric patients were collected at the following time points: before chemotherapy and at 1 month, 3 months, and 6 months after the first day of consolidation chemotherapy. The concentration of serum protein was determined by microBCA assay.

N-Glycan Release by Filter-Aided N-Glycan Separation (FANGS).

N-glycans of protein samples were released using FANGS with minor modifications (Abdul Rahman et al., J Proteome Res 2014, 13 (3): 1167-76). Briefly, protein samples were dissolved at a concentration of 1 µg/µL in 0.5 M TEAB buffer. TCEP (0.5 M, 5 µL) was added to the solution, which was then heat-denatured by switching sample tubes between 95° C. and room temperature water baths for 4 times (15 seconds each). A 30 K MWCO filter was used to exchange 200 µL of 0.5 M TEAB buffer for 3 times. The prepared protein samples on the MWCO filter were then incubated with 4 µL PNGase F and 96 µL 0.5 M TEAB for 16 h at 37° C. water bath. The released glycosylamines were separated from the de-glycosylated proteins by centrifuging. Glycosylamines were collected into bottom tube and the de-glycosylated proteins remained above the filter. The filter was washed with 100 µL 0.5 M TEAB buffer for reconstituting the de-glycosylated proteins. Both fractions were dried in vacuo. To convert glycosylamine to glycan (with free reducing end), 200 µL of 1% AA was added to the glycosylamine fraction, incubated for 4 h and dried in vacuo.

N-Glycan SUGAR Labeling and Cleaning Up.

SUGAR labeling reactions were performed using a stepwise strategy. Released N-glycans were mixed with 1 mg SUGAR tag in 100 µL MeOH containing 1% FA. After 10 min incubation, the solvent was removed in vacuo. Then, 100 µL 1 M NaBH$_3$CN in DMSO: AA (7:3 v/v) was added to N-glycans. The reduction was performed at 70° C. for 2 h. The labeling reaction was cooled down before clean-up.

Oasis HLB 1 cc cartridge was used to remove excess labels and purify the labeled N-glycans. The cartridge was conditioned with 1 mL of 95% ACN, 1 mL of water, and 1 mL of 95% ACN. The crude reaction mixture was quickly loaded to the conditioned cartridge which was pre-filled with 1 mL of 95% ACN. The cartridge was then washed with 1 mL of 95% ACN for 3 times, and the labeled N-glycans were eluted with 1 mL 50% ACN and 1 mL water. The eluting fractions were combined, dried in vacuo, reconstituted in 50 µL of 75% ACN, and analyzed by MALDI-MS or LC-MS/MS immediately.

MALDI-MS Analysis for Labeling Efficiency Calculation.

Samples were prepared by premixing 1 µL of SUGAR-labeled N-glycans with 1 µL 2,5-dihydroxy benzoic acid matrix (150 mg/mL in 2% N, N-dimethylaniline, 49% MeOH and 49% water), and 1 µL of each matrix/sample mixture was spotted onto the MALDI target plate. A MALDI-LTQ-Orbitrap XL mass spectrometer (Thermo Scientific, Bremen, Germany) was used for characterizing labeling efficiency. Ionization was performed using a laser energy of 15 µJ. Spectra were acquired in the Orbitrap mass analyzer within a mass range of m/z 1,000-4,000 at a mass resolution of 30 K (at m/z 400).

LC-MS/MS Analysis.

A self-fabricated nano-HILIC column (15 cm, 75 m i.d., 3 µm PolyGlycoPlex A HILIC beads) was used for glycan separation. A Dionex Ultimate 3000 nanoLC system was coupled to Q Exactive HF Hybrid Quadrupole-Orbitrap Mass Spectrometer (Thermo Scientific, Bremen, Germany) for all LC-MS/MS analyses. Mobile phase A was water with 0.1% FA, and mobile phase B was ACN with 0.1% FA. The flow rate was set at 0.3 µL/min, and the injection volume was 2 µL. The following gradient was used (time, % mobile phase B) unless otherwise specified: (0 min, 75%), (18 min, 75%), (78 min, 15%), (78.1 min, 10%), (90 min, 10%), (90.1 min, 75%), (100 min, 75%).

The following MS parameters were used for all data acquisition in this example. Samples were ionized in positive ion mode with a spray voltage of 2 kV. S-lens RF level was set to be 55, and capillary temperature was set to be 275° C. Full MS scans were acquired at m/z 500-2000 with resolving power of 30 K (at m/z 200). Maximum injection time of 100 ms, automatic gain control (AGC) target value of 1 e6, and 1 microscan were used for full MS scans. Top 20 data-dependent MS$^2$ analysis was performed at a resolving power of 15 K (at m/z 200) with collision-induced dissociation (CID) operating with a normalized collision energy of 30. The first mass was fixed at m/z 110, and dynamic exclusion of acquired precursors was set to 30 sec with a ±10 ppm tolerance.

N-Glycan Data Analysis.

SUGAR-labeled N-glycans were identified by accurate mass matching. A peak list was exported and compared against an in-house database including most possible combinations of N-glycan units (Hexose (H), HexNAc (N), Fucose (F), and NeuAc (S)) with a mass tolerance of 10 ppm. Reporter ion intensities in MS$^2$ were used for relative quantification. Microsoft Excel was used for calculations and statistical analyses.

Results and Discussion.

With the successful development of N,N-dimethyl leucine tags (DiLeu) for quantitative proteomics by N-terminal labeling, the dimethyl leucine structure has been shown to produce abundant backbone fragments with high-intensity reporter ions for quantitative analysis (Xiang et al., Anal Chem 2010, 82 (7): 2817-25; Frost et al., Rapid Commun Mass Spectrom 2015, 29 (12): 1115-24; and Frost et al., Anal Chem 2015, 87 (3): 1646-54). To implement conjugation with reducing end of glycans, the structure of SUGAR tags consists of a hydrazide as the reactive group with glycine as a balancer. Using naturally-occurring amino acids as building blocks with straightforward functional group transformations, SUGAR tags can be synthesized in three steps (Scheme 4) with 67% overall yield:

Scheme 4.

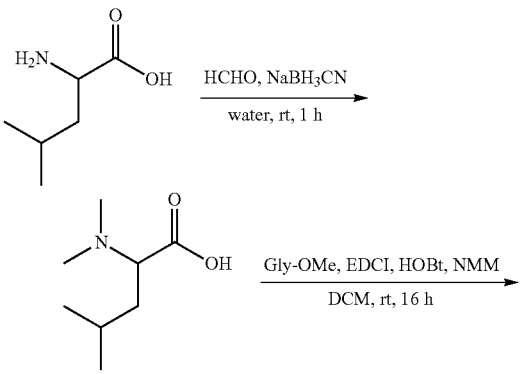

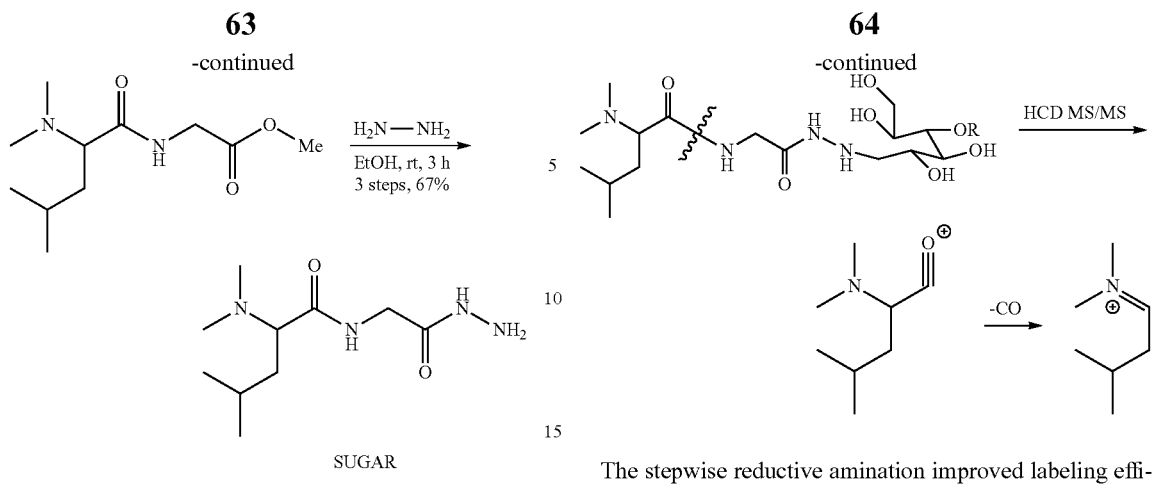

Figure 28:
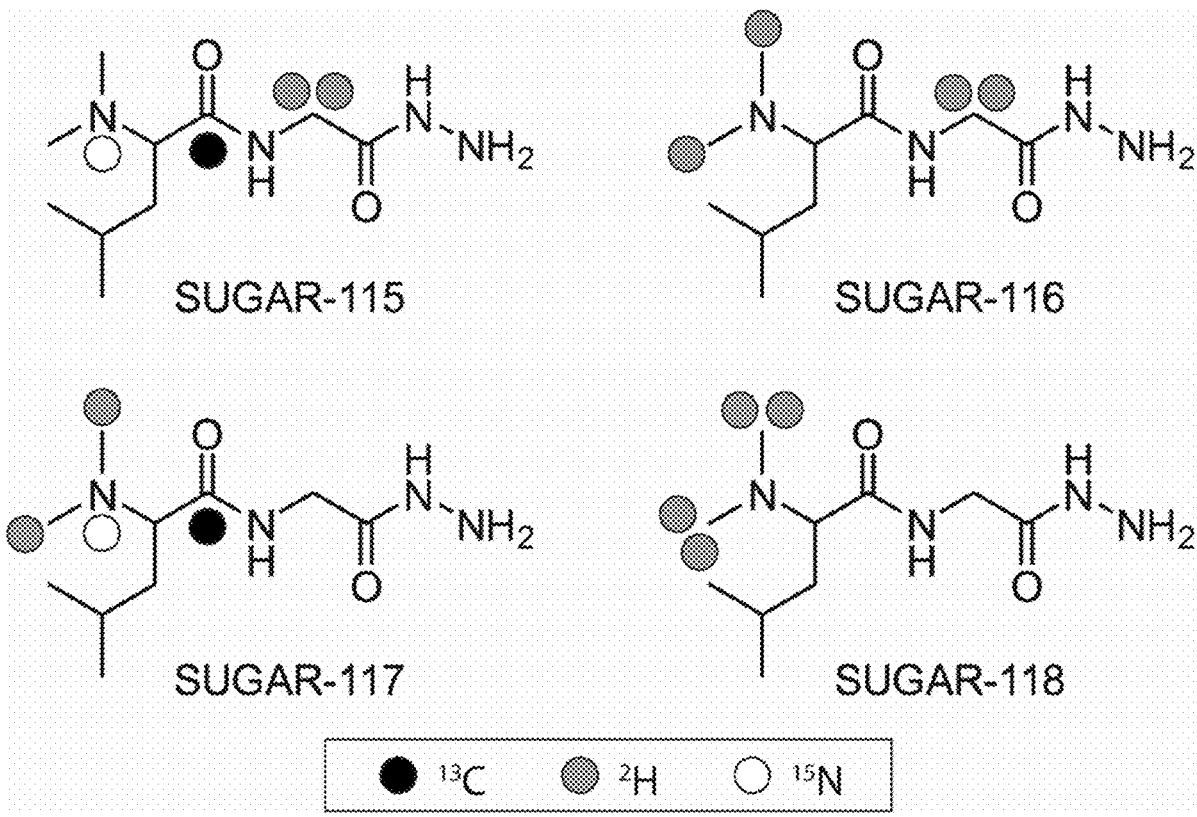
FIG. 28 shows the structure and isotope configurations of exemplary 4-plex SUGAR tags. Black dots: $^{13}C$, grey dots: $^{2}H$, white dots: $^{15}N$.
Figure 31:
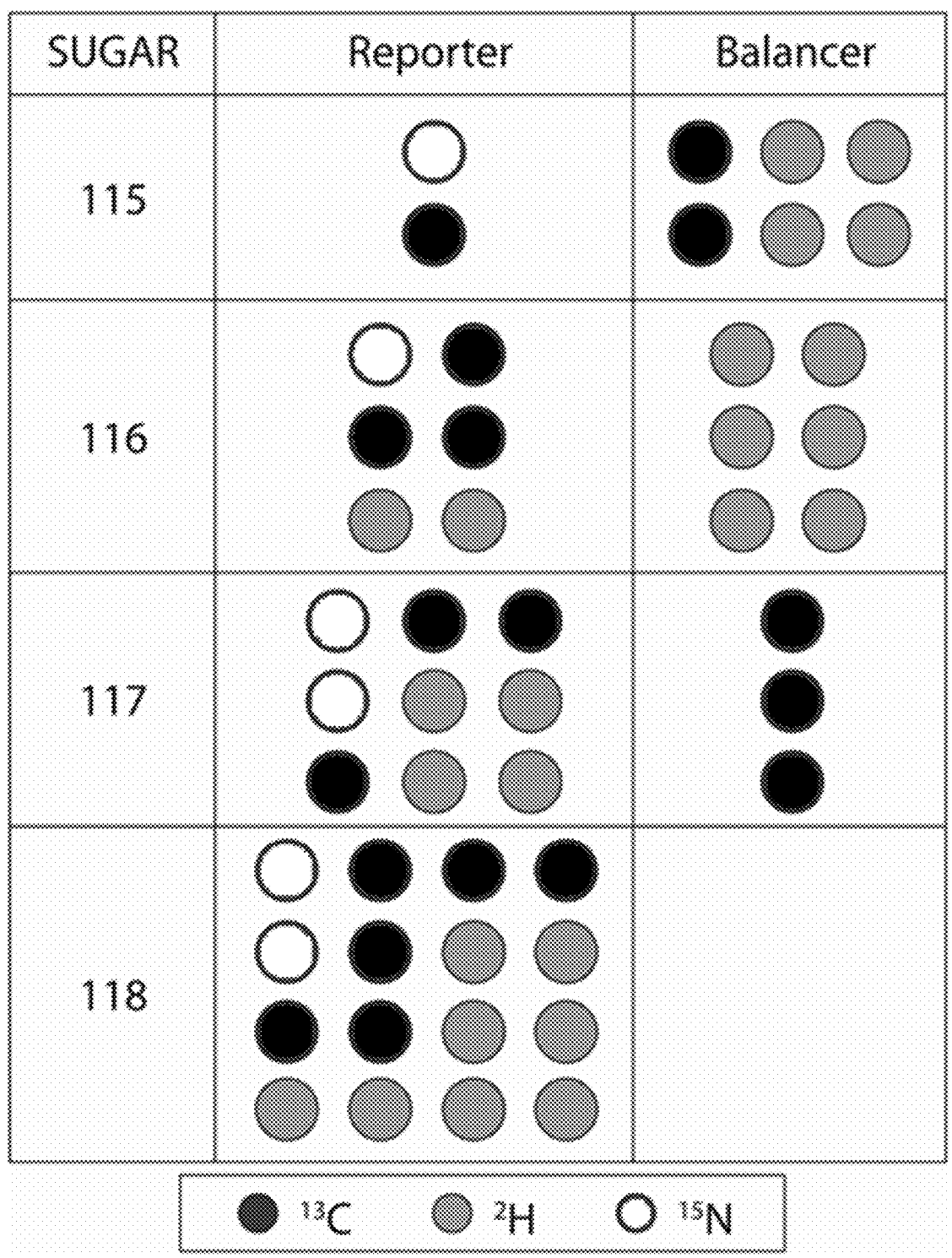
FIG. 31 illustrates exemplary isotope configurations of 12-plex SUGAR tags. Black dots: $^{13}C$, grey dots: $^{2}H$, white dots: $^{15}N$.

In addition, the amino acid building blocks offer various commercially available isotope configurations to enable multiplexing capacity. By incorporating different heavy isotopes, 4-plex SUGAR tags with reporter ion mass difference of 1 Da can be readily synthesized and are shown in FIG. 28. The multiplexing capacity can be further increased to 12-plex by employing mass defect concept (FIG. 31). However, the subtle mass differences between reporter ions require higher resolving power. Future efforts will demonstrate the utility of 12-plex tags for high throughput quantitative analysis.

Hydrazide chemistry is a commonly used conjugation for glycan reducing end labeling which converts hydrazide to hydrazone group. However, the reversible nature of hydrazide chemistry makes complete conjugation arduous. Thus, an alternative irreversible reductive amination is used for glycan reducing end labeling. Despite the high reactivity of the hydrazide group, a high concentration of a reducing agent, such as 1 M NaBH$_3$CN, can reduce glycans prior to hydrazone formation and yield reduced glycan. To further improve labeling efficiency with minimal sample loss, a stepwise reductive amination has been developed. Maltooctaose standard was mixed with SUGAR tag in methanol with 1% formic acid for 10 minutes to complete hydrazone formation. Then, reduction was performed with NaBH$_3$CN in 7:3 (v/v) dimethyl sulfoxide:acetic acid to achieve complete labeling (Scheme 5):

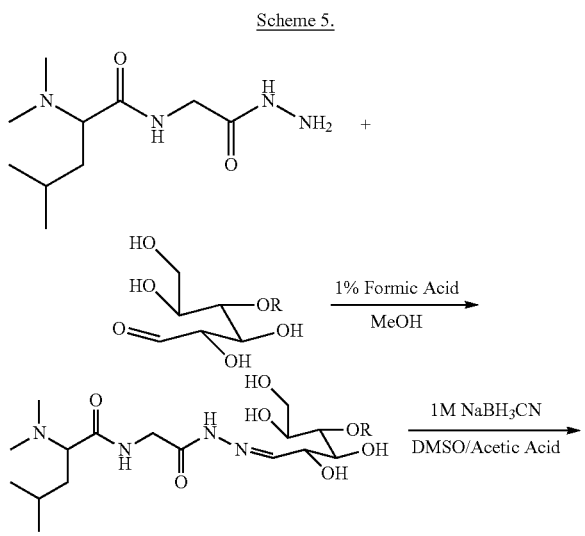

Figure 32:
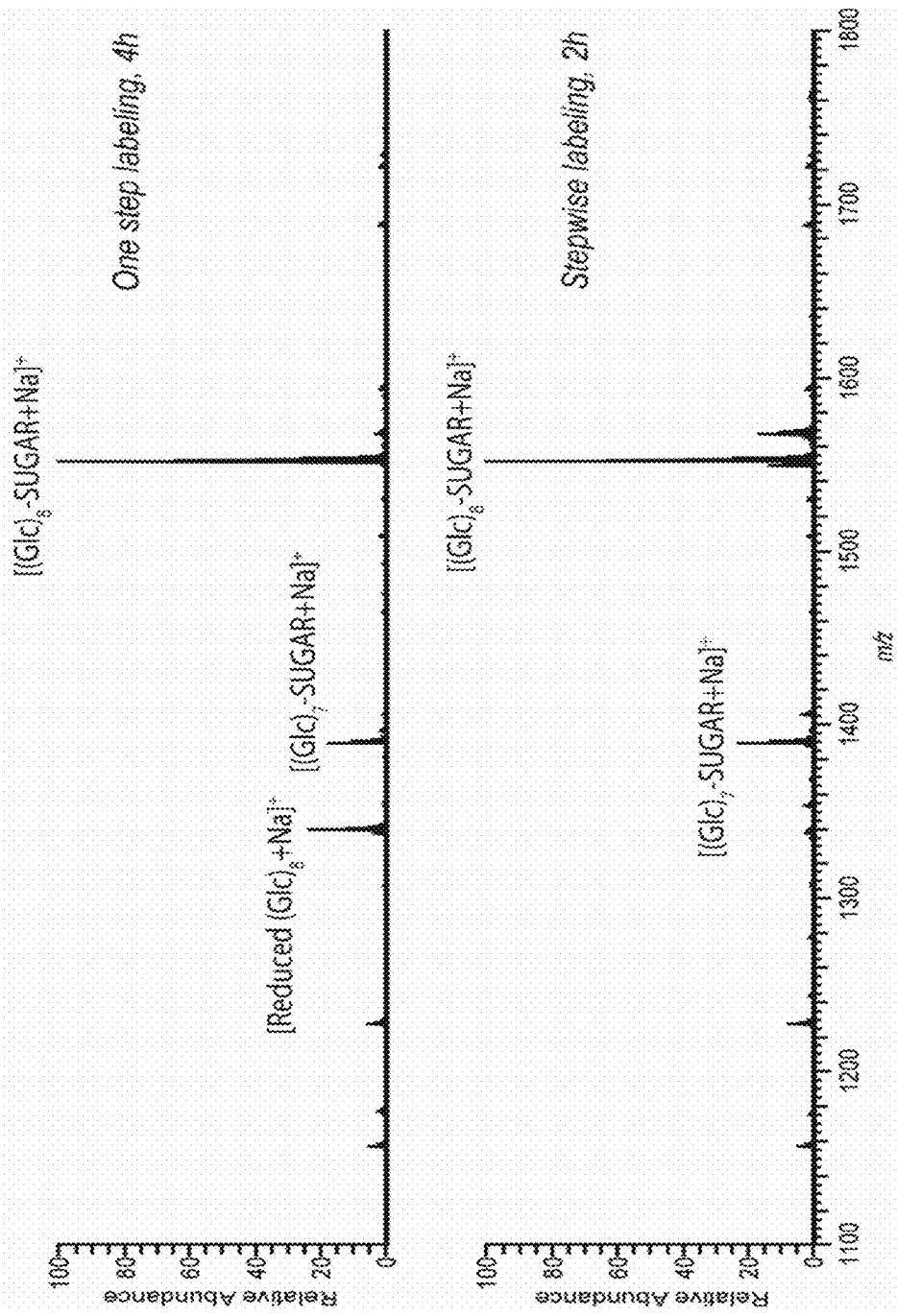
FIG. 32 shows MALDI-MS spectra of one step labeling and stepwise labeling. With stepwise labeling, higher labeling efficiency was observed in half the labeling time with minimal glycan reduction.

The stepwise reductive amination improved labeling efficiency by preventing glycan reduction prior to hydrazone formation and reduced labeling time by half (FIG. 32).

Figure 18:
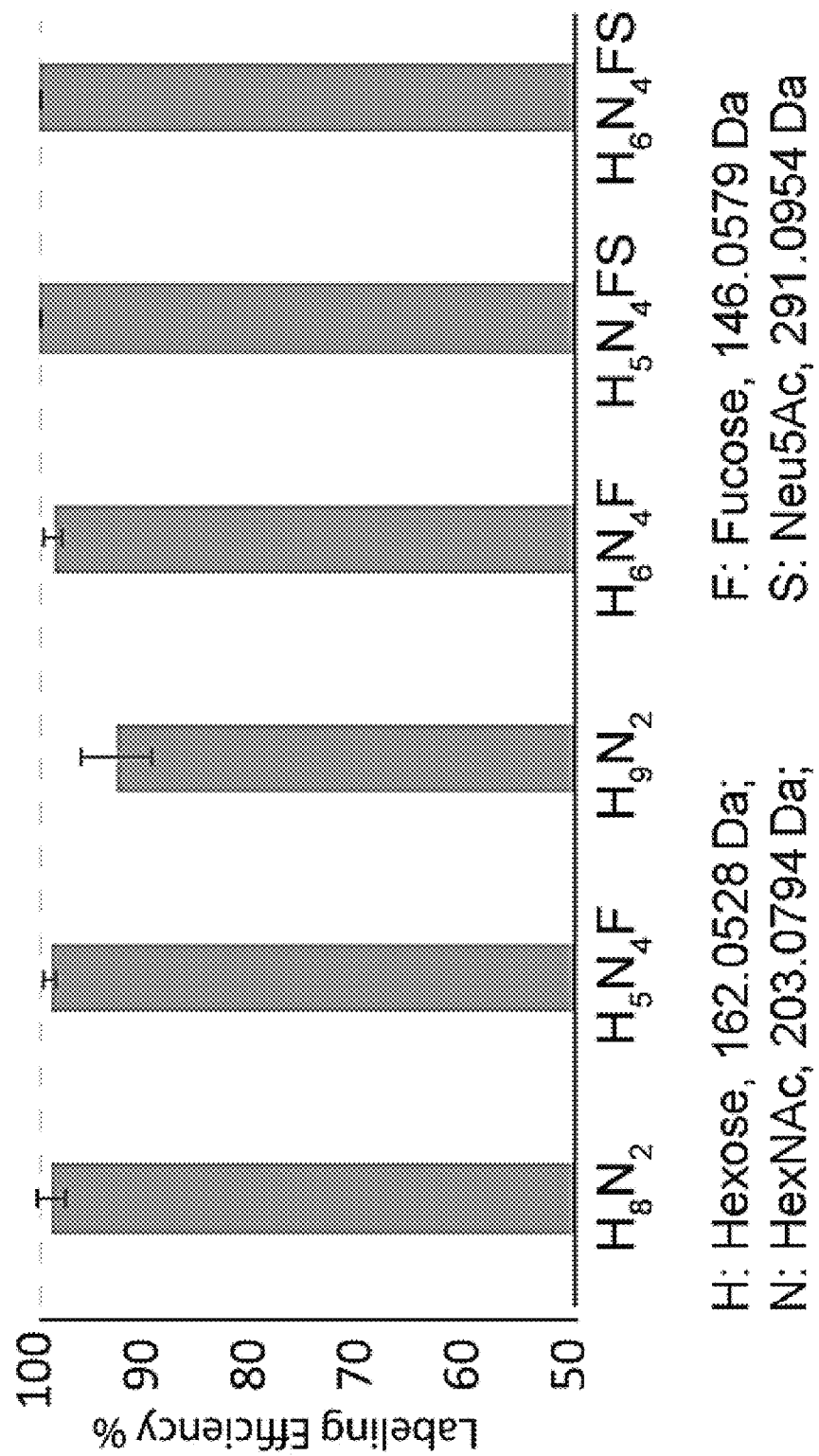
FIG. 18 illustrates the labeling efficiency of the SUGAR tag of FIG. 17 with various different glycans. All types of glycans show nearly complete labeling to facilitate quantitative glycomics.
Figure 27:
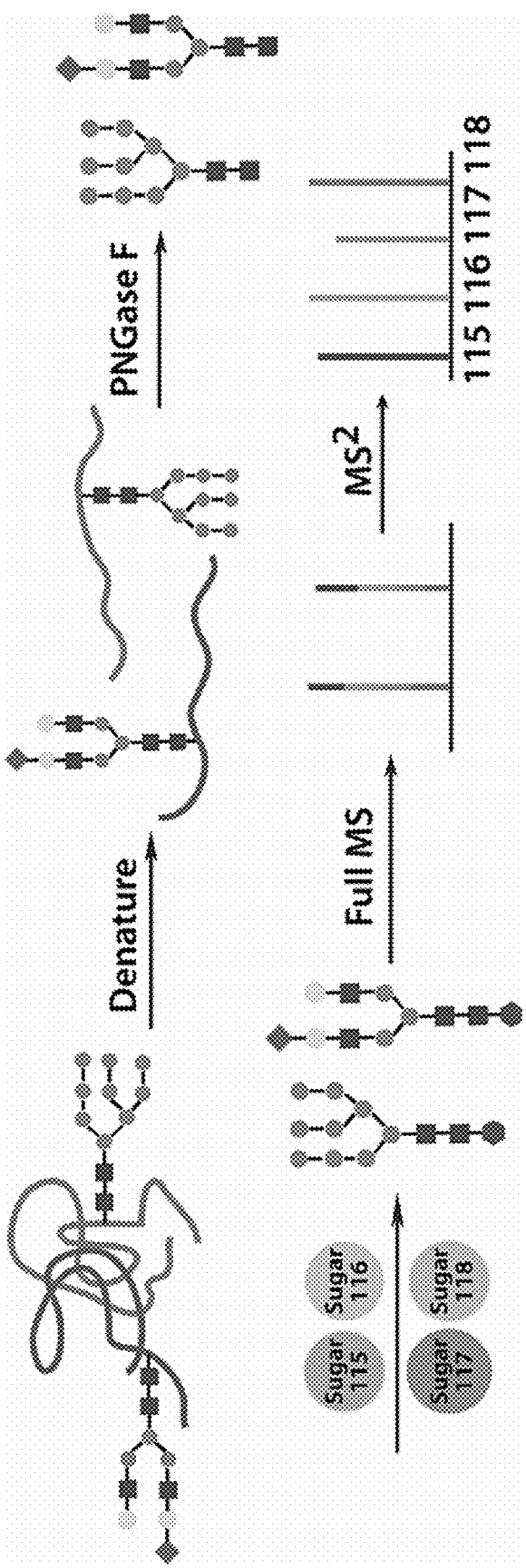
FIG. 27 shows a workflow for quantitative analysis of a glycosylated protein (e.g., bovine thyroglobulin) with a 4-plex HG-DiLeu (SUGAR) tagging system in an embodiment of the present invention. The protein is denatured and the glycans released from the peptide using PNGase F. The glycans are then reacted with the tagging reagents followed by MS analysis.

SUGAR tag with stepwise reductive amination was further applied to the labeling of bovine thyroglobulin (BTG) standard. The workflow is shown in FIG. 27. N-glycans released from BTG by PNGase F were labeled with SUGAR tags. Under optimized labeling conditions, SUGAR tags offer nearly complete labeling for different types of glycans including high mannose, complex/neutral, fucosylated, and acidic glycans. FIG. 17 highlights several N-glycans labeling comparisons. The labeling efficiencies for other N-glycans are expected to be similar due to same shared core structure of N-glycans. Labeling efficiencies shown in FIG. 18 are calculated with following equation: labeling efficiency=labeled peak intensity/(labeled peak intensity+ unlabeled peak intensity)×100%.

Figure 19:
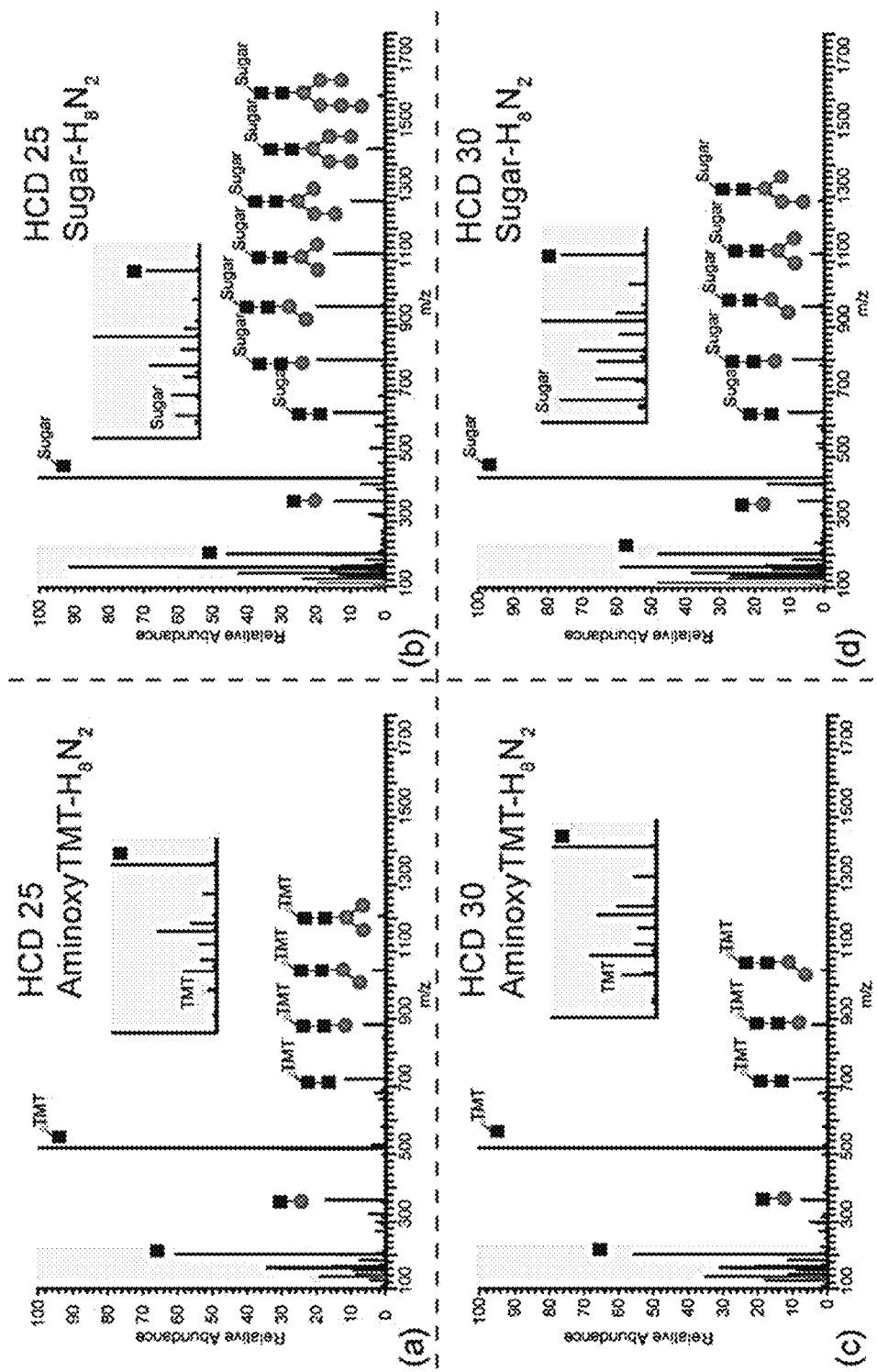
FIGS. 19 and 20 show the relative abundance of fragments using the SUGAR tag of FIG. 17 and AminoxyTMT at different collision energies. SUGAR tag labeled glycans, for both high-mannose and complex type, are able to produce more backbone fragments as well as higher intensity reporter ions.
Figure 20:
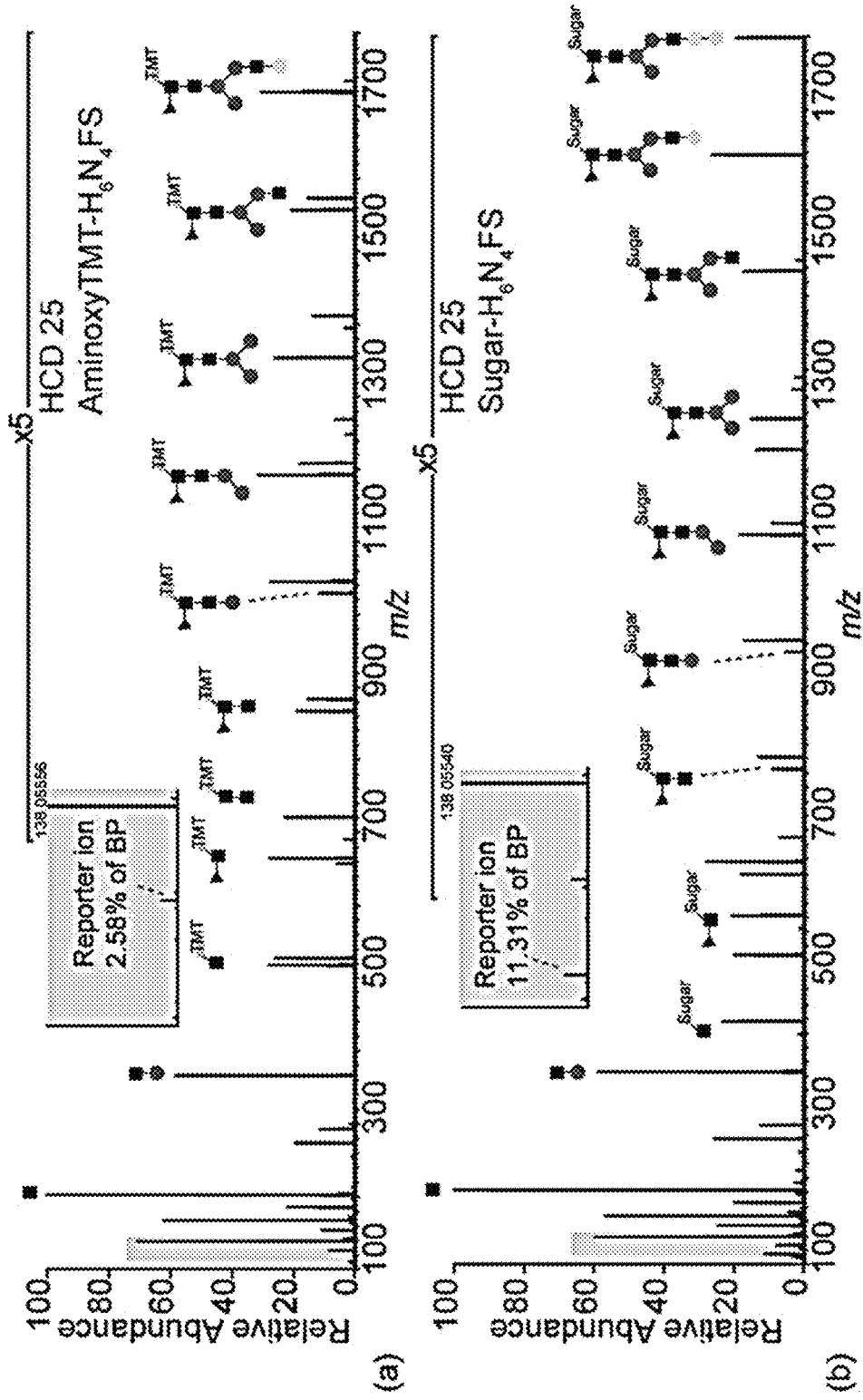

In order to maximize the fragmentation performance of SUGAR-labeled N-glycans, higher-energy collisional dissociation (HCD) performed with different normalized collision energies (NCE) was examined. Most backbone fragments were observed with NCE of 20-25. The reporter ion intensities were elevated with minimal loss of backbone fragment ions by increasing NCE to 30. At even higher NCE, the reporter ions became base peak with a loss of the majority of backbone fragments. Thus, NCE of 30 was chosen to yield high intensities of reporter ions along with abundant backbone fragments. The fragmentation behavior comparisons against aminoxyTMT-labeled glycans are shown in FIGS. 19 and 20. SUGAR-labeled N-glycans tend to produce higher intensities of reporter ions and preserve more backbone fragments. Acidic N-glycans play important biological functions such as stability, degradation and antigenicity (Bork et al., J Pharm Sci 2009, 98 (10): 3499-508), thus attracting a great deal of research interests. However, acidic N-glycans often produce fewer reporter ions than neutral N-glycans. With optimized NCE, SUGAR-labeled acidic N-glycans produced more than a fourfold increase of reporter ion intensities upon fragmentation, demonstrating the SUGAR tag's suitability for acidic N-glycan quantitative analysis.

Figure 29:
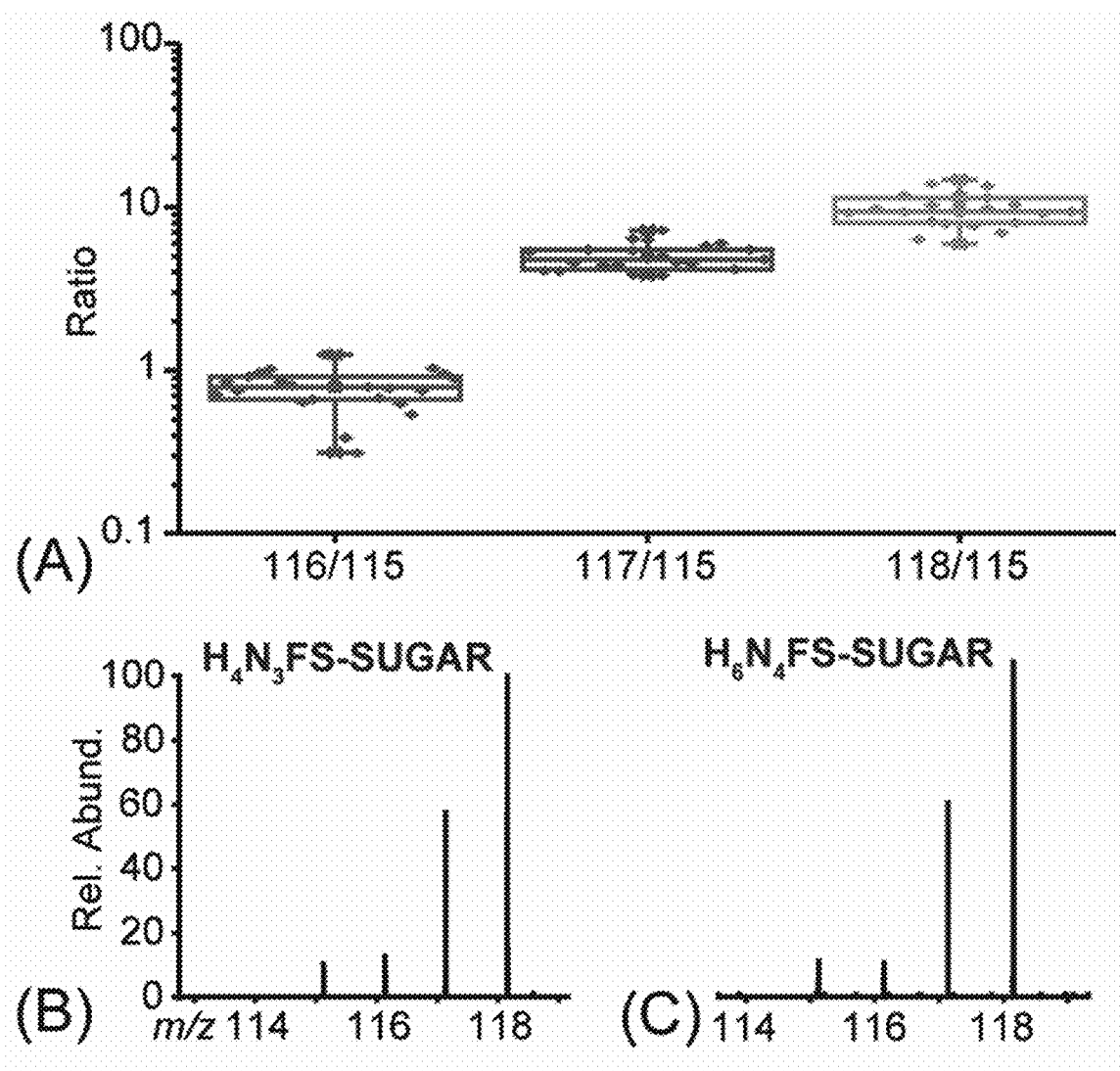
FIG. 29 shows relative quantification performance of 4-plex SUGAR-labeled N-glycans released from BTG. Labeled N-glycans were mixed at ratios of 1:1:5:10 and analyzed in triplicate. The reporter ion intensity ratio results of 116/115, 117/115 and 118/115 are plotted at the log scale. Box plots show the median (line), the 25$^{th}$ and 75$^{th}$ percentile (box), and the 5$^{th}$ and 95$^{th}$ percentile (whiskers) (panel A). Representative MS spectra reporter ion range for SUGAR-labeled N-glycans $H_4N_3FS$ (panel B) and $H_6N_4FS$ (panel C) are shown.
Figure 33:
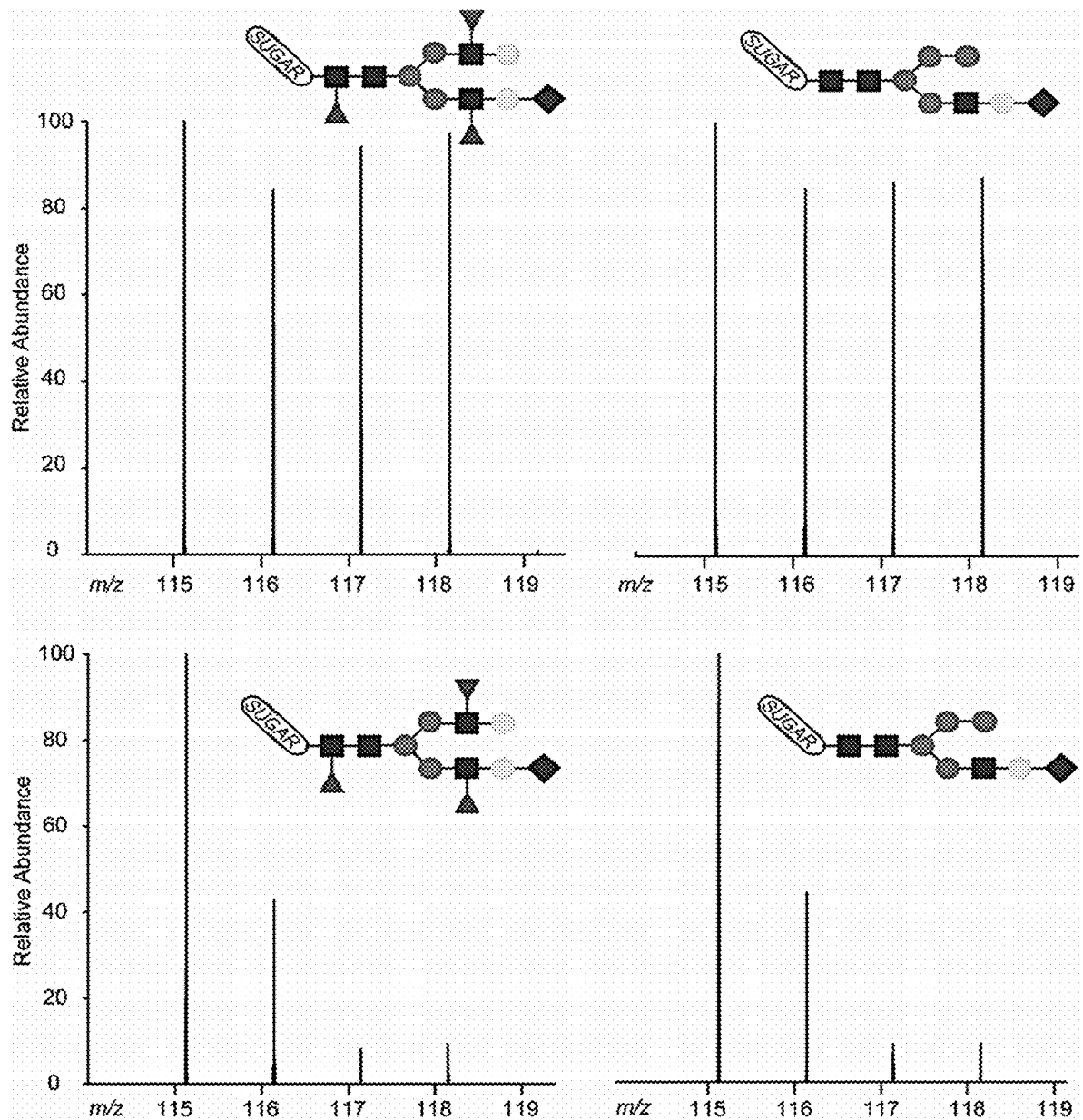
FIG. 33 illustrates representative MS spectra reporter ion ranges for SUGAR-labeled $H_5N_4F_3S$ and $H_5N_3S$ at 1:1:1:1 (top panels) and 10:5:1:1 ratios (bottom panels).

Quantification performance of the 4-plex SUGAR tags was evaluated by labeling N-glycans at known ratios. N-glycans released from BTG were aliquoted into four portions with known ratios at 1:1:1:1, 1:1:5:10 and 10:5:1:1 in triplicate, then labeled with 4-plex SUGAR tags (see, for example, FIG. 33). The intensities of reporter ions in MS$^2$ spectra for each glycan were used to calculate the experimental ratios. In FIG. 29, panel A, experimental 4-plex SUGAR-labeled ratios for N-glycans are plotted against theoretical ratios 1:1:5:10. Representative MS$^2$ reporter ions are shown in FIG. 29, panels B-C for two SUGAR-labeled N-glycans. For all three known ratios, less than 15% relative errors are observed with standard deviation of 0.2, 0.18 and 0.22, demonstrating that SUGAR quantification approach offers accurate quantitative results.

As dynamic expression of N-glycans is highly relevant to biological processes, SUGAR tags were used to quantify N-glycans extracted from a complex biological system at different biological states. More specifically, the SUGAR tags were used to analyze N-glycan changes in human serum proteins of Acute lymphoblastic leukemia (ALL) pediatric patients (see Example 3 below).

Conclusions.

In summary, new isobaric SUGAR tags with amino acid building blocks were developed in this study with improvements in the following aspects: low cost, high yield, complete labeling, high reporter ion yield, accurate and precise quantification, and applicability for complex samples. Hydrazide reactive group enabled glycan reducing end conjugation while stepwise reductive amination strategy was developed to achieve complete glycan labeling. The fragmentation of SUGAR-labeled glycans preserve more backbone fragments with higher reporter ion intensities for qualitative and accurate quantitative glycomics. SUGAR tags also show accurate quantification with broad dynamic range.

The successful development of SUGAR tags offers a useful chemical tool for implementation in many biological and clinical applications. The simple building blocks, complete conjugation, desired fragmentation and accurate quantification make it a precise contrivance for quantitative glycomics study. It is anticipated that the novel SUGAR tagging approach can be widely applied in multiple areas of biomedical research.

Example 3—Applications in Serum Analysis of Children Receiving Chemotherapy for B-Cell Acute Lymphoblastic Leukemia Acute lymphoblastic leukemia (ALL) is one of the most predominant cancers for children which accounts for 26.8% childhood cancer diagnoses worldwide (Kaatsch et al., Cancer Treat Rev 2010, 36 (4): 277-85). The use of chemotherapy of the central nervous system has increased the 5-year-event-free survival rate of around 80% in standard-risk ALL (Gaynon et al., Leukemia 2010, 24 (2): 285-97). However, it is reported that childhood cancer survivors suffer from neurobehavioral morbidity including diverse aspects of cognitive function, attention, processing speed, memory, academic achievement, and emotional health, which has a negative impact on their quality of life (Speechley et al., J Clin Oncol 2006, 24 (16): 2536-43). Previous studies indicated that the neurotoxicity of the chemotherapy could be revealed by alteration of several protein expression levels (Krawczuk-Rybak et al., Adv Med Sci 2012, 57 (2): 266-72). For example, Tau protein level in cerebrospinal fluid (CSF) serves as a biomarker of neuronal loss during active treatment for ALL (Chen et al., Anal Chem 2018, 90 (13): 7817-7823). Glycans, play important roles in biological processes including cell-cell recognition, communication and immunity response. Limited work has been done on quantitative glycomics during chemotherapy. It is important to investigate the glycan level changes during the treatment, which could potentially facilitate biomarker discovery and lead to elucidation of pathogenesis mechanisms and discovery of potential therapeutic strategies and better treatments.

The present invention provides a set of isobaric tags based on the customized DiLeu structure to overcome these difficulties by combining DiLeu backbone with aldehyde-reactive group to create a high performance quantitative glycomics chemical tool. The present isobaric tags were applied to quantitative glycomics of serum samples collected from children receiving chemotherapy for B-cell ALL.

LC-MS/MS Profiling of Glycans Released from Serum Samples of Patients.

Limited work has been done on quantitative glycomics during chemotherapy treatment. It is important to investigate the glycan level changes during the cancer treatment given the aberrant glycan expression in several types of cancers, which will be useful for biomarker discovery and identification of potential pathophysiological mechanisms.

N-glycans were released from serum samples collected from children receiving chemotherapy using the modified Filter Assisted N-Glycan Separation (FANGS) protocol (Abdul Rahman et al., J Proteome Res 2014, 13 (3): 1167-76). HG-DiLeu (SUGAR tag) labeling reaction was performed by stepwise reductive amination. The identification of glycans was performed by accurate mass matching to the human serum glycan database manually at $MS^1$ level with fragmentation analysis at the $MS^2$ level. The relative quantitation between different samples was achieved by comparing the intensities of the reporter ions for each channel manually (FIG. 27).

N-glycan changes in human serum proteins of three B-cell ALL pediatric patients were compared before induction and one month, three months, six months after the chemotherapy. Four-plex SUGAR tags were used to label N-glycans released from equal amounts of human serum proteins at different time points. The same amount of protein was used for PNGase F digestion via FANGS protocol. The digested glycans were hydrolyzed in 1% acetic acid solution for 3 hours. Stepwise reductive amination was employed for the labeling process with different plex for sample collected at different time point. After the clean-up with 1 cc HLB Oasis cartridge, data was acquired on a Q-Exactive Orbitrap mass spectrometer. Manual data analyses of three replicates provided glycan changes during the chemotherapy. A 50% change was set as threshold for up-regulated or down-regulated changes. Since the amount of glycan moiety was typically far less than protein, more serum samples should be used to collect enough glycans for quantitative analysis. The widespread existence of glycan isomers may require alternative separation mechanisms such as capillary electrophoresis, porous graphitic carbon (PGC) chromatography, or ion mobility separation, prior to MS analysis to achieve more accurate quantitative glycan analysis.

Figure 30:
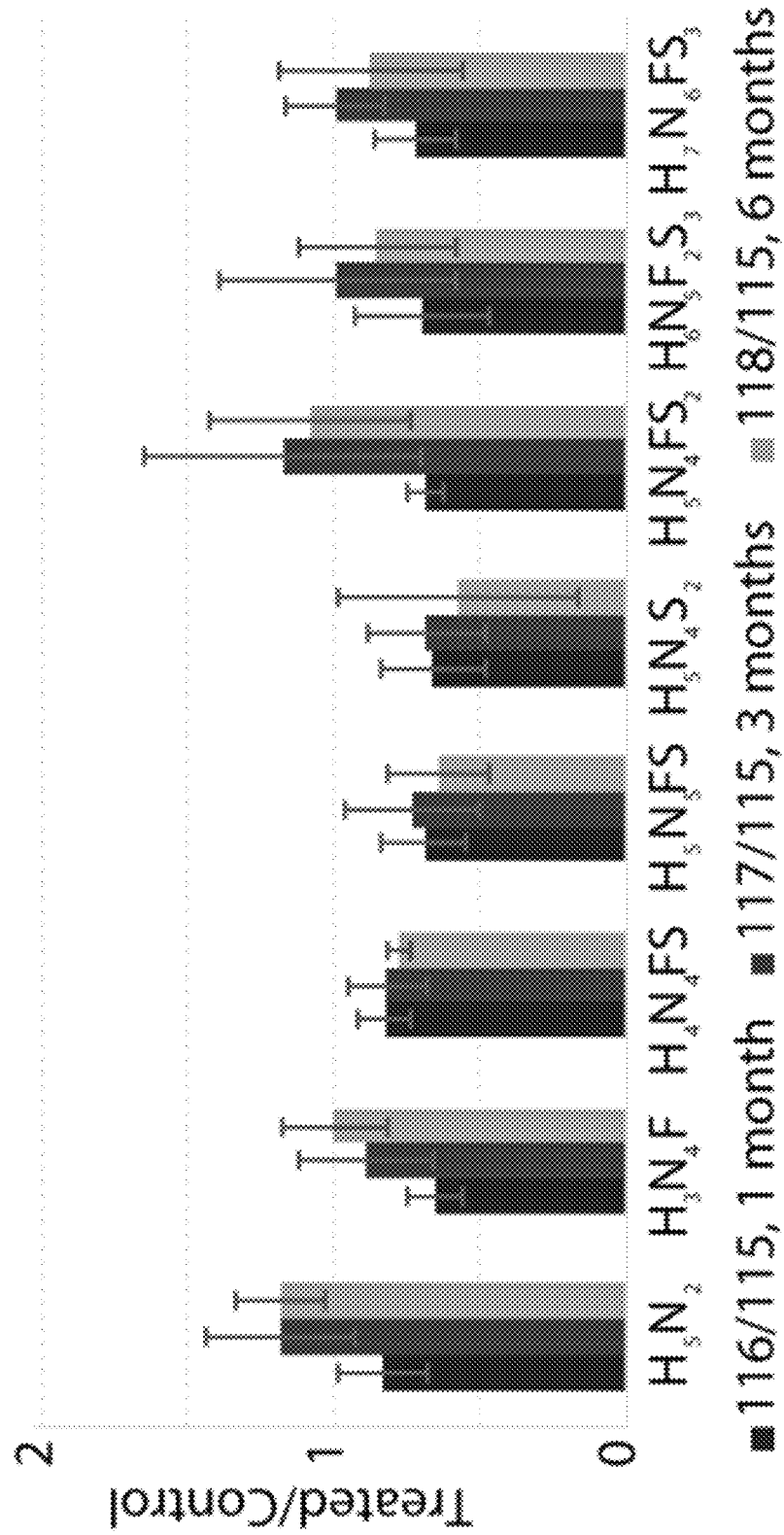
FIG. 30 shows selected N-glycan relative quantification of equal amounts of human serum protein from ALL patients before (SUGAR-115), 1 month (SUGAR-116), 3 months (SUGAR-117), and 6 months (SUGAR-118) after induction chemotherapy. Ratios represent intensities of reporter ions for SUGAR-labeled N-glycans. Error bars represent the standard deviation of three biological replicates.

Quantitative analyses of selected N-glycans are summarized in FIG. 30 with various types of N-glycans. Most quantified N-glycans reveal a trend of down-regulation after induction chemotherapy. In total, 145 N-glycans were identified and quantified with SUGAR labeling approach. Of these, 68 N-glycans were quantified across all three patients. The observed down-regulated N-glycan expression could be explained by elimination of blasts after chemotherapy. As cancer cell metastatic growth can increase branching, fucosylation, and sialylation of N-glycans (Norton et al., J Cell Biochem 2008, 104 (1): 136-49), chemotherapy could decrease such N-glycans by reverting this process. Indeed, the fucosylated and sialylated N-glycans show significant down-regulation in patients after chemotherapy. The proof-of-principle study with SUGAR approach reveals the macroscopic relationship between chemotherapy and N-glycan expression. Further extensive and more in-depth investigations are needed to explore pathogenesis mechanisms and treatment outcomes.

Conclusion and Significance.

The 4-plex SUGAR tag quantitation approach was applied to a complex biological system to investigate N-glycan changes of B-cell ALL pediatric patients prior to and after chemotherapy. It was found that most N-glycans were down-regulated after chemotherapy, possibly due to cancer cell reduction.

Accordingly, the present SUGAR tags provide a novel chemical tool for glycan analysis and quantitative glycomics. The innovative stepwise reductive amination enables almost complete labeling of glycans in a complex biological sample for detection of low abundance species. In the meantime, the high intensities of reporter ions produced via fragmentation, can benefit quantitative analysis of all types of glycans. Additionally, 12-plex HG-DiLeu (SUGAR) is available by adding $^{13}C$ atoms at the N-terminus to enable triplicate analysis of four different samples in a single LC-MS/MS run. Therefore, these tags and methods have broad impacts on both analytical tool development and its application to biological and pharmacological investigations.

Example 4—Carboxylic Acid Labeling with SUGAR Tags

To label glycans through aldehyde and/or ketone groups (glycans), a stepwise reductive amination is typically applied to achieve complete labeling as described above. To improve the labeling of carboxylic acids, organic amide coupling reagents such as EDCI, DCC, DIC, PyAOP, and HATU were used (see, for example, FIG. 2).

For example, carboxylic acid containing compounds were labeled with SUGAR tags by amidation. Twenty μg of carboxylic acid containing compounds (peptides or fatty acids) were mixed with 1 mg SUGAR tag in 100 μL DCM. EDCI was then added to a final concentration of 1 M. The reaction was incubated for 2 h at room temperature. After solvent was removed in vacuo, 1 cc C18 SPE was used to purify SUGAR-labeled carboxylic acid containing compounds. The cartridge was conditioned with 1 mL ACN, 1 mL of 50% ACN, and 1 mL water with 1% TFA. The crude reaction mixture was reconstituted in 1 mL water with 1% TFA and loaded to the conditioned cartridge. The cartridge was then washed three times with 1 mL water with 0.1% TFA, and the labeled peptides were eluted with 1 mL 50% ACN with 0.1% FA and 1 mL 75% ACN with 0.1% FA. The elution fractions were combined, dried in vacuo, and stored in −20° C. for MS analysis.

Figure 36:
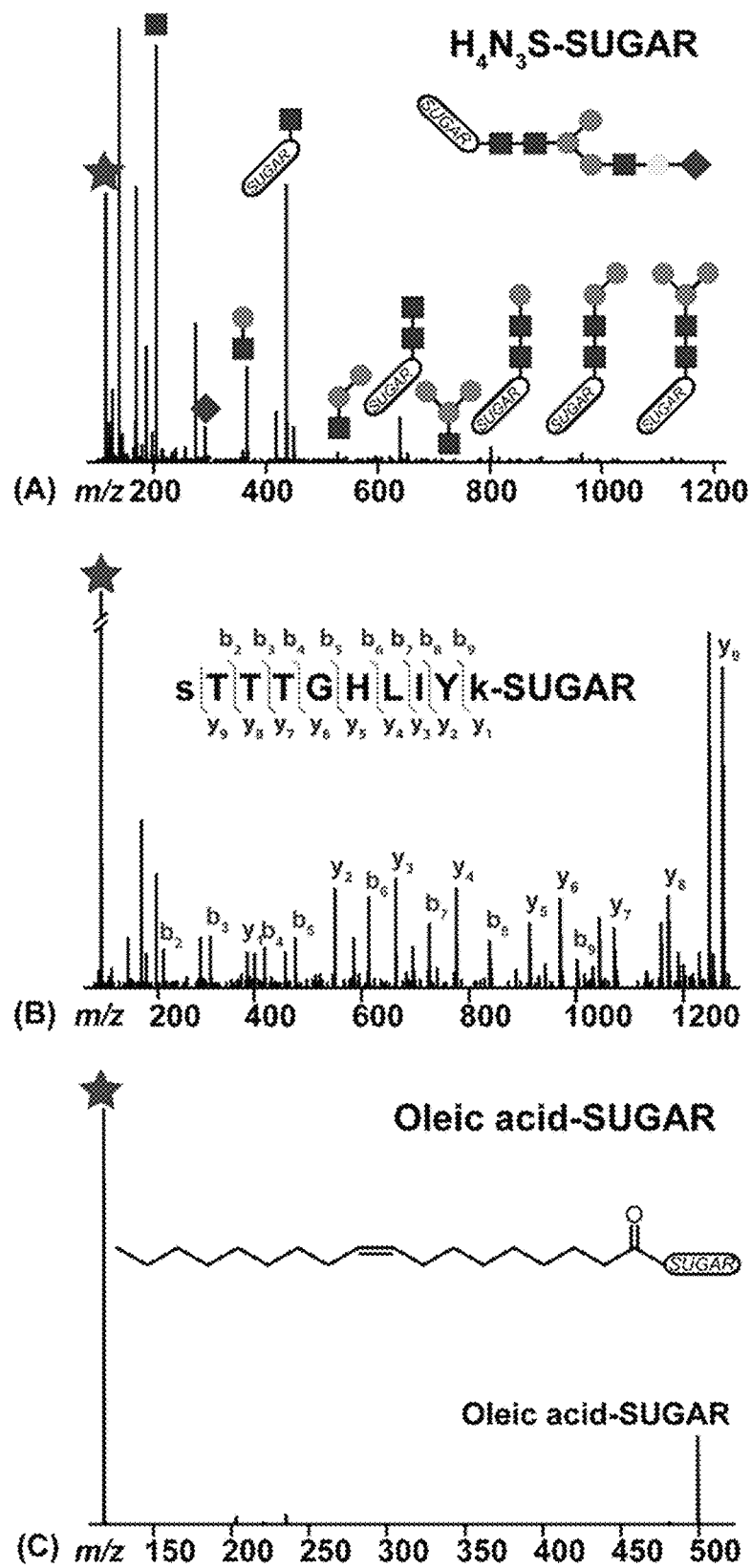
FIG. 36 shows HCD MS/MS fragmentation of a SUGAR-labeled N-glycan $H_4N_3S$ at NCE 30 (panel A), dimethylated peptide at NCE 30 (panel B), and oleic acid at NCE 25 (panel C). The star is a reporter ion upon fragmentation.

The hydrazide group of SUGAR tags enables conjugation with both aldehyde/ketone (glycans) and carboxylic acid (proteins/peptides and lipids) containing compounds. The fragmentations for different types of biomolecules are shown in FIG. 36. Abundant backbone fragments enable isomer identification of biomolecules, while high intensity of reporter ions (annotated with a star) can be utilized for quantification.

Figure 37:
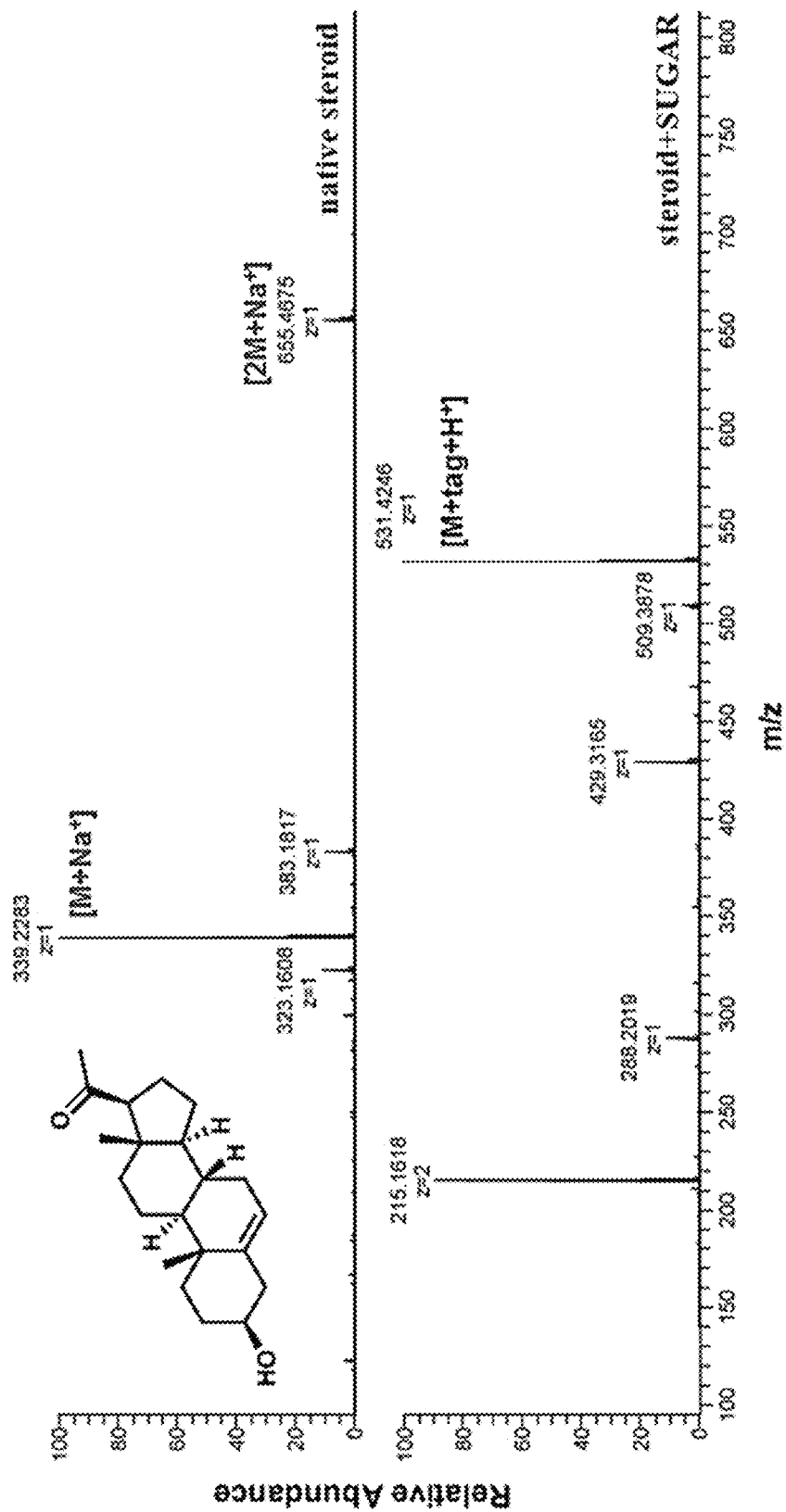
FIGS. 37 and 38 show MS spectra of non-labeled and SUGAR labeled steroids, 3β-hydroxypregn-5-en-20-one (FIG. 37) and 4-androsten-11β,17α-diol-3-one-17β-carboxylic acid (FIG. 38).
Figure 38:
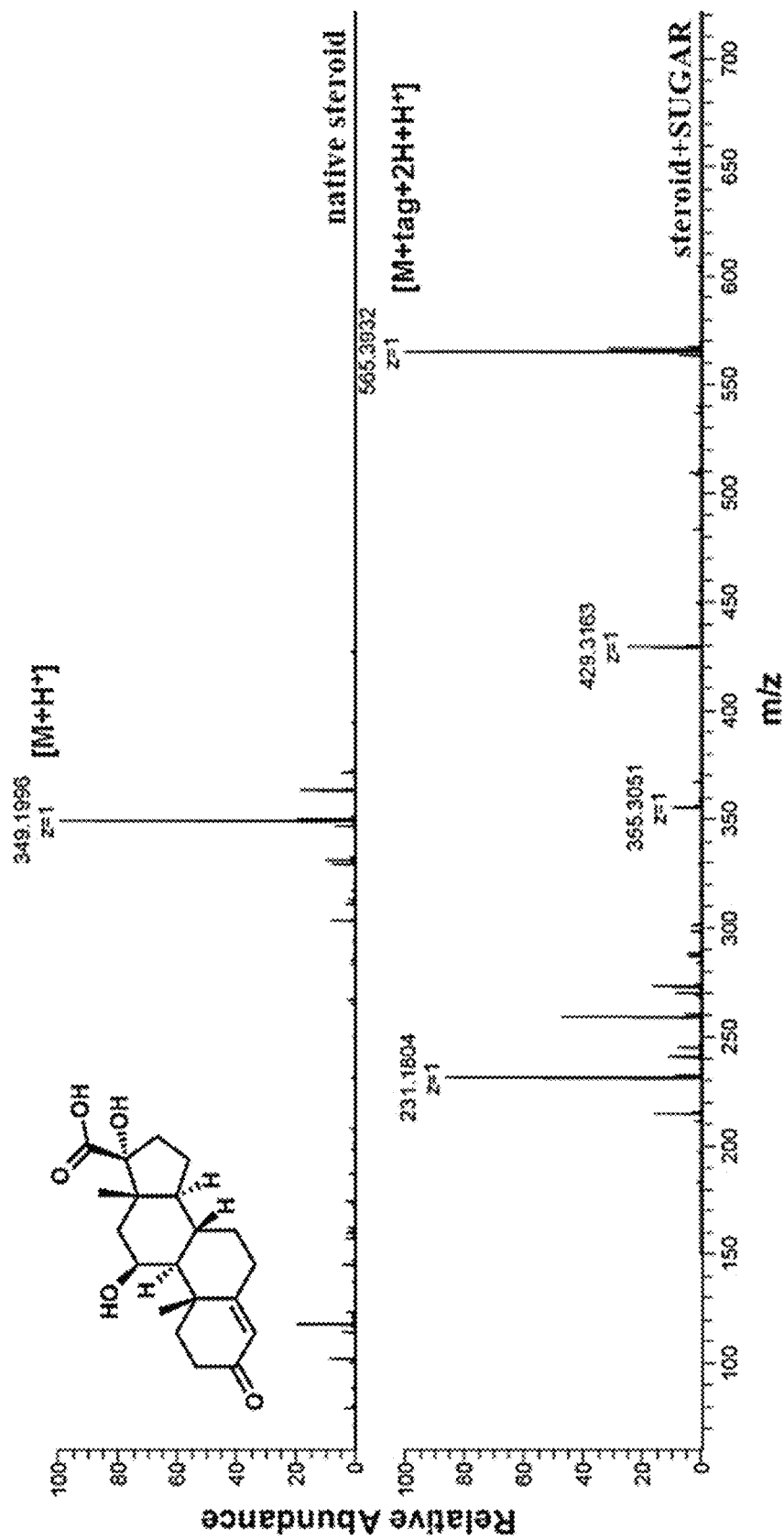

The SUGAR-labeled compounds demonstrated versatile conjugation ability with excellent fragmentation for qualitative and quantitative biomolecule analysis. This feature makes SUGAR tags more distinct and unique compared to other commercial tags, as they are multi-functional group reactive probes for a wide variety of biomolecules. This versatile probe is to enable a broad spectrum of biomolecular quantitative analysis. An exemplary labeled glycan, peptide, and fatty acid are shown in FIG. 36. FIGS. 37 and 38 further illustrate different steroid compounds labeled with the SUGAR tags of the present invention.

Figure 39:
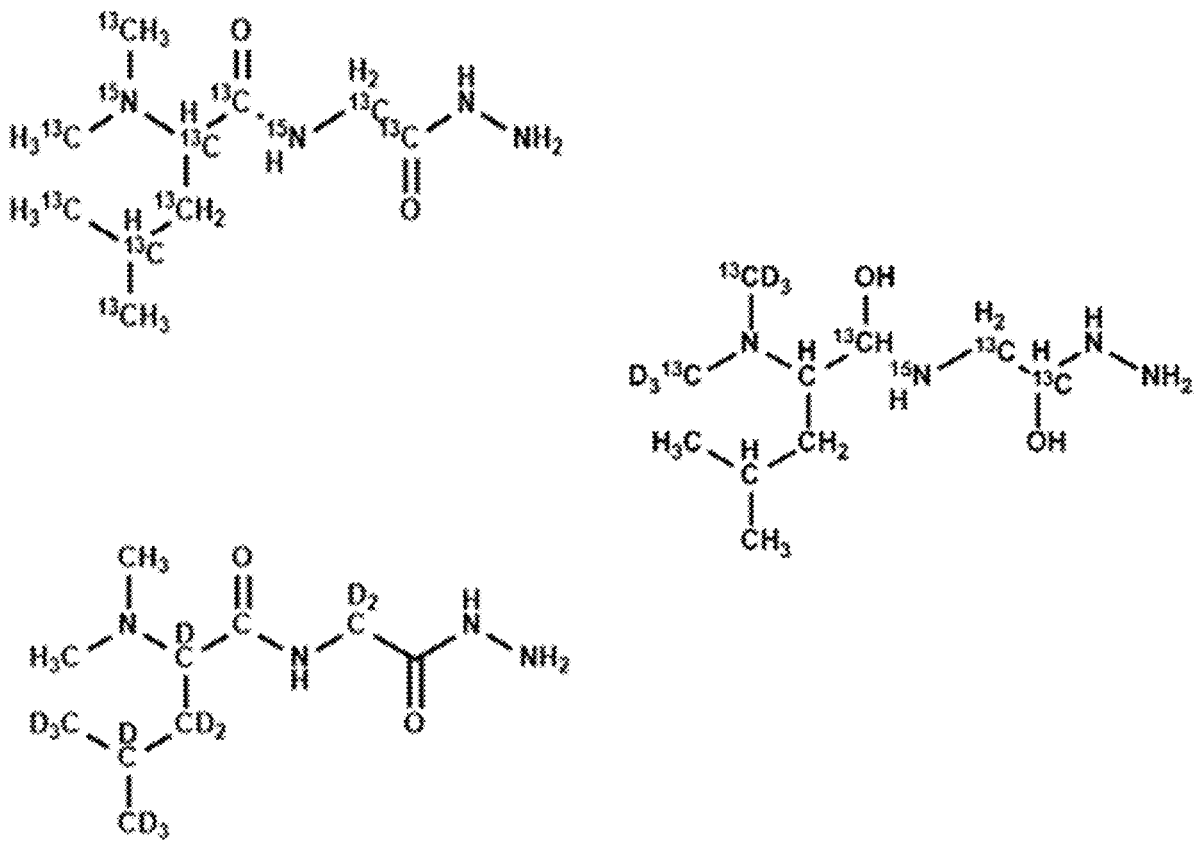
FIG. 39 shows exemplary mass defect SUGAR reagents for $MS^1$ identification and quantification of glycans. Each reagent has a unique combination of heavy isotope substitutions resulting in a mass difference of less than 25 mDa between a reagent and the next closest reagent.
Figure 40:
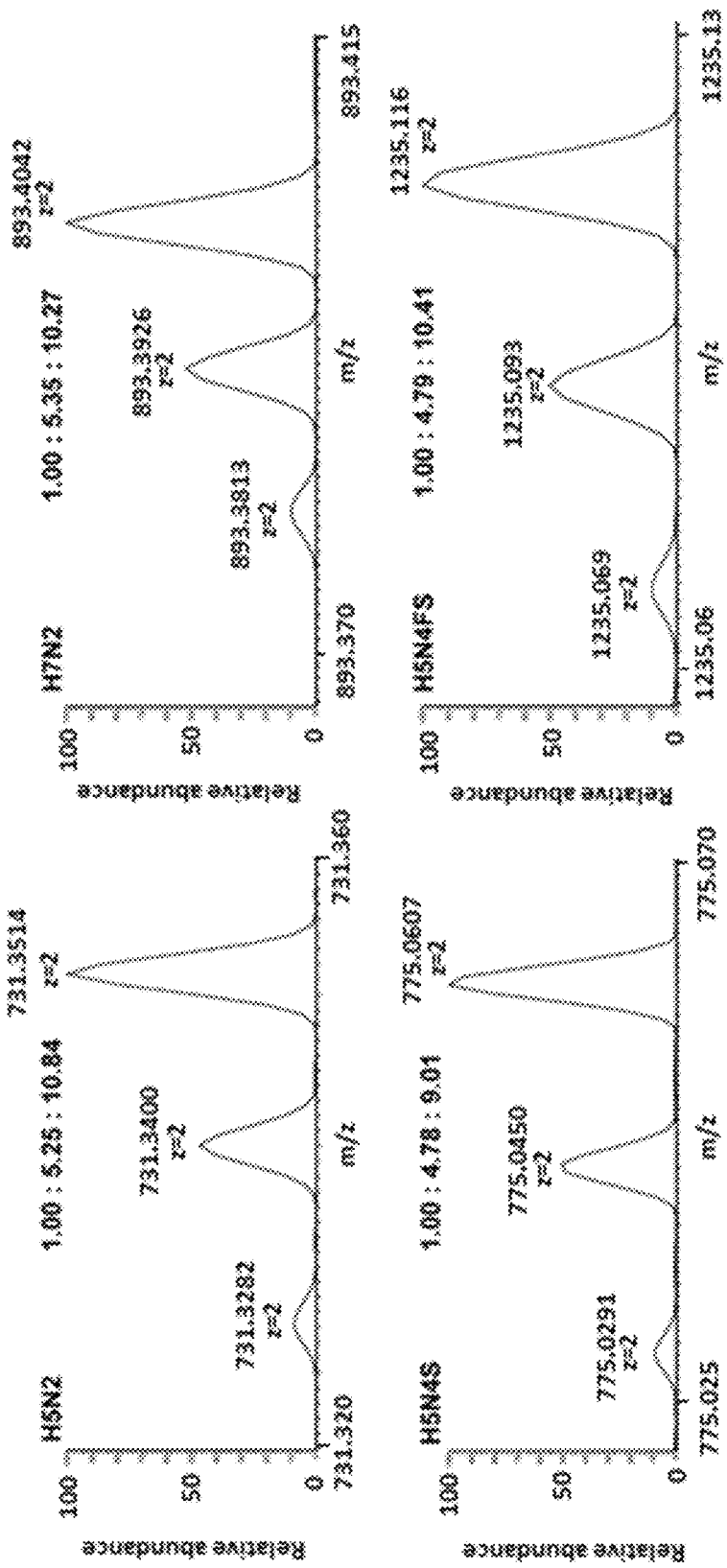
FIG. 40 show mass spectra of different compounds tagged with the mass defect SUGAR reagents of FIG. 39. The tagged compounds were provided in an approximate 1:5:10 ratio which approximately corresponds to the relative abundances shown in the mass spectra.

Example 5—Mass Defect (md)SUGAR for MS1-Based Glycan Quantitation and Quantitative Glycomics Mass defect labeling was developed based on the slight mass difference (less than 1 Da) between different isotopes. The slightly different mass of labeled compounds using this technique enables relative quantification of samples, provides easy spectral interpretation, increased detection sensitivity, and low abundance species quantitation capacity. Most low abundance species might not be selected for $MS^2$-based fragmentation during the widely used data-dependent acquisition (DDA) with isobaric labeling. Since the quantitative results are obtained in full MS spectra, mass defect labeling enables the quantitative analysis for low abundance glycans. With the development of robust and high resolving power instrument, the mass defect labeling is becoming a powerful tool for quantitative glycomics, and can be used as an alternative to the $MS^2$-based isobaric tag quantitative glycomics strategy. This example further provides a 3-plex mdSUGAR reagent for $MS^1$ identification and quantification glycomics (see FIG. 39). Preliminary data has demonstrated good performance (see FIG. 40) as well as the potential to be expanded into 5-plex version corresponding with higher resolution mass spectrometers (i.e., 1,000K).

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

We claim:

1. A method of analyzing a target molecule having an aldehyde, ketone, or carboxylic acid group, said method comprising the steps of:
    a) providing the target molecule;
    b) labeling the target molecule with a tagging reagent, thereby generating a labeled molecule, wherein said tagging reagent comprises: i) a reporter group, ii) an aldehyde reactive group, ketone reactive group, or carboxylic acid reactive group, and iii) a balancing group located between the reporter group and the aldehyde reactive group, ketone reactive group, or carboxylic acid reactive group,
    wherein labeling the target molecule comprises reacting the aldehyde reactive group, ketone reactive group, or carboxylic acid reactive group with an aldehyde, ketone, or carboxylic acid of the target molecule to generate the labeled molecule,
    wherein one or more atoms in the reporter group, the balancing group, or both, are isotopically heavy versions of the one or more atoms, said tagging reagent having the formula of:

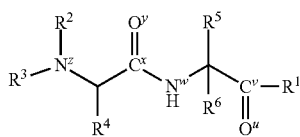

wherein,
$R^1$ is the aldehyde reactive group, ketone reactive group, or carboxylic acid reactive group, wherein the aldehyde reactive group, ketone reactive group, or carboxylic acid reactive group is any functional group able to react with an aldehyde, ketone, or carboxylic acid of the target molecule;

$R^2$ and $R^3$, independently of one another, are selected from the group consisting of branched and unbranched $C_i$ to $C_{12}$ alkyl groups, $C_4$ to $C_{12}$ cycloalkyl groups, $C_2$ to $C_{12}$ alkenyl groups, $C_5$ to $C_{12}$ cycloalkenyl groups, $C_6$ to $C_{12}$ aryl groups and $C_7$ to $C_{12}$ arylalkyl groups, wherein each of $R^2$ and $R^3$ optionally contain one or more $^{13}C$ atoms and one or more deuterium atoms;

$R^4$, $R^5$ and $R^6$, independently of one another, are selected from the group consisting of hydrogen, deuterium, branched and unbranched $C_1$ to $C_{12}$ alkyl groups, $C_4$ to $C_{12}$ cycloalkyl groups, $C_2$ to $C_{12}$ alkenyl groups, $C_5$ to $C_{12}$ cycloalkenyl groups, $C_6$ to $C_{12}$ aryl groups and $C_7$ to $C_{12}$ arylalkyl groups, wherein each of $R^4$, $R^5$ and $R^6$ optionally contain one or more $^{13}C$ atoms and one or more deuterium atoms;

$C^V$ and $C^x$, independently of one another, are $^{12}C$ or $^{13}C$, $O^U$ and $O^Y$, independently of one another, are $^{16}O$ or $^{18}O$; and $N^z$ and $N^W$, independently of one another, are $^{14}N$ or $^{15}N$;
    c) fragmenting the labeled molecule to generate an immonium ion from the labeled molecule; and
    d) detecting and analyzing fragments of the labeled molecule.

2. The method of claim 1 wherein $R^1$ is a hydrazine.

3. The method of claim 1 wherein $R^2$ and $R^3$, independently of one another, are $CH_3$, $^{13}CH_3$, $CDH_2$, $^{13}CDH_2$, $CD_2H$, $^{13}CD_2H$, $CD_3$ or $^{13}CD_3$.

4. The method of claim 1 wherein at least one of: a) $R^2$ or $R^3$ contains a deuterium atom, b) $N^z$ is $^{15}N$, or c) $N^W$ is $^{15}N$.

5. The method of claim 1 wherein $R^6$ is hydrogen or deuterium.

6. The method of claim 1 wherein $R^6$ is hydrogen or deuterium and $R^5$ is selected from the group consisting of:
    a) a methyl group containing one or more deuterium atoms and wherein the carbon is $^{12}C$ or $^{13}C$;
    b) hydrogen;
    c) deuterium;
    d) an isopropyl group containing one or more deuterium atoms and one or more $^{13}C$ atoms; and
    e) a butyl group containing one or more deuterium atoms and one or more $^{13}C$ atoms.

7. The method of claim 1 wherein the labeling step comprises reacting the tagging reagent with a carboxylic acid group of the target molecule.

8. The method of claim 1 wherein the step of labeling the target molecule with a tagging reagent has a labeling efficiency of greater than 90%.

9. The method of claim 1 wherein the tagging reagent has a formula selected from the following:

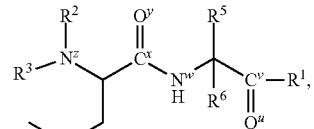

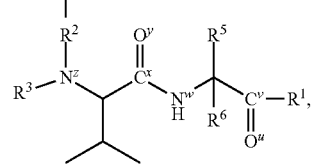

-continued

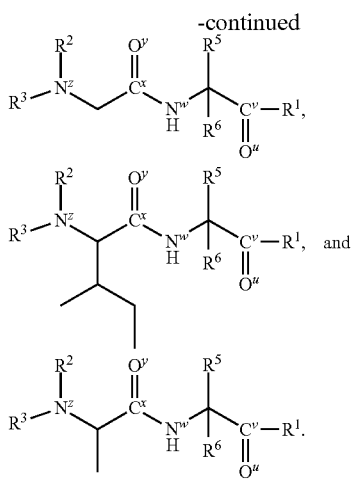

10. The method of claim 1, wherein providing the target molecule in step a) comprises providing two or more samples, each sample comprising an amount of the target molecule;

labeling the target molecule in step b) comprises labeling the target molecule in the two or more samples with two or more tagging reagents of said tagging reagent, wherein each sample is labeled with a different tagging reagent; and the reporter group of each of said two or more tagging reagents has a different mass due to differently isotopically labeled atoms in each reporter group, the balancing group of each of said two or more tagging reagents has a different mass due to differently isotopically labeled atoms in each balancing group, and the aggregate mass of each of said two or more tagging reagents is the same.

11. The method of claim 10 further comprising quantifying amounts of labeled molecule in each sample.

12. The method of claim 10 wherein at least one sample is a biological sample taken from a patient before a treatment is administered to the patient, and one or more samples are biological samples taken from the patient at one or more time periods after the treatment has been administered to the patient.

13. The method of claim 12 wherein the treatment is a cancer treatment.

* * * * *